US007993897B2

(12) United States Patent
Svendsen et al.

(10) Patent No.: US 7,993,897 B2
(45) Date of Patent: Aug. 9, 2011

(54) α-AMYLASE MUTANTS

(75) Inventors: Allan Svendsen, Birkeroed (DK);
Henrik Bisgard-Frantzen, Lyngby
(DK); Torben Vedel Borchert,
Copenhagen N (DK)

(73) Assignee: Novozymes AS, Bagsvaerd (DK)

( * ) Notice: Subject to any disclaimer, the term of this patent is extended or adjusted under 35 U.S.C. 154(b) by 466 days.

(21) Appl. No.: 12/100,506

(22) Filed: Apr. 10, 2008

(65) Prior Publication Data

US 2010/0144575 A1    Jun. 10, 2010

Related U.S. Application Data

(60) Division of application No. 11/064,196, filed on Feb. 22, 2005, now Pat. No. 7,378,264, which is a continuation of application No. 10/184,771, filed on Jun. 28, 2002, now abandoned, which is a continuation of application No. 09/636,252, filed on Aug. 10, 2000, now Pat. No. 6,440,716, which is a continuation of application No. 09/327,563, filed on Jun. 8, 1999, now Pat. No. 7,115,409, which is a continuation of application No. 08/683,838, filed on Jul. 18, 1996, now Pat. No. 6,022,724, which is a continuation-in-part of application No. 08/600,908, filed as application No. PCT/DK96/00057 on Feb. 5, 1996, now Pat. No. 5,989,169.

(30) Foreign Application Priority Data

Feb. 3, 1995  (DK) ........................................ 0128/95
Oct. 23, 1995  (DK) ........................................ 1192/95
Nov. 10, 1995  (DK) ........................................ 1256/95

(51) Int. Cl.
*C12N 9/30* (2006.01)
*C12N 9/00* (2006.01)
*C12N 1/20* (2006.01)
*C12N 15/00* (2006.01)
*C07H 21/04* (2006.01)

(52) U.S. Cl. ..................... 435/203; 435/183; 435/252.3; 435/320.1; 536/23.2

(58) Field of Classification Search ........................ None
See application file for complete search history.

(56) References Cited

U.S. PATENT DOCUMENTS

| 4,600,693 A | 7/1986 | Kindle et al. |
| 5,763,385 A | 6/1998 | Bott |
| 5,830,837 A * | 11/1998 | Bisgard-Frantzen et al. 510/226 |
| 6,143,708 A | 11/2000 | Svendsen et al. |
| 6,204,232 B1 * | 3/2001 | Borchert et al. ............. 510/226 |

FOREIGN PATENT DOCUMENTS

| EP | 0 410 498 | 6/1990 |
| JP | 5506364 | 9/1993 |
| WO | WO 91/00343 | 1/1991 |
| WO | WO 94/02597 | 2/1994 |
| WO | WO 94/18314 | 8/1994 |
| WO | WO 95/10603 A1 | 4/1995 |
| WO | WO 95/35382 | 12/1995 |

OTHER PUBLICATIONS

Abstract—Dialog; File 155, Medline, Dialog Accession No. 08974640, 94289640.
Abstract—Dialog; File 155, Medline, Dialog Accession No. 08958150, 94273150.
Abstract—Dialog; File 5, Biosis Previews; Biosis No. 98219266.
Chang et al., "Crystallization and Preliminary X-ray Crystallographic Analysis of α-Amylase From *Bacillus subtilis*", J. Mol. Biol., 1993, 229, pp. 235-238.
Gray et al., "Structural Genes Encoding the Thermophilic α-Amylases of *Bacillus stearothermophilus* and *Bacillus licheniformis*", Journal of Bacteriology, vol. 166, No. 2, May 1996, pp. 635-643.
Machius et al., (1995) J. Mol. Biol. 246:545-559.
MacGregor (1988) J. Protein Chemistry 7:399-415.
Suzuki et al., (1989) J. Biol. Chem. 264:18933-18938.
Svensson, "Protein Engineering in The Alfa-Amyulase Family: Catalytic Mechanism, Substrate Specificity, and Stability", Plant Molecular Biology, vol. 25, No. 2, pp. 141-157 (1994).
Nakatani et al., "Effect of Modifying Histidine Residues on the Action of *Baciullus amyloliquefaciens* and Barley-Malt Alpha-Amylases", Carbohydrate Research, vol. 257, No. 1, pp. 155-161 (1994).
Buisson, "Three Dimensional Structure of Porcine Pancreatic Alpha-Amylase At 2.9 a Resolution. Role of Calcium Iun Structure and Acitvity", Embo Journal, vol. 6 No. 13, pp. 3903-3916 (1987).
Vihinen, Mauno et al., "Site-Directed Mutagenesis of Athermostable Alfa-Amylase From *Bacillus stearothermophilus*: Putative Role of Three Conserved Residues," Journal of Biochemistry, vol. 107, pp. 267-272 (1990).
Holm et al., "Random Mutagenesis Used to Probe the Structure and Function of *Bactillus stearothermophilus* Alpha-Amylase" Protein Engineering, vol. 3, No. 3, 181-191 (1990).

(Continued)

*Primary Examiner* — Christian Fronda
(74) *Attorney, Agent, or Firm* — Elias Lambiris

(57) ABSTRACT

The present invention relates to a method of constructing a variant of a parent Termamyl-like α-amylase, which variant has α-amylase activity and at least one altered property as compared to the parent α-amylase, comprises
i) analysing the structure of the parent Termamyl-like α-amylase to identify at least one amino acid residue or at least one structural part of the Termamyl-like α-amylase structure, which amino acid residue or structural part is believed to be of relevance for altering the property of the parent Termamyl-like α-amylase (as evaluated on the basis of structural or functional considerations),
ii) constructing a Termamyl-like α-amylase variant, which as compared to the parent Termamyl-like α-amylase, has been modified in the amino acid residue or structural part identified in i) so as to alter the property, and, optionally,
iii) testing the resulting Termamyl-like α-amylase variant with respect to the property in question.

21 Claims, 11 Drawing Sheets

OTHER PUBLICATIONS

Klein et al., "Catalytic Center of Cyclodextrin Glycosyltransferase Derived From X-Ray Structure Analysis Combined With Site-Directed Mutagenesis" Biochemistry, vol. 31, pp. 8740-8746 (1992).

Mizuno, "Crystallization and Preliminary X-Ray Studies of Wild Type and Catalytic-Site Mutant Alfa-Amylase From *Bacillus subtilis*", Journal of Molecular Biology, vol. 234, pp. 1282-1283 (1993).

Larson, "Refined Molecular Structure of Pig Pancreatic Alfa-Amylase At 2-1 a Resolution", Journal of Molecular Biology, vol. 235, pp. 1560-1584 (1994).

Lawson, "Nucleotide Sequence and X-Ray Structure of Cyclodextrin Glycosyltransferase From *Bacillus circulans* Strain 251 in a Maltose-Dependent Crystal Form", Journal of Molecular Biology, vol. 236, pp. 590-600 (1994).

Qian, "Structure and Molecular Model Refinement of Pig Pancreatic Alfa-Amylase At 2-1 a Resolution", Journal of Molecular Biology, vol. 231, pp. 785-799 (1993).

Brady et al., Acta Crystallographica, vol. 47, pp. 527-535 (1991).

Swift, Acta Crystallographica, vol. 47, pp. 535-544 (1991).

Kadziola, "An Alpha-Amylase From Barley and Its Complex With a Substrate Analogue Inhibitor Studied by X-Ray Crystallography", Dep. of Chemistry Uni. of Copenhagen (1993).

MacGregor, Food Hydrocolloids, vol. 1, part 5-6 (1987).

Diderichsen B. et al. "Cloning of Maltogenic Alfa-Amylase From *Bacillus stearothermophilus*" F E M S Microbiol Lett, vol. 56, pp. 53-60 (1988).

Hudson, Practical Immunology, Third Edition (1989).

Sambrook, Molecular Cloning a Laboratory Manual, 2nd Ed. Cold Spring Hjarbor (1989).

Beaucage S.L. et al, Tetrahedron Letters, pp. 1859-1869 (1981).

Matthes et al, The Embo Journal, 801-805 (1984).

Saiki R.K. et al, Science, vol. 239, pp. 487-491 (1988).

Morinaga et al, Biotechnology, vol. 2, pp. 636-646 (1984).

Nelson, Analytical Biochemistry, vol. 180, pp. 147-151 (1989).

Hunkapiller, Nature, vol. 310, pp. 105-111 (1984).

Huguchi, "A General Method of in Vitro Preparation and Specific Mujtagenesis of DNA Fragments: Study of Protein and DNA Interactions", Nucleic Acids Research, vol. 16, pp. 7351-7367 (1988).

Dubnau et al., Journal of Molecular Biology, vol. 56, pp. 209-221 (1971).

Gryczan et al., Journal of Bacteriology, vol. 134, pp. 318-329 (1978).

Erlich, Proc Natl Aced Sci U S A, vol. 74, pp. 1680-1682 (1977).

Boel, Biochemistry, vol. 29, pp. 6244-6249 (1990).

Branden, Introduction to Protein Structure, p. 271 (1991).

Svensson et al., Biochemical Society Transactions, vol. 20, pp. 34-42 (1992).

Lee, "Crystallization and a Preliminary X-Ray Crystallographic Study of α-Amylase from *Bacillus licheniformis*" Archives of Biochemistry and Biophysics, vol. 291, No. 2, pp. 255-257 (1991).

Zhang et al., "Antitumor Agents.152. In Vitro Inhibitory Activity of Etoposide Derivative NPF Against Human Tumor Cell Lines and a Study of Its conformation by X-ray Ctystallography, Molecular Modeling, and NMR Spectroscopy", Journal of Medicinal Chemistry, vol. 37, pp. 1460-1464 (1994).

Holm et al., Chemical Abstracts, vol. 112, p. 351, No. 174785f (1990).

Kim et al., Bull Korean Chemical Society, vol. 15 No. 10, pp. 832-835 (1994).

* cited by examiner

LOOP3(b):TAA:117-185,BA2:98-210

```
  CAT CAT AAT GGA ACA AAT GGT ACT ATC ATG CAA TAT TTC GAA TGG TAT TTG CCA AAT GAC
   H   H   N   G   T   N   G   T   M   M   Q   Y   F   E   W   Y   L   P   N   D

21
  GGC AAT CAT TGG AAC ACG TTG AGG GAT GAC GCA GCT AAC TTA AAG AGT AAA GGG ATA ACA
   G   N   H   W   N   T   L   R   D   D   A   A   N   L   K   S   K   G   I   T

41
  GCT GTA TGG ATC CCA CCT GCA TGG AAG GGG ACT TCC CAG AAT GAT GTA GGT TAT GGA GCC
   A   V   W   I   P   P   A   W   K   G   T   S   Q   N   D   V   G   Y   G   A

61
  TAT GAT TTA TAT GAT CTT GGA GAG TTT AAC CAG AAG GGG ACG GTT CGT ACA AAA TAT GGA
   Y   D   L   Y   D   L   G   E   F   N   Q   K   G   T   V   R   T   K   Y   G

81
  ACA CGC AAC CAG CTA CAG GCT GCG GTG ACC TCT TTA AAA AAT AAC GGC ATT CAG GTA TAT
   T   R   N   Q   L   Q   A   A   V   T   S   L   K   N   N   G   I   Q   V   Y

101
  GGT GAT GTC GTC ATG AAT CAT AAA GGT GGA GCA GAT GGT ACG GAA ATT GTA AAT GCG GTA
   G   D   V   V   M   N   H   K   G   G   A   D   G   T   E   I   V   N   A   V

121
  GAA GTG AAT CGG AGC AAC CGA AAC CAG GAA ACC TCA GGA GAG TAT GCA ATA GAA GCG TGG
   E   V   N   R   S   N   R   N   Q   E   T   S   G   E   Y   A   I   E   A   W

141
  ACA AAG TTT GAT TTT CCT GGA AGA GGA AAT AAC CAT TCC AGC TTT AAG TGG CGC TGG TAT
   T   K   F   D   F   P   G   R   G   N   N   H   S   S   F   K   W   R   W   Y

161
  CAT TTT GAT GGG ACA GAT TGG GAT CAG TCA CGC CAG CTT CAA AAC AAA ATA TAT AAA TTC
   H   F   D   G   T   D   W   D   Q   S   R   Q   L   Q   N   K   I   Y   K   F

181
  AGG GGA ACA GGC AAG GCC TGG GAC TGG GAA GTC GAT ACA GAG AAT GGC AAC TAT GAC TAT
   R   G   T   G   K   A   W   D   W   E   V   D   T   E   N   G   N   Y   D   Y

201
  CTT ATG TAT GCA GAC GTG GAT ATG GAT CAC CCA GAA GTA ATA CAT GAA CTT AGA AAC TGG
   L   M   Y   A   D   V   D   M   D   H   P   E   V   I   H   E   L   R   N   W

221
  GGA GTG TGG TAT ACG AAT ACA CTC AAC CTT GAT GGA TTT ACA ATA GAT CCA GTC AAA CAT
   G   V   W   Y   T   N   T   L   N   L   D   G   F   T   I   D   A   V   K   H

241
  ATA AAA TAT AGC TTT ACG AGA GAT TGG CTT ACA CAT GTC CGT AAC ACC ACA GGT AAA CCA
   I   K   Y   S   F   T   R   D   W   L   T   H   V   R   N   T   T   G   K   P

261
  ATG TTT GCA GTG GCT GAG TTT TGG AAA AAT GAC CTT GGT GCA ATT GAA AAC TAT TTG AAT
   M   F   A   V   A   E   F   W   K   N   D   L   G   A   I   E   N   Y   L   N

281
  AAA ACA AGT TGG AAT CAC TCC GTG TTT GAT GTT CCT CTC CAC TAT AAT TTG TAC AAT GCA
   K   T   S   W   N   H   S   V   F   D   V   P   L   H   Y   N   L   Y   N   A
```

Fig. 8

```
301
TCT AAT AGC GGT GGT TAT TAT GAT ATG AGA AAT ATT TTA AAT GGT TCT GTG GTG CAA AAA
 S   N   S   G   G   Y   Y   D   M   R   N   I   L   N   G   S   V   V   Q   K

321
CAT CCA ACA CAT GCC GTT ACT TTT GTT GAT AAC CAT GAT TCT CAG CCC GGG GAA GCA TTG
 H   P   T   H   A   V   T   F   V   D   N   H   D   S   Q   P   G   E   A   L

341
GAA TCC TTT GTT CAA CAA TGG TTT AAA CCA CTT GCA TAT GCA TTG GTT CTG ACA AGG GAA
 E   S   F   V   Q   Q   W   F   K   P   L   A   Y   A   L   V   L   T   R   E

361
CAA GGT TAT CCT TCC GTA TTT TAT GGG GAT TAC TAC GGT ATC CCA ACC CAT GGT GTT CCG
 Q   G   Y   P   S   V   F   Y   G   D   Y   Y   G   I   P   T   H   G   V   P

381
GCT ATG AAA TCT AAA ATA GAC CCT CTT CTG CAG GCA CGT CAA ACT TTT GCC TAT GGT ACG
 A   M   K   S   K   I   D   P   L   L   Q   A   R   Q   T   F   A   Y   G   T

401
CAG CAT GAT TAC TTT GAT CAT CAT GAT ATT ATC GGT TGG ACA AGA GAG GGA AAT AGC TCC
 Q   H   D   Y   F   D   H   H   D   I   I   G   W   T   R   E   G   N   S   S

421
CAT CCA AAT TCA GGC CTT GCC ACC ATT ATG TCA GAT GGT CCA ACT GGT AAC AAA TGG ATG
 H   P   N   S   G   L   A   T   I   M   S   D   G   P   G   G   N   K   W   M

441
TAT GTG GCG AAA AAT AAA GCG GGA CAA GTT TGG AGA GAT ATT ACC GGA AAT AGG ACA GGC
 Y   V   G   K   N   K   A   G   Q   V   W   R   D   I   T   G   N   R   T   G

261
ACC GTC ACA ATT AAT GCA GAC GGA TGG GGT AAT TTC TCT GTT AAT GGA GGG TCC GTT TCG
 T   V   T   I   N   A   D   G   W   G   N   F   S   V   N   G   G   S   V   S

481
GTT TGG GTC AAG CAA TAA
 V   W   V   K   Q   *
```

Fig. 8 (cont.)

SEQUENCE LISTING

```
<160> NUMBER OF SEQ ID NOS: 13

<210> SEQ ID NO 1
<211> LENGTH: 1920
<212> TYPE: DNA
<213> ORGANISM: Bacillus licheniformis
<220> FEATURE:
<221> NAME/KEY: CDS
<222> LOCATION: (334)..(1869)
<220> FEATURE:
<221> NAME/KEY: sig_peptide
<222> LOCATION: (334)..(420)
<220> FEATURE:
<221> NAME/KEY: mat_peptide
<222> LOCATION: (421)..(1869)

<400> SEQUENCE: 1
cggaagattg gaagtacaaa aataagcaaa agattgtcaa tcatgtcatg agccatgcgg      60
gagacggaaa aatcgtctta atgcacgata tttatgcaac gttcgcagat gctgctgaag     120
agattattaa aaagctgaaa gcaaaaggct atcaattggt aactgtatct cagcttgaag     180
aagtgaagaa gcagagaggc tattgaataa atgagtagaa gcgccatatc ggcgcttttc     240
ttttggaaga aaatataggg aaaatggtac ttgttaaaaa ttcggaatat ttatacaaca     300
tcatatgttt cacattgaaa ggggaggaga atc atg aaa caa caa aaa cgg ctt     354
                                    Met Lys Gln Gln Lys Arg Leu
                                                        -25 tac gcc cga ttg ctg acg ctg tta ttt gcg ctc atc ttc ttg ctg cct      402
Tyr Ala Arg Leu Leu Thr Leu Leu Phe Ala Leu Ile Phe Leu Leu Pro
            -20                 -15                 -10 cat tct gca gca gcg gcg gca aat ctt aat ggg acg ctg atg cag tat      450
His Ser Ala Ala Ala Ala Ala Asn Leu Asn Gly Thr Leu Met Gln Tyr
         -5             -1   1               5                  10 ttt gaa tgg tac atg ccc aat gac ggc caa cat tgg agg cgt ttg caa      498
Phe Glu Trp Tyr Met Pro Asn Asp Gly Gln His Trp Arg Arg Leu Gln
                 15                  20                  25 aac gac tcg gca tat ttg gct gaa cac ggt att act gcc gtc tgg att      546
Asn Asp Ser Ala Tyr Leu Ala Glu His Gly Ile Thr Ala Val Trp Ile
             30                  35                  40
```

```
ccc ccg gca tat aag gga acg agc caa gcg gat gtg ggc tac ggt gct      594
Pro Pro Ala Tyr Lys Gly Thr Ser Gln Ala Asp Val Gly Tyr Gly Ala
         45                  50                  55 tac gac ctt tat gat tta ggg gag ttt cat caa aaa ggg acg gtt cgg      642
Tyr Asp Leu Tyr Asp Leu Gly Glu Phe His Gln Lys Gly Thr Val Arg
    60                  65                  70 aca aag tac ggc aca aaa gga gag ctg caa tct gcg atc aaa agt ctt      690
Thr Lys Tyr Gly Thr Lys Gly Glu Leu Gln Ser Ala Ile Lys Ser Leu
75                  80                  85                  90 cat tcc cgc gac att aac gtt tac ggg gat gtg gtc atc aac cac aaa      738
His Ser Arg Asp Ile Asn Val Tyr Gly Asp Val Val Ile Asn His Lys
                95                  100                 105 ggc ggc gct gat gcg acc gaa gat gta acc gcg gtt gaa gtc gat ccc      786
Gly Gly Ala Asp Ala Thr Glu Asp Val Thr Ala Val Glu Val Asp Pro
            110                 115                 120 gct gac cgc aac cgc gta att tca gga gaa cac cta att aaa gcc tgg      834
Ala Asp Arg Asn Arg Val Ile Ser Gly Glu His Leu Ile Lys Ala Trp
        125                 130                 135 aca cat ttt cat ttt ccg ggg cgc ggc agc aca tac agc gat ttt aaa      882
Thr His Phe His Phe Pro Gly Arg Gly Ser Thr Tyr Ser Asp Phe Lys
    140                 145                 150 tgg cat tgg tac cat ttt gac gga acc gat tgg gac gag tcc cga aag      930
Trp His Trp Tyr His Phe Asp Gly Thr Asp Trp Asp Glu Ser Arg Lys
155                 160                 165                 170 ctg aac cgc atc tat aag ttt caa gga aag gct tgg gat tgg gaa gtt      978
Leu Asn Arg Ile Tyr Lys Phe Gln Gly Lys Ala Trp Asp Trp Glu Val
                175                 180                 185 tcc aat gaa aac ggc aac tat gat tat ttg atg tat gcc gac atc gat     1026
Ser Asn Glu Asn Gly Asn Tyr Asp Tyr Leu Met Tyr Ala Asp Ile Asp
            190                 195                 200 tat gac cat cct gat gtc gca gca gaa att aag aga tgg ggc act tgg     1074
Tyr Asp His Pro Asp Val Ala Ala Glu Ile Lys Arg Trp Gly Thr Trp
        205                 210                 215 tat gcc aat gaa ctg caa ttg gac ggt ttc cgt ctt gat gct gtc aaa     1122
Tyr Ala Asn Glu Leu Gln Leu Asp Gly Phe Arg Leu Asp Ala Val Lys
    220                 225                 230 cac att aaa ttt tct ttt ttg cgg gat tgg gtt aat cat gtc agg gaa     1170
His Ile Lys Phe Ser Phe Leu Arg Asp Trp Val Asn His Val Arg Glu
235                 240                 245                 250 aaa acg ggg aag gaa atg ttt acg gta gct gaa tat tgg cag aat gac     1218
Lys Thr Gly Lys Glu Met Phe Thr Val Ala Glu Tyr Trp Gln Asn Asp
                255                 260                 265 ttg ggc gcg ctg gaa aac tat ttg aac aaa aca aat ttt aat cat tca     1266
Leu Gly Ala Leu Glu Asn Tyr Leu Asn Lys Thr Asn Phe Asn His Ser
            270                 275                 280 gtg ttt gac gtg ccg ctt cat tat cag ttc cat gct gca tcg aca cag     1314
Val Phe Asp Val Pro Leu His Tyr Gln Phe His Ala Ala Ser Thr Gln
        285                 290                 295 gga ggc ggc tat gat atg agg aaa ttg ctg aac ggt acg gtc gtt tcc     1362
Gly Gly Gly Tyr Asp Met Arg Lys Leu Leu Asn Gly Thr Val Val Ser
    300                 305                 310 aag cat ccg ttg aaa tcg gtt aca ttt gtc gat aac cat gat aca cag     1410
Lys His Pro Leu Lys Ser Val Thr Phe Val Asp Asn His Asp Thr Gln
315                 320                 325                 330 ccg ggg caa tcg ctt gag tcg act gtc caa aca tgg ttt aag ccg ctt     1458
Pro Gly Gln Ser Leu Glu Ser Thr Val Gln Thr Trp Phe Lys Pro Leu
                335                 340                 345 gct tac gct ttt att ctc aca agg gaa tct gga tac cct cag gtt ttc     1506
Ala Tyr Ala Phe Ile Leu Thr Arg Glu Ser Gly Tyr Pro Gln Val Phe
            350                 355                 360
```

```
tac ggg gat atg tac ggg acg aaa gga gac tcc cag cgc gaa att cct    1554
Tyr Gly Asp Met Tyr Gly Thr Lys Gly Asp Ser Gln Arg Glu Ile Pro
    365                 370                 375 gcc ttg aaa cac aaa att gaa ccg atc tta aaa gcg aga aaa cag tat    1602
Ala Leu Lys His Lys Ile Glu Pro Ile Leu Lys Ala Arg Lys Gln Tyr
    380                 385                 390 gcg tac gga gca cag cat gat tat ttc gac cac cat gac att gtc ggc    1650
Ala Tyr Gly Ala Gln His Asp Tyr Phe Asp His His Asp Ile Val Gly
395                 400                 405                 410 tgg aca agg gaa ggc gac agc tcg gtt gca aat tca ggt ttg gcg gca    1698
Trp Thr Arg Glu Gly Asp Ser Ser Val Ala Asn Ser Gly Leu Ala Ala
                415                 420                 425 tta ata aca gac gga ccc ggt ggg gca aag cga atg tat gtc ggc cgg    1746
Leu Ile Thr Asp Gly Pro Gly Gly Ala Lys Arg Met Tyr Val Gly Arg
            430                 435                 440 caa aac gcc ggt gag aca tgg cat gac att acc gga aac cgt tcg gag    1794
Gln Asn Ala Gly Glu Thr Trp His Asp Ile Thr Gly Asn Arg Ser Glu
        445                 450                 455 ccg gtt gtc atc aat tcg gaa ggc tgg gga gag ttt cac gta aac ggc    1842
Pro Val Val Ile Asn Ser Glu Gly Trp Gly Glu Phe His Val Asn Gly
    460                 465                 470 ggg tcg gtt tca att tat gtt caa aga tagaagagca gagaggacgg          1889
Gly Ser Val Ser Ile Tyr Val Gln Arg
475                 480 atttcctgaa ggaaatccgt tttttttattt t                                1920

<210> SEQ ID NO 2
<211> LENGTH: 512
<212> TYPE: PRT
<213> ORGANISM: Bacillus licheniformis

<400> SEQUENCE: 2

Met Lys Gln Gln Lys Arg Leu Tyr Ala Arg Leu Leu Thr Leu Leu Phe
                -25                 -20                 -15

Ala Leu Ile Phe Leu Leu Pro His Ser Ala Ala Ala Ala Asn Leu
        -10                  -5                  -1   1

Asn Gly Thr Leu Met Gln Tyr Phe Glu Trp Tyr Met Pro Asn Asp Gly
  5                  10                  15

Gln His Trp Arg Arg Leu Gln Asn Asp Ser Ala Tyr Leu Ala Glu His
20                  25                  30                  35

Gly Ile Thr Ala Val Trp Ile Pro Pro Ala Tyr Lys Gly Thr Ser Gln
                40                  45                  50

Ala Asp Val Gly Tyr Gly Ala Tyr Asp Leu Tyr Asp Leu Gly Glu Phe
            55                  60                  65

His Gln Lys Gly Thr Val Arg Thr Lys Tyr Gly Thr Lys Gly Glu Leu
        70                  75                  80

Gln Ser Ala Ile Lys Ser Leu His Ser Arg Asp Ile Asn Val Tyr Gly
    85                  90                  95

Asp Val Val Ile Asn His Lys Gly Gly Ala Asp Ala Thr Glu Asp Val
100                 105                 110                 115

Thr Ala Val Glu Val Asp Pro Ala Asp Arg Asn Arg Val Ile Ser Gly
                120                 125                 130

Glu His Leu Ile Lys Ala Trp Thr His Phe His Phe Pro Gly Arg Gly
            135                 140                 145

Ser Thr Tyr Ser Asp Phe Lys Trp His Trp Tyr His Phe Asp Gly Thr
        150                 155                 160

Asp Trp Asp Glu Ser Arg Lys Leu Asn Arg Ile Tyr Lys Phe Gln Gly
```

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |

Lys Ala Trp Asp Trp Glu Val Ser Asn Glu Asn Gly Asn Tyr Asp Tyr
180                 185                 190                 195

Leu Met Tyr Ala Asp Ile Asp Tyr Asp His Pro Asp Val Ala Ala Glu
            200                 205                 210

Ile Lys Arg Trp Gly Thr Trp Tyr Ala Asn Glu Leu Gln Leu Asp Gly
                215                 220                 225

Phe Arg Leu Asp Ala Val Lys His Ile Lys Phe Ser Phe Leu Arg Asp
            230                 235                 240

Trp Val Asn His Val Arg Glu Lys Thr Gly Lys Glu Met Phe Thr Val
    245                 250                 255

Ala Glu Tyr Trp Gln Asn Asp Leu Gly Ala Leu Glu Asn Tyr Leu Asn
260                 265                 270                 275

Lys Thr Asn Phe Asn His Ser Val Phe Asp Val Pro Leu His Tyr Gln
                280                 285                 290

Phe His Ala Ala Ser Thr Gln Gly Gly Gly Tyr Asp Met Arg Lys Leu
            295                 300                 305

Leu Asn Gly Thr Val Val Ser Lys His Pro Leu Lys Ser Val Thr Phe
            310                 315                 320

Val Asp Asn His Asp Thr Gln Pro Gly Gln Ser Leu Glu Ser Thr Val
325                 330                 335

Gln Thr Trp Phe Lys Pro Leu Ala Tyr Ala Phe Ile Leu Thr Arg Glu
340                 345                 350                 355

Ser Gly Tyr Pro Gln Val Phe Tyr Gly Asp Met Tyr Gly Thr Lys Gly
                360                 365                 370

Asp Ser Gln Arg Glu Ile Pro Ala Leu Lys His Lys Ile Glu Pro Ile
            375                 380                 385

Leu Lys Ala Arg Lys Gln Tyr Ala Tyr Gly Ala Gln His Asp Tyr Phe
            390                 395                 400

Asp His His Asp Ile Val Gly Trp Thr Arg Glu Gly Asp Ser Ser Val
    405                 410                 415

Ala Asn Ser Gly Leu Ala Ala Leu Ile Thr Asp Gly Pro Gly Gly Ala
420                 425                 430                 435

Lys Arg Met Tyr Val Gly Arg Gln Asn Ala Gly Glu Thr Trp His Asp
                440                 445                 450

Ile Thr Gly Asn Arg Ser Glu Pro Val Val Ile Asn Ser Glu Gly Trp
            455                 460                 465

Gly Glu Phe His Val Asn Gly Gly Ser Val Ser Ile Tyr Val Gln Arg
            470                 475                 480

<210> SEQ ID NO 3
<211> LENGTH: 2084
<212> TYPE: DNA
<213> ORGANISM: Bacillus amyloliquefaciens
<220> FEATURE:
<221> NAME/KEY: CDS
<222> LOCATION: (250)..(1791)
<220> FEATURE:
<221> NAME/KEY: sig_peptide
<222> LOCATION: (250)..(342)
<220> FEATURE:
<221> NAME/KEY: mat_peptide
<222> LOCATION: (343)..(1791)

<400> SEQUENCE: 3
gccccgcaca tacgaaaaga ctggctgaaa acattgagcc tttgatgact gatgatttgg    60
ctgaagaagt ggatcgattg tttgagaaaa gaagaagacc ataaaaatac cttgtctgtc   120

```
-continued atcagacagg gtattttta tgctgtccag actgtccgct gtgtaaaaat aaggaataaa       180
ggggggttgt tattatttta ctgatatgta aatataatt tgtataagaa atgagaggg       240 agaggaaac atg att caa aaa cga aag cgg aca gtt tcg ttc aga ctt gtg    291
         Met Ile Gln Lys Arg Lys Arg Thr Val Ser Phe Arg Leu Val
             -30                 -25                 -20 ctt atg tgc acg ctg tta ttt gtc agt ttg ccg att aca aaa aca tca     339
Leu Met Cys Thr Leu Leu Phe Val Ser Leu Pro Ile Thr Lys Thr Ser
        -15                 -10                 -5 gcc gta aat ggc acg ctg atg cag tat ttt gaa tgg tat acg ccg aac     387
Ala Val Asn Gly Thr Leu Met Gln Tyr Phe Glu Trp Tyr Thr Pro Asn
-1   1              5                   10                  15 gac ggc cag cat tgg aaa cga ttg cag aat gat gcg gaa cat tta tcg     435
Asp Gly Gln His Trp Lys Arg Leu Gln Asn Asp Ala Glu His Leu Ser
                20                  25                  30 gat atc gga atc act gcc gtc tgg att cct ccc gca tac aaa gga ttg     483
Asp Ile Gly Ile Thr Ala Val Trp Ile Pro Pro Ala Tyr Lys Gly Leu
                35                  40                  45 agc caa tcc gat aac gga tac gga cct tat gat ttg tat gat tta gga    531
Ser Gln Ser Asp Asn Gly Tyr Gly Pro Tyr Asp Leu Tyr Asp Leu Gly
            50                  55                  60 gaa ttc cag caa aaa ggg acg gtc aga acg aaa tac ggc aca aaa tca    579
Glu Phe Gln Gln Lys Gly Thr Val Arg Thr Lys Tyr Gly Thr Lys Ser
        65                  70                  75 gag ctt caa gat gcg atc gga tca ctg cat tcc cgg aac gtc caa gta    627
Glu Leu Gln Asp Ala Ile Gly Ser Leu His Ser Arg Asn Val Gln Val
80                  85                  90                  95 tac gga gat gtg gtt ttg aat cat aag gct ggt gct gat gca aca gaa    675
Tyr Gly Asp Val Val Leu Asn His Lys Ala Gly Ala Asp Ala Thr Glu
                100                 105                 110 gat gta act gcc gtc gaa gtc aat ccg gcc aat aga aat cag gaa act    723
Asp Val Thr Ala Val Glu Val Asn Pro Ala Asn Arg Asn Gln Glu Thr
                115                 120                 125 tcg gag gaa tat caa atc aaa gcg tgg acg gat ttt cgt ttt ccg ggc    771
Ser Glu Glu Tyr Gln Ile Lys Ala Trp Thr Asp Phe Arg Phe Pro Gly
        130                 135                 140 cgt gga aac acg tac agt gat ttt aaa tgg cat tgg tat cat ttc gac    819
Arg Gly Asn Thr Tyr Ser Asp Phe Lys Trp His Trp Tyr His Phe Asp
        145                 150                 155 gga gcg gac tgg gat gaa tcc cgg aag atc agc cgc atc ttt aag ttt    867
Gly Ala Asp Trp Asp Glu Ser Arg Lys Ile Ser Arg Ile Phe Lys Phe
160                 165                 170                 175 cgt ggg gaa gga aaa gcg tgg gat tgg gaa gta tca agt gaa aac ggc    915
Arg Gly Glu Gly Lys Ala Trp Asp Trp Glu Val Ser Ser Glu Asn Gly
                180                 185                 190 aac tat gac tat tta atg tat gct gat gtt gac tac gac cac cct gat    963
Asn Tyr Asp Tyr Leu Met Tyr Ala Asp Val Asp Tyr Asp His Pro Asp
            195                 200                 205 gtc gtg gca gag aca aaa aaa tgg ggt atc tgg tat gcg aat gaa ctg    1011
Val Val Ala Glu Thr Lys Lys Trp Gly Ile Trp Tyr Ala Asn Glu Leu
        210                 215                 220 tca tta gac ggc ttc cgt att gat gcc gcc aaa cat att aaa ttt tca   1059
Ser Leu Asp Gly Phe Arg Ile Asp Ala Ala Lys His Ile Lys Phe Ser
        225                 230                 235 ttt ctg cgt gat tgg gtt cag gcg gtc aga cag gcg acg gga aaa gaa   1107
Phe Leu Arg Asp Trp Val Gln Ala Val Arg Gln Ala Thr Gly Lys Glu
240                 245                 250                 255 atg ttt acg gtt gcg gag tat tgg cag aat aat gcc ggg aaa ctc gaa   1155
Met Phe Thr Val Ala Glu Tyr Trp Gln Asn Asn Ala Gly Lys Leu Glu
                260                 265                 270
```

```
aac tac ttg aat aaa aca agc ttt aat caa tcc gtg ttt gat gtt ccg    1203
Asn Tyr Leu Asn Lys Thr Ser Phe Asn Gln Ser Val Phe Asp Val Pro
        275                 280                 285 ctt cat ttc aat tta cag gcg gct tcc tca caa gga ggc gga tat gat    1251
Leu His Phe Asn Leu Gln Ala Ala Ser Ser Gln Gly Gly Gly Tyr Asp
        290                 295                 300 atg agg cgt ttg ctg gac ggt acc gtt gtg tcc agg cat ccg gaa aag    1299
Met Arg Arg Leu Leu Asp Gly Thr Val Val Ser Arg His Pro Glu Lys
        305                 310                 315 gcg gtt aca ttt gtt gaa aat cat gac aca cag ccg gga cag tca ttg    1347
Ala Val Thr Phe Val Glu Asn His Asp Thr Gln Pro Gly Gln Ser Leu
320                 325                 330                 335 gaa tcg aca gtc caa act tgg ttt aaa ccg ctt gca tac gcc ttt att    1395
Glu Ser Thr Val Gln Thr Trp Phe Lys Pro Leu Ala Tyr Ala Phe Ile
                340                 345                 350 ttg aca aga gaa tcc ggt tat cct cag gtg ttc tat ggg gat atg tac    1443
Leu Thr Arg Glu Ser Gly Tyr Pro Gln Val Phe Tyr Gly Asp Met Tyr
                355                 360                 365 ggg aca aaa ggg aca tcg cca aag gaa att ccc tca ctg aaa gat aat    1491
Gly Thr Lys Gly Thr Ser Pro Lys Glu Ile Pro Ser Leu Lys Asp Asn
                370                 375                 380 ata gag ccg att tta aaa gcg cgt aag gag tac gca tac ggg ccc cag    1539
Ile Glu Pro Ile Leu Lys Ala Arg Lys Glu Tyr Ala Tyr Gly Pro Gln
385                 390                 395 cac gat tat att gac cac ccg gat gtg atc gga tgg acg agg gaa ggt    1587
His Asp Tyr Ile Asp His Pro Asp Val Ile Gly Trp Thr Arg Glu Gly
400                 405                 410                 415 gac agc tcc gcc gcc aaa tca ggt ttg gcc gct tta atc acg gac gga    1635
Asp Ser Ser Ala Ala Lys Ser Gly Leu Ala Ala Leu Ile Thr Asp Gly
                420                 425                 430 ccc ggc gga tca aag cgg atg tat gcc ggc ctg aaa aat gcc ggc gag    1683
Pro Gly Gly Ser Lys Arg Met Tyr Ala Gly Leu Lys Asn Ala Gly Glu
                435                 440                 445 aca tgg tat gac ata acg ggc aac cgt tca gat act gta aaa atc gga    1731
Thr Trp Tyr Asp Ile Thr Gly Asn Arg Ser Asp Thr Val Lys Ile Gly
                450                 455                 460 tct gac ggc tgg gga gag ttt cat gta aac gat ggg tcc gtc tcc att    1779
Ser Asp Gly Trp Gly Glu Phe His Val Asn Asp Gly Ser Val Ser Ile
465                 470                 475 tat gtt cag aaa taaggtaata aaaaaacacc tccaagctga gtgcgggtat        1831
Tyr Val Gln Lys
480 cagcttggag gtgcgtttat tttttcagcc gtatgacaag gtcggcatca ggtgtgacaa    1891 atacggtatg ctggctgtca taggtgacaa atccgggttt tgcgccgttt ggcttttttca   1951 catgtctgat ttttgtataa tcaacaggca cggagccgga atctttcgcc ttggaaaaat    2011 aagcggcgat cgtagctgct tccaatatgg attgttcatc gggatcgctg cttttaatca    2071 caacgtggga tcc                                                       2084

<210> SEQ ID NO 4
<211> LENGTH: 514
<212> TYPE: PRT
<213> ORGANISM: Bacillus amyloliquefaciens

<400> SEQUENCE: 4

Met Ile Gln Lys Arg Lys Arg Thr Val Ser Phe Arg Leu Val Leu Met
        -30                 -25                 -20

Cys Thr Leu Leu Phe Val Ser Leu Pro Ile Thr Lys Thr Ser Ala Val
-15                 -10                  -5                  -1  1
```

```
Asn Gly Thr Leu Met Gln Tyr Phe Glu Trp Tyr Thr Pro Asn Asp Gly
                  5                  10                 15
Gln His Trp Lys Arg Leu Gln Asn Asp Ala Glu His Leu Ser Asp Ile
             20                  25                 30
Gly Ile Thr Ala Val Trp Ile Pro Ala Tyr Lys Gly Leu Ser Gln
 35                  40                  45
Ser Asp Asn Gly Tyr Gly Pro Tyr Asp Leu Tyr Asp Leu Gly Glu Phe
 50              55                  60                      65
Gln Gln Lys Gly Thr Val Arg Thr Lys Tyr Gly Thr Lys Ser Glu Leu
             70                  75                  80
Gln Asp Ala Ile Gly Ser Leu His Ser Arg Asn Val Gln Val Tyr Gly
             85                  90                  95
Asp Val Val Leu Asn His Lys Ala Gly Ala Asp Ala Thr Glu Asp Val
            100                 105                 110
Thr Ala Val Glu Val Asn Pro Ala Asn Arg Asn Gln Glu Thr Ser Glu
            115                 120                 125
Glu Tyr Gln Ile Lys Ala Trp Thr Asp Phe Arg Phe Pro Gly Arg Gly
130                 135                 140                 145
Asn Thr Tyr Ser Asp Phe Lys Trp His Trp Tyr His Phe Asp Gly Ala
                150                 155                 160
Asp Trp Asp Glu Ser Arg Lys Ile Ser Arg Ile Phe Lys Phe Arg Gly
                165                 170                 175
Glu Gly Lys Ala Trp Asp Trp Glu Val Ser Ser Glu Asn Gly Asn Tyr
        180                 185                 190
Asp Tyr Leu Met Tyr Ala Asp Val Asp Tyr Asp His Pro Asp Val Val
        195                 200                 205
Ala Glu Thr Lys Lys Trp Gly Ile Trp Tyr Ala Asn Glu Leu Ser Leu
210                 215                 220                 225
Asp Gly Phe Arg Ile Asp Ala Ala Lys His Ile Lys Phe Ser Phe Leu
                230                 235                 240
Arg Asp Trp Val Gln Ala Val Arg Gln Ala Thr Gly Lys Glu Met Phe
                245                 250                 255
Thr Val Ala Glu Tyr Trp Gln Asn Asn Ala Gly Lys Leu Glu Asn Tyr
        260                 265                 270
Leu Asn Lys Thr Ser Phe Asn Gln Ser Val Phe Asp Val Pro Leu His
275                 280                 285
Phe Asn Leu Gln Ala Ala Ser Ser Gln Gly Gly Gly Tyr Asp Met Arg
290                 295                 300                 305
Arg Leu Leu Asp Gly Thr Val Val Ser Arg His Pro Glu Lys Ala Val
                310                 315                 320
Thr Phe Val Glu Asn His Asp Thr Gln Pro Gly Gln Ser Leu Glu Ser
                325                 330                 335
Thr Val Gln Thr Trp Phe Lys Pro Leu Ala Tyr Ala Phe Ile Leu Thr
        340                 345                 350
Arg Glu Ser Gly Tyr Pro Gln Val Phe Tyr Gly Asp Met Tyr Gly Thr
        355                 360                 365
Lys Gly Thr Ser Pro Lys Glu Ile Pro Ser Leu Lys Asp Asn Ile Glu
370                 375                 380                 385
Pro Ile Leu Lys Ala Arg Lys Glu Tyr Ala Tyr Gly Pro Gln His Asp
                390                 395                 400
Tyr Ile Asp His Pro Asp Val Ile Gly Trp Thr Arg Glu Gly Asp Ser
                405                 410                 415
Ser Ala Ala Lys Ser Gly Leu Ala Ala Leu Ile Thr Asp Gly Pro Gly
        420                 425                 430
```

-continued

```
Gly Ser Lys Arg Met Tyr Ala Gly Leu Lys Asn Ala Gly Glu Thr Trp
    435                 440                 445

Tyr Asp Ile Thr Gly Asn Arg Ser Asp Thr Val Lys Ile Gly Ser Asp
450                 455                 460                 465

Gly Trp Gly Glu Phe His Val Asn Asp Gly Ser Val Ser Ile Tyr Val
                470                 475                 480

Gln Lys

<210> SEQ ID NO 5
<211> LENGTH: 1814
<212> TYPE: DNA
<213> ORGANISM: Bacillus stearothermophilus
<220> FEATURE:
<221> NAME/KEY: CDS
<222> LOCATION: (156)..(1802)
<220> FEATURE:
<221> NAME/KEY: sig_peptide
<222> LOCATION: (156)..(257)
<220> FEATURE:
<221> NAME/KEY: mat_peptide
<222> LOCATION: (258)..(1802)

<400> SEQUENCE: 5
aaattcgata ttgaaaacga ttacaaataa aaattataat agacgtaaac gttcgagggt      60
ttgctccctt tttactcttt ttatgcaatc gtttccctta attttttgga agccaaaccg     120
tcgaatgtaa catttgatta agggggaagg gcatt gtg cta acg ttt cac cgc        173
                                      Val Leu Thr Phe His Arg
                                      -34             -30 atc att cga aaa gga tgg atg ttc ctg ctc gcg ttt ttg ctc act gtc        221
Ile Ile Arg Lys Gly Trp Met Phe Leu Leu Ala Phe Leu Leu Thr Val
        -25                 -20                 -15 tcg ctg ttc tgc cca aca gga cag ccc gcc aag gct gcc gca ccg ttt        269
Ser Leu Phe Cys Pro Thr Gly Gln Pro Ala Lys Ala Ala Ala Pro Phe
        -10                  -5                  -1  1 aac ggc acc atg atg cag tat ttt gaa tgg tac ttg ccg gat gat ggc        317
Asn Gly Thr Met Met Gln Tyr Phe Glu Trp Tyr Leu Pro Asp Asp Gly
5                   10                  15                  20 acg tta tgg acc aaa gtg gcc aat gaa gcc aac aac tta tcc agc ctt        365
Thr Leu Trp Thr Lys Val Ala Asn Glu Ala Asn Asn Leu Ser Ser Leu
            25                  30                  35 ggc atc acc gct ctt tgg ctg ccg ccc gct tac aaa gga aca agc cgc        413
Gly Ile Thr Ala Leu Trp Leu Pro Pro Ala Tyr Lys Gly Thr Ser Arg
        40                  45                  50 agc gac gta ggg tac gga gta tac gac ttg tat gac ctc ggc gaa ttc        461
Ser Asp Val Gly Tyr Gly Val Tyr Asp Leu Tyr Asp Leu Gly Glu Phe
    55                  60                  65 aat caa aaa ggg acc gtc cgc aca aaa tac gga aca aaa gct caa tat        509
Asn Gln Lys Gly Thr Val Arg Thr Lys Tyr Gly Thr Lys Ala Gln Tyr
70                  75                  80 ctt caa gcc att caa gcc gcc cac gcc gct gga atg caa gtg tac gcc        557
Leu Gln Ala Ile Gln Ala Ala His Ala Ala Gly Met Gln Val Tyr Ala
85                  90                  95                  100 gat gtc gtg ttc gac cat aaa ggc ggc gct gac ggc acg gaa tgg gtg        605
Asp Val Val Phe Asp His Lys Gly Gly Ala Asp Gly Thr Glu Trp Val
                105                 110                 115 gac gcc gtc gaa gtc aat ccg tcc gac cgc aac caa gaa atc tcg ggc        653
Asp Ala Val Glu Val Asn Pro Ser Asp Arg Asn Gln Glu Ile Ser Gly
            120                 125                 130 acc tat caa atc caa gca tgg acg aaa ttt gat ttt ccc ggg cgg ggc        701
Thr Tyr Gln Ile Gln Ala Trp Thr Lys Phe Asp Phe Pro Gly Arg Gly
        135                 140                 145
```

```
aac acc tac tcc agc ttt aag tgg cgc tgg tac cat ttt gac ggc gtt      749
Asn Thr Tyr Ser Ser Phe Lys Trp Arg Trp Tyr His Phe Asp Gly Val
        150             155                 160 gat tgg gac gaa agc cga aaa ttg agc cgc att tac aaa ttc cgc ggc      797
Asp Trp Asp Glu Ser Arg Lys Leu Ser Arg Ile Tyr Lys Phe Arg Gly
165             170                 175                 180 atc ggc aaa gcg tgg gat tgg gaa gta gac acg gaa aac gga aac tat      845
Ile Gly Lys Ala Trp Asp Trp Glu Val Asp Thr Glu Asn Gly Asn Tyr
                    185                 190                 195 gac tac tta atg tat gcc gac ctt gat atg gat cat ccc gaa gtc gtg      893
Asp Tyr Leu Met Tyr Ala Asp Leu Asp Met Asp His Pro Glu Val Val
                200                 205                 210 acc gag ctg aaa aac tgg ggg aaa tgg tat gtc aac aca acg aac att      941
Thr Glu Leu Lys Asn Trp Gly Lys Trp Tyr Val Asn Thr Thr Asn Ile
            215                 220                 225 gat ggg ttc cgg ctt gat gcc gtc aag cat att aag ttc agt ttt ttt      989
Asp Gly Phe Arg Leu Asp Ala Val Lys His Ile Lys Phe Ser Phe Phe
        230                 235                 240 cct gat tgg ttg tcg tat gtg cgt tct cag act ggc aag ccg cta ttt     1037
Pro Asp Trp Leu Ser Tyr Val Arg Ser Gln Thr Gly Lys Pro Leu Phe
245                 250                 255                 260 acc gtc ggg gaa tat tgg agc tat gac atc aac aag ttg cac aat tac     1085
Thr Val Gly Glu Tyr Trp Ser Tyr Asp Ile Asn Lys Leu His Asn Tyr
                    265                 270                 275 att acg aaa aca gac gga acg atg tct ttg ttt gat gcc ccg tta cac     1133
Ile Thr Lys Thr Asp Gly Thr Met Ser Leu Phe Asp Ala Pro Leu His
                280                 285                 290 aac aaa ttt tat acc gct tcc aaa tca ggg ggc gca ttt gat atg cgc     1181
Asn Lys Phe Tyr Thr Ala Ser Lys Ser Gly Gly Ala Phe Asp Met Arg
            295                 300                 305 acg tta atg acc aat act ctc atg aaa gat caa ccg aca ttg gcc gtc     1229
Thr Leu Met Thr Asn Thr Leu Met Lys Asp Gln Pro Thr Leu Ala Val
        310                 315                 320 acc ttc gtt gat aat cat gac acc gaa ccc ggc caa gcg ctg cag tca     1277
Thr Phe Val Asp Asn His Asp Thr Glu Pro Gly Gln Ala Leu Gln Ser
325                 330                 335                 340 tgg gtc gac cca tgg ttc aaa ccg ttg gct tac gcc ttt att cta act     1325
Trp Val Asp Pro Trp Phe Lys Pro Leu Ala Tyr Ala Phe Ile Leu Thr
                    345                 350                 355 cgg cag gaa gga tac ccg tgc gtc ttt tat ggt gac tat tat ggc att     1373
Arg Gln Glu Gly Tyr Pro Cys Val Phe Tyr Gly Asp Tyr Tyr Gly Ile
                360                 365                 370 cca caa tat aac att cct tcg ctg aaa agc aaa atc gat ccg ctc ctc     1421
Pro Gln Tyr Asn Ile Pro Ser Leu Lys Ser Lys Ile Asp Pro Leu Leu
            375                 380                 385 atc gcg cgc agg gat tat gct tac gga acg caa cat gat tat ctt gat     1469
Ile Ala Arg Arg Asp Tyr Ala Tyr Gly Thr Gln His Asp Tyr Leu Asp
        390                 395                 400 cac tcc gac atc atc ggg tgg aca agg gaa ggg ggc act gaa aaa cca     1517
His Ser Asp Ile Ile Gly Trp Thr Arg Glu Gly Gly Thr Glu Lys Pro
405                 410                 415                 420 gga tcc gga ctg gcc gca ctg atc acc gat ggg ccg gga gga agc aaa     1565
Gly Ser Gly Leu Ala Ala Leu Ile Thr Asp Gly Pro Gly Gly Ser Lys
                    425                 430                 435 tgg atg tac gtt ggc aaa caa cac gct gga aaa gtg ttc tat gac ctt     1613
Trp Met Tyr Val Gly Lys Gln His Ala Gly Lys Val Phe Tyr Asp Leu
                440                 445                 450 acc ggc aac cgg agt gac acc gtc acc atc aac agt gat gga tgg ggg     1661
Thr Gly Asn Arg Ser Asp Thr Val Thr Ile Asn Ser Asp Gly Trp Gly
            455                 460                 465
```

-continued

```
gaa ttc aaa gtc aat ggc ggt tcg gtt tcg gtt tgg gtt cct aga aaa    1709
Glu Phe Lys Val Asn Gly Gly Ser Val Ser Val Trp Val Pro Arg Lys
470                 475                 480 acg acc gtt tct acc atc gct cgg ccg atc aca acc cga ccg tgg act    1757
Thr Thr Val Ser Thr Ile Ala Arg Pro Ile Thr Thr Arg Pro Trp Thr
485                 490                 495                 500 ggt gaa ttc gtc cgt tgg acc gaa cca cgg ttg gtg gca tgg cct        1802
Gly Glu Phe Val Arg Trp Thr Glu Pro Arg Leu Val Ala Trp Pro
            505                 510                 515 tgatgcctgc ga                                                      1814
```

<210> SEQ ID NO 6
<211> LENGTH: 549
<212> TYPE: PRT
<213> ORGANISM: Bacillus stearothermophilus

<400> SEQUENCE: 6

```
Val Leu Thr Phe His Arg Ile Ile Arg Lys Gly Trp Met Phe Leu Leu
            -30                 -25                 -20

Ala Phe Leu Leu Thr Val Ser Leu Phe Cys Pro Thr Gly Gln Pro Ala
        -15                 -10                  -5

Lys Ala Ala Ala Pro Phe Asn Gly Thr Met Met Gln Tyr Phe Glu Trp
 -1   1               5                  10

Tyr Leu Pro Asp Asp Gly Thr Leu Trp Thr Lys Val Ala Asn Glu Ala
 15                  20                  25                  30

Asn Asn Leu Ser Ser Leu Gly Ile Thr Ala Leu Trp Leu Pro Pro Ala
                 35                  40                  45

Tyr Lys Gly Thr Ser Arg Ser Asp Val Gly Tyr Gly Val Tyr Asp Leu
                 50                  55                  60

Tyr Asp Leu Gly Glu Phe Asn Gln Lys Gly Thr Val Arg Thr Lys Tyr
 65                  70                  75

Gly Thr Lys Ala Gln Tyr Leu Gln Ala Ile Gln Ala Ala His Ala Ala
                 80                  85                  90

Gly Met Gln Val Tyr Ala Asp Val Val Phe Asp His Lys Gly Gly Ala
 95                 100                 105                 110

Asp Gly Thr Glu Trp Val Asp Ala Val Glu Val Asn Pro Ser Asp Arg
                115                 120                 125

Asn Gln Glu Ile Ser Gly Thr Tyr Gln Ile Gln Ala Trp Thr Lys Phe
                130                 135                 140

Asp Phe Pro Gly Arg Gly Asn Thr Tyr Ser Ser Phe Lys Trp Arg Trp
                145                 150                 155

Tyr His Phe Asp Gly Val Asp Trp Asp Glu Ser Arg Lys Leu Ser Arg
                160                 165                 170

Ile Tyr Lys Phe Arg Gly Ile Gly Lys Ala Trp Asp Trp Glu Val Asp
175                 180                 185                 190

Thr Glu Asn Gly Asn Tyr Asp Tyr Leu Met Tyr Ala Asp Leu Asp Met
                195                 200                 205

Asp His Pro Glu Val Val Thr Glu Leu Lys Asn Trp Gly Lys Trp Tyr
                210                 215                 220

Val Asn Thr Thr Asn Ile Asp Gly Phe Arg Leu Asp Ala Val Lys His
                225                 230                 235

Ile Lys Phe Ser Phe Phe Pro Asp Trp Leu Ser Tyr Val Arg Ser Gln
                240                 245                 250

Thr Gly Lys Pro Leu Phe Thr Val Gly Glu Tyr Trp Ser Tyr Asp Ile
255                 260                 265                 270
```

Asn Lys Leu His Asn Tyr Ile Thr Lys Thr Asp Gly Thr Met Ser Leu
            275                 280                 285

Phe Asp Ala Pro Leu His Asn Lys Phe Tyr Thr Ala Ser Lys Ser Gly
        290                 295                 300

Gly Ala Phe Asp Met Arg Thr Leu Met Thr Asn Thr Leu Met Lys Asp
    305                 310                 315

Gln Pro Thr Leu Ala Val Thr Phe Val Asp Asn His Asp Thr Glu Pro
320                 325                 330

Gly Gln Ala Leu Gln Ser Trp Val Asp Pro Trp Phe Lys Pro Leu Ala
335                 340                 345                 350

Tyr Ala Phe Ile Leu Thr Arg Gln Glu Gly Tyr Pro Cys Val Phe Tyr
            355                 360                 365

Gly Asp Tyr Tyr Gly Ile Pro Gln Tyr Asn Ile Pro Ser Leu Lys Ser
        370                 375                 380

Lys Ile Asp Pro Leu Leu Ile Ala Arg Arg Asp Tyr Ala Tyr Gly Thr
    385                 390                 395

Gln His Asp Tyr Leu Asp His Ser Asp Ile Ile Gly Trp Thr Arg Glu
400                 405                 410

Gly Gly Thr Glu Lys Pro Gly Ser Gly Leu Ala Ala Leu Ile Thr Asp
415                 420                 425                 430

Gly Pro Gly Gly Ser Lys Trp Met Tyr Val Gly Lys Gln His Ala Gly
            435                 440                 445

Lys Val Phe Tyr Asp Leu Thr Gly Asn Arg Ser Asp Thr Val Thr Ile
        450                 455                 460

Asn Ser Asp Gly Trp Gly Glu Phe Lys Val Asn Gly Gly Ser Val Ser
    465                 470                 475

Val Trp Val Pro Arg Lys Thr Thr Val Ser Thr Ile Ala Arg Pro Ile
480                 485                 490

Thr Thr Arg Pro Trp Thr Gly Glu Phe Val Arg Trp Thr Glu Pro Arg
495                 500                 505                 510

Leu Val Ala Trp Pro
            515

<210> SEQ ID NO 7
<211> LENGTH: 31
<212> TYPE: DNA
<213> ORGANISM: Artificial sequence
<220> FEATURE:
<223> OTHER INFORMATION: Synthetic construct

<400> SEQUENCE: 7
ggtcgtaggc accgtagccc caatccgctt g                                  31

<210> SEQ ID NO 8
<211> LENGTH: 36
<212> TYPE: DNA
<213> ORGANISM: Artificial sequence
<220> FEATURE:
<223> OTHER INFORMATION: Synthetic construct

<400> SEQUENCE: 8
ggtcgtaggc accgtagccc caatcccatt ggctcg                             36

<210> SEQ ID NO 9
<211> LENGTH: 28
<212> TYPE: DNA
<213> ORGANISM: Artificial sequence
<220> FEATURE:
<223> OTHER INFORMATION: Synthetic construct

<400> SEQUENCE: 9
ctgtgactgg tgagtactca accaagtc                                           28

<210> SEQ ID NO 10
<211> LENGTH: 478
<212> TYPE: PRT
<213> ORGANISM: Aspergillus oryzae

<400> SEQUENCE: 10

```
Ala Thr Pro Ala Asp Trp Arg Ser Gln Ser Ile Tyr Phe Leu Leu Thr
 1               5                  10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285

Leu Gly Thr Phe Val Glu Asn His Asp Asn Pro Arg Phe Ala Ser Tyr
    290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
        355                 360                 365
```

```
Arg Asn Tyr Ala Ile Ser Lys Asp Thr Gly Phe Val Thr Tyr Lys Asn
        370                 375                 380

Trp Pro Ile Tyr Lys Asp Asp Ile Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
                420                 425                 430

Gln Leu Thr Glu Val Ile Gly Cys Thr Thr Val Thr Val Gly Ser Asp
            435                 440                 445

Gly Asn Val Pro Val Pro Met Ala Gly Gly Leu Pro Arg Val Leu Tyr
        450                 455                 460

Pro Thr Glu Lys Leu Ala Gly Ser Lys Ile Cys Ser Ser Ser
465                 470                 475
```

```
<210> SEQ ID NO 11
<211> LENGTH: 1458
<212> TYPE: DNA
<213> ORGANISM: Unknown
<220> FEATURE:
<223> OTHER INFORMATION: Bacillus species
<220> FEATURE:
<221> NAME/KEY: CDS
<222> LOCATION: (1)..(1455)

<400> SEQUENCE: 11
```

| | | | | | | | | | | | | | | | | |
|---|---|---|---|---|---|---|---|---|---|---|---|---|---|---|---|---|
| cat cat aat gga aca aat ggt act atg atg caa tat ttc gaa tgg tat | | | | | | | | | | | | | | | | 48 |
| His His Asn Gly Thr Asn Gly Thr Met Met Gln Tyr Phe Glu Trp Tyr | | | | | | | | | | | | | | | | |
| 1               5                   10                  15 | | | | | | | | | | | | | | | | |

```
ttg cca aat gac ggg aat cat tgg aac agg ttg agg gat gac gca gct      96
Leu Pro Asn Asp Gly Asn His Trp Asn Arg Leu Arg Asp Asp Ala Ala
                20                  25                  30 aac tta aag agt aaa ggg ata aca gct gta tgg atc cca cct gca tgg     144
Asn Leu Lys Ser Lys Gly Ile Thr Ala Val Trp Ile Pro Pro Ala Trp
            35                  40                  45 aag ggg act tcc cag aat gat gta ggt tat gga gcc tat gat tta tat     192
Lys Gly Thr Ser Gln Asn Asp Val Gly Tyr Gly Ala Tyr Asp Leu Tyr
        50                  55                  60 gat ctt gga gag ttt aac cag aag ggg acg gtt cgt aca aaa tat gga     240
Asp Leu Gly Glu Phe Asn Gln Lys Gly Thr Val Arg Thr Lys Tyr Gly
 65                 70                  75                  80 aca cgc aac cag cta cag gct gcg gtg acc tct tta aaa aat aac ggc     288
Thr Arg Asn Gln Leu Gln Ala Ala Val Thr Ser Leu Lys Asn Asn Gly
                85                  90                  95 att cag gta tat ggt gat gtc gtc atg aat cat aaa ggt gga gca gat     336
Ile Gln Val Tyr Gly Asp Val Val Met Asn His Lys Gly Gly Ala Asp
            100                 105                 110 ggt acg gaa att gta aat gcg gta gaa gtg aat cgg agc aac cga aac     384
Gly Thr Glu Ile Val Asn Ala Val Glu Val Asn Arg Ser Asn Arg Asn
        115                 120                 125 cag gaa acc tca gga gag tat gca ata gaa gcg tgg aca aag ttt gat     432
Gln Glu Thr Ser Gly Glu Tyr Ala Ile Glu Ala Trp Thr Lys Phe Asp
    130                 135                 140 ttt cct gga aga gga aat aac cat tcc agc ttt aag tgg cgc tgg tat     480
Phe Pro Gly Arg Gly Asn Asn His Ser Ser Phe Lys Trp Arg Trp Tyr
145                 150                 155                 160 cat ttt gat ggg aca gat tgg gat cag tca cgc cag ctt caa aac aaa     528
His Phe Asp Gly Thr Asp Trp Asp Gln Ser Arg Gln Leu Gln Asn Lys
                165                 170                 175 ata tat aaa ttc agg gga aca ggc aag gcc tgg gac tgg gaa gtc gat     576
```

```
Ile Tyr Lys Phe Arg Gly Thr Gly Lys Ala Trp Asp Trp Glu Val Asp
            180                 185                 190 aca gag aat ggc aac tat gac tat ctt atg tat gca gac gtg gat atg         624
Thr Glu Asn Gly Asn Tyr Asp Tyr Leu Met Tyr Ala Asp Val Asp Met
        195                 200                 205 gat cac cca gaa gta ata cat gaa ctt aga aac tgg gga gtg tgg tat         672
Asp His Pro Glu Val Ile His Glu Leu Arg Asn Trp Gly Val Trp Tyr
    210                 215                 220 acg aat aca ctg aac ctt gat gga ttt aga ata gat gca gtg aaa cat         720
Thr Asn Thr Leu Asn Leu Asp Gly Phe Arg Ile Asp Ala Val Lys His
225                 230                 235                 240 ata aaa tat agc ttt acg aga gat tgg ctt aca cat gtg cgt aac acc         768
Ile Lys Tyr Ser Phe Thr Arg Asp Trp Leu Thr His Val Arg Asn Thr
                245                 250                 255 aca ggt aaa cca atg ttt gca gtg gct gag ttt tgg aaa aat gac ctt         816
Thr Gly Lys Pro Met Phe Ala Val Ala Glu Phe Trp Lys Asn Asp Leu
            260                 265                 270 ggt gca att gaa aac tat ttg aat aaa aca agt tgg aat cac tcg gtg         864
Gly Ala Ile Glu Asn Tyr Leu Asn Lys Thr Ser Trp Asn His Ser Val
        275                 280                 285 ttt gat gtt cct ctc cac tat aat ttg tac aat gca tct aat agc ggt         912
Phe Asp Val Pro Leu His Tyr Asn Leu Tyr Asn Ala Ser Asn Ser Gly
    290                 295                 300 ggt tat tat gat atg aga aat att tta aat ggt tct gtg gtg caa aaa         960
Gly Tyr Tyr Asp Met Arg Asn Ile Leu Asn Gly Ser Val Val Gln Lys
305                 310                 315                 320 cat cca aca cat gcc gtt act ttt gtt gat aac cat gat tct cag ccc        1008
His Pro Thr His Ala Val Thr Phe Val Asp Asn His Asp Ser Gln Pro
                325                 330                 335 ggg gaa gca ttg gaa tcc ttt gtt caa caa tgg ttt aaa cca ctt gca        1056
Gly Glu Ala Leu Glu Ser Phe Val Gln Gln Trp Phe Lys Pro Leu Ala
            340                 345                 350 tat gca ttg gtt ctg aca agg gaa caa ggt tat cct tcc gta ttt tat        1104
Tyr Ala Leu Val Leu Thr Arg Glu Gln Gly Tyr Pro Ser Val Phe Tyr
        355                 360                 365 ggg gat tac tac ggt atc cca acc cat ggt gtt ccg gct atg aaa tct        1152
Gly Asp Tyr Tyr Gly Ile Pro Thr His Gly Val Pro Ala Met Lys Ser
    370                 375                 380 aaa ata gac cct ctt ctg cag gca cgt caa act ttt gcc tat ggt acg        1200
Lys Ile Asp Pro Leu Leu Gln Ala Arg Gln Thr Phe Ala Tyr Gly Thr
385                 390                 395                 400 cag cat gat tac ttt gat cat cat gat att atc ggt tgg aca aga gag        1248
Gln His Asp Tyr Phe Asp His His Asp Ile Ile Gly Trp Thr Arg Glu
                405                 410                 415 gga aat agc tcc cat cca aat tca ggc ctt gcc acc att atg tca gat        1296
Gly Asn Ser Ser His Pro Asn Ser Gly Leu Ala Thr Ile Met Ser Asp
            420                 425                 430 ggt cca ggt ggt aac aaa tgg atg tat gtg ggg aaa aat aaa gcg gga        1344
Gly Pro Gly Gly Asn Lys Trp Met Tyr Val Gly Lys Asn Lys Ala Gly
        435                 440                 445 caa gtt tgg aga gat att acc gga aat agg aca ggc acc gtc aca att        1392
Gln Val Trp Arg Asp Ile Thr Gly Asn Arg Thr Gly Thr Val Thr Ile
    450                 455                 460 aat gca gac gga tgg ggt aat ttc tct gtt aat gga ggg tcc gtt tcg        1440
Asn Ala Asp Gly Trp Gly Asn Phe Ser Val Asn Gly Gly Ser Val Ser
465                 470                 475                 480 gtt tgg gtg aag caa taa                                                1458
Val Trp Val Lys Gln
                485
```

<210> SEQ ID NO 12
<211> LENGTH: 485
<212> TYPE: PRT
<213> ORGANISM: Unknown
<220> FEATURE:
<223> OTHER INFORMATION: Synthetic Construct

<400> SEQUENCE: 12

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380
```

```
Lys Ile Asp Pro Leu Leu Gln Ala Arg Gln Thr Phe Ala Tyr Gly Thr
385                 390                 395                 400

Gln His Asp Tyr Phe Asp His Asp Ile Ile Gly Trp Thr Arg Glu
            405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
            435                 440                 445

Gln Val Trp Arg Asp Ile Thr Gly Asn Arg Thr Gly Thr Val Thr Ile
            450                 455                 460

Asn Ala Asp Gly Trp Gly Asn Phe Ser Val Asn Gly Ser Val Ser
465                 470                 475                 480

Val Trp Val Lys Gln
            485

<210> SEQ ID NO 13
<211> LENGTH: 483
<212> TYPE: PRT
<213> ORGANISM: Artificial sequence
<220> FEATURE:
<223> OTHER INFORMATION: Synthetic construct

<400> SEQUENCE: 13

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
        50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
        130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255
```

-continued

```
Phe Thr Val Ala Glu Tyr Trp Gln Asn Asn Ala Gly Lys Leu Glu Asn
            260                 265                 270
Tyr Leu Asn Lys Thr Ser Phe Asn Gln Ser Val Phe Asp Val Pro Leu
            275                 280                 285
His Phe Asn Leu Gln Ala Ala Ser Ser Gln Gly Gly Gly Tyr Asp Met
            290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
            355                 360                 365
Thr Lys Gly Asp Ser Gln Arg Glu Ile Pro Ala Leu Lys His Lys Ile
            370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
            420                 425                 430
Gly Gly Ala Lys Arg Met Tyr Val Gly Arg Gln Asn Ala Gly Glu Thr
            435                 440                 445
Trp His Asp Ile Thr Gly Asn Arg Ser Glu Pro Val Val Ile Asn Ser
    450                 455                 460
Glu Gly Trp Gly Glu Phe His Val Asn Gly Gly Ser Val Ser Ile Tyr
465                 470                 475                 480
Val Gln Arg
```

α-AMYLASE MUTANTS

CROSS-REFERENCE TO RELATED APPLICATIONS

This application is a divisional of U.S. application Ser. No. 11/064,196 filed on Feb. 22, 2005, now U.S. Pat. No. 7,378,264, which is a continuation of U.S. application Ser. No. 10/184,771, filed on Jun. 28, 2002, now abandoned, which is a continuation of U.S. application Ser. No. 09/636,252, filed on Aug. 10, 2000, now U.S. Pat. No. 6,440,716, which is a continuation of Ser. No. 09/327,563, filed on Jun. 8, 1999, now U.S. Pat. No. 7,115,409, which is continuation of U.S. application Ser. No. 08/683,838, filed on Jul. 18, 1996, now U.S. Pat. No. 6,022,724, which is a continuation-in-part of U.S. application Ser. No. 08/600,908, filed on Feb. 13, 1996, now U.S. Pat. No. 5,989,169, which is a 35 U.S.C. 371 national application of international application no. PCT/DK96/00057, filed on Feb. 5, 1996, and claims priority under 35 U.S.C. 119 of Danish applications 0128/95, filed on Feb. 3, 1995, 1192/95, filed on Oct. 23, 1995, and 1256/95, filed on Nov. 10, 1995, the contents of which are fully incorporated herein by reference.

FIELD OF THE INVENTION

The present invention relates to a novel method of designing α-amylase mutants with predetermined properties, which method is based on the hitherto unknown three-dimensional structure of bacterial α-amylases.

BACKGROUND OF THE INVENTION

α-Amylases (α-1,4 glucan-4-glucanohydrolase, EC 3.2.1.1) constitute a group of enzymes which is capable of hydrolyzing starch and other linear and branched 1,4-glucosidic oligo- and polysaccharides. Almost all α-amylases studied have a few conserved regions with approximately the same length and spacing. One of these regions resembles the Ca2+ binding site of calmodulin and the others are thought to be necessary for the active centre and/or binding of the substrate.

While the amino acid sequence and thus primary structure of a large number of α-amylases are known, it has proved very difficult to determine the three-dimensional structure of all α-amylases. The three-dimensional structure can be determined by X-ray crystallographic analysis of α-amylase crystals, but it has proven difficult to obtain α-amylase crystals suitable for actually solving the structure.

Until now the three-dimensional structure of only a few α-amylases have been determined at high resolution. These include the structure of the *Aspergillus oryzae* TAKA α-amylase (Swift et al., 1991), the *Aspergillus niger* acid amylase (Brady et al, 1991), the structure of pig pancreatic α-amylase (Qian et al., 1993), and the barley alpha-amylase (Kadziola et al. 1994, Journal of Molecular Biology 239: 104-121, A. Kadziola, Thesis, Dept of Chemistry, U. of Copenhagen, Denmark). Furthermore, the three-dimensional structure of a *Bacillus circulans* cyclodextrin glycosyltransferase (CG-Tase) is known (Klein et al., 1992) (Lawson et al., 1994). The CGTase catalyzes the same type of reactions as α-amylases and exhibits some structural resemblance with α-amylases.

Furthermore, crystallization and preliminary X-ray studies of *B. subtilis* α-amylases have been described (Chang et al. (1992) and Mizuno et al. (1993)). No final *B. subtilis* structure has been reported. Analogously, the preparation of *B. licheniformis* α-amylase crystals has been reported (Suzuki et al. (1990), but no subsequent report on X-ray crystallographic analysis or three-dimensional structure are available.

Several research teams have attempted to build three-dimensional structures on the basis of the above known α-amylase structures. For instance, Vihinen et al. (J. Biochem. 107, 267-272, 1990), disclose the modelling (or computer simulation) of a three-dimensional structure of the *Bacillus stearothermophilus* α-amylase on the basis of the TAKA amylase structure. The model was used to investigate hypothetical structural consequences of various site-directed mutations of the *B. stearothermophilus* α-amylase. E. A. MacGregor (1987) predicts the presence of α-helices and β-barrels in α-amylases from different sources, including barley, pig pancreas and *Bacillus amyloliquefaciens* on the basis of the known structure of the *A. oryzae* TAKA α-amylase and secondary structure predicting algorithms. Furthermore, the possible loops and subsites which may be found to be present in, e.g., the *B. amyloliquefaciens* α-amylase are predicted (based on a comparison with the *A. oryzae* sequence and structure).

A. E. MacGregor (Starch/Stärke 45 (1993), No. 7, p. 232-237) presents a review of the relationship between the structure and activity of α-amylase related enzymes.

Hitherto, no three-dimensional structure has been available for the industrially important *Bacillus* α-amylases (which in the present context are termed "Termamyl-like α-amylases"), including the *B. licheniformis*, the *B. amyloliquefaciens*, and the *B. stearothermophilus* α-amylase.

BRIEF DISCLOSURE OF THE INVENTION

The three-dimensional structure of a Termamyl-like bacterial α-amylase has now been elucidated. On the basis of an analysis of said structure it is possible to identify structural parts or specific amino acid residues which from structural or functional considerations appear to be important for conferring the various properties to the Termamyl-like α-amylases. Furthermore, when comparing the Termamyl-like α-amylase structure with known structures of the fungal and mammalian α-amylases mentioned above, it has been found that some similarities exist between the structures, but also that some striking, and not previously predicted structural differences between the α-amylases exist. The present invention is based on these findings.

Accordingly, in a first aspect the invention relates to a method of constructing a variant of a parent Termamyl-like α-amylase, which variant has α-amylase activity and at least one altered property as compared to said parent α-amylase, which method comprises i) analysing the structure of the Termamyl-like α-amylase with a view to identifying at least one amino acid residue or at least one structural part of the Termamyl-like α-amylase structure, which amino acid residue or structural part is believed to be of relevance for altering said property of the parent Termamyl-like α-amylase (as evaluated on the basis of structural or functional considerations), ii) constructing a Termamyl-like α-amylase variant, which as compared to the parent Termamyl-like α-amylase, has been modified in the amino acid residue or structural part identified in i) so as to alter said property, and, optionally, iii) testing the resulting Termamyl-like α-amylase variant with respect to said property.

In a second aspect the present invention relates to a method of constructing a variant of a parent Termamyl-like α-amylase, which variant has α-amylase activity and one or more altered properties as compared to said parent α-amylase, which method comprises i) comparing the three-dimensional structure of the Termamyl-like α-amylase with the structure of a non-Termamyl-like α-amylase, ii) identifying a part of the Termamyl-like α-amylase structure which is different from the non-Termamyl-like α-amylase structure, iii) modifying the part of the Termamyl-like α-amylase identified in ii) whereby a Termamyl-like α-amylase variant is obtained, one or more properties of which differ from the parent Termamyl-like α-amylase, and optionally, iv) testing the resulting Termamyl-like α-amylase variant with respect to said property or properties.

In a third aspect the invention relates to a method of constructing a variant of a parent non-Termamyl-like α-amylase, which variant has α-amylase activity and one or more altered properties as compared to said parent α-amylase, which method comprises i) comparing the three-dimensional structure of the non-Termamyl-like α-amylase with the structure of a Termamyl-like α-amylase, ii) identifying a part of the non-Termamyl-like α-amylase structure which is different from the Termamyl-like α-amylase structure, iii) modifying the part of the non-Termamyl-like α-amylase identified in ii) whereby a non-Termamyl-like α-amylase variant is obtained, one or more properties of which differ from the parent non-Termamyl-like α-amylase, and optionally, iv) testing the resulting non-Termamyl-like α-amylase variant with respect to said property or properties.

The property which may be altered by the above methods of the present invention may, e.g., be substrate specificity, substrate binding, substrate cleavage pattern, temperature stability, pH dependent activity, pH dependent stability (especially increased stability at low (e.g. pH<6, in particular pH<5) or high (e.g. pH>9) pH values), stability towards oxidation, $Ca^{2+}$-dependency, specific activity, and other properties of interest. For instance, the alteration may result in a variant which, as compared to the parent Termamyl-like α-amylase, has an increased specific activity at a given pH and/or an altered substrate specificity.

In still further aspects the invention relates to variants of a Termamyl-like α-amylase, DNA encoding such variants and methods of preparing the variants. Finally, the invention relates to the use of the variants for various industrial purposes.

BRIEF DESCRIPTION OF THE DRAWINGS

FIG. 8 shows the amino acid sequence of the polypeptide of SEQ ID NO:12 and the nucleotide sequence encoding the polypeptide.

DETAILED DISCLOSURE OF THE INVENTION

The Termamyl-Like α-Amylase

Figure 1:
FIGS. 1-6 show schematic representations of the three-dimensional structure of the polypeptide depicted in SEQ ID NO:13
Figure 2:
Figure 3:
Figure 4:
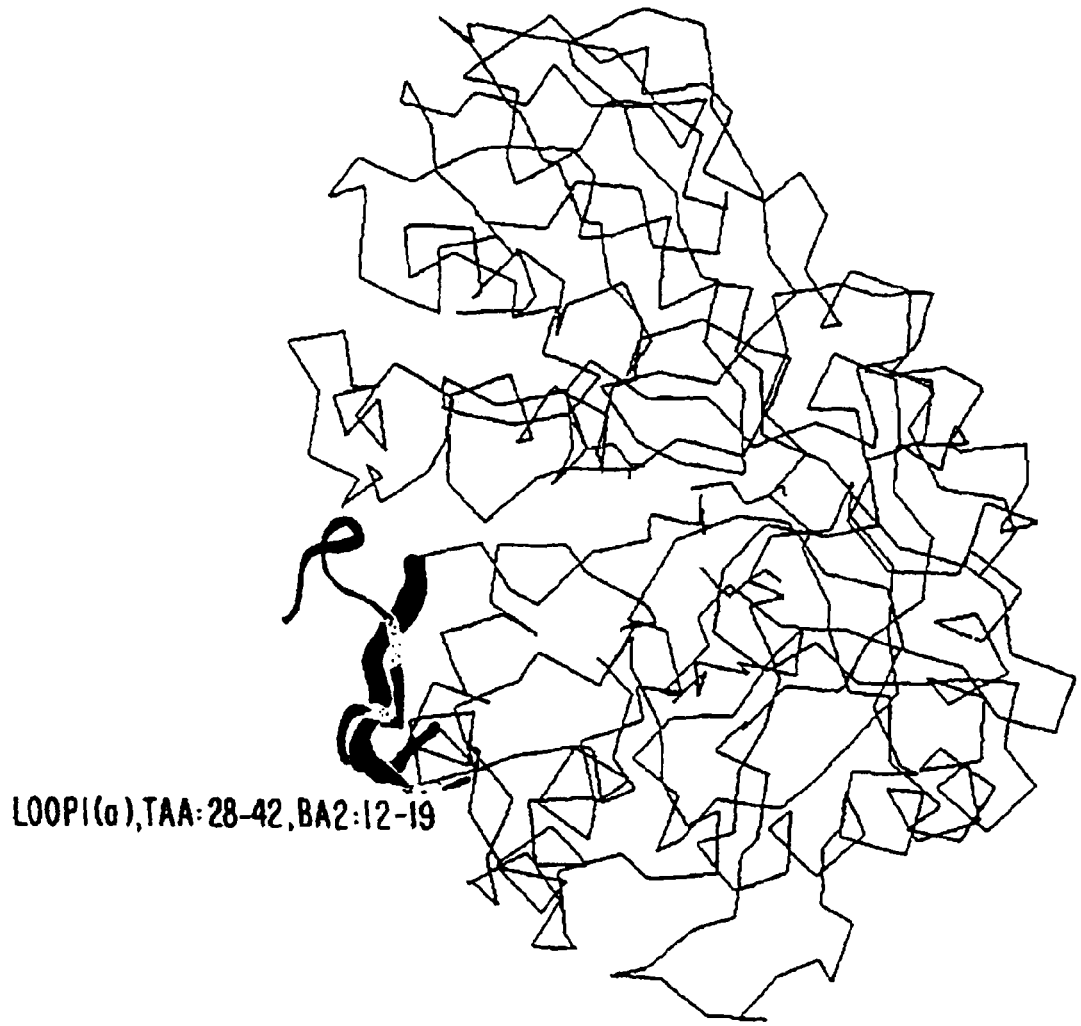
Figure 5:
Figure 6:
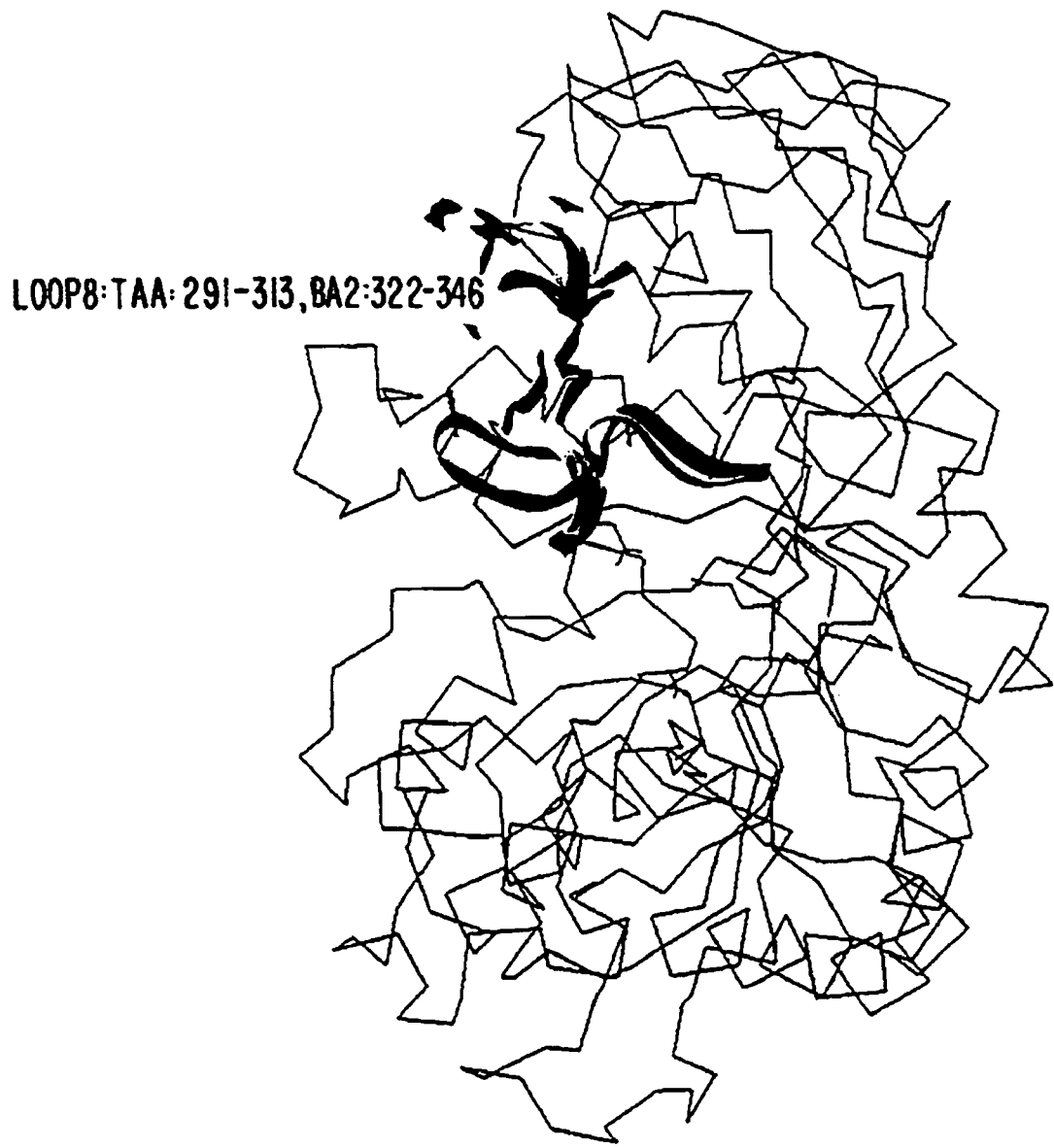

It is well known that a number of alpha-amylases produced by *Bacillus* spp. are highly homologous on the amino acid level. For instance, the *B. licheniformis* α-amylase comprising the amino acid sequence shown in SEQ ID NO: 2 (commercially available as Termamyl®) has been found to be about 89% homologous with the *B. amyloliquefaciens* α-amylase comprising the amino acid sequence shown in SEQ ID NO: 4 and about 79% homologous with the *B. stearothermophilus* α-amylase comprising the amino acid sequence shown in SEQ ID NO: 6. Further homologous α-amylases include an α-amylase derived from a strain of the *Bacillus* sp. NCIB 12289, NCIB 12512, NCIB 12513 or DSM 9375, all of which are described in detail in WO 95/26397, and the α-amylase described by Tsukamoto et al., 1988, Biochemical and Biophysical Research Communications, Vol. 151, No. 1. Still other homologous α-amylases include the α-amylase produced by the *B. licheniformis* described in EP 252 666 (ATCC 27811), and the α-amylases identified in WO 91/00353 and WO 94/18314. Other commercial Termamyl-like *B. licheniformis* α-amylases are Optitherm® and Takatherm® (available from Solvay), Maxamyl® (available from Gist-brocades/Genencor), Spezym AA® (available from Genencor), and Keistase® (available from Daiwa).

Because of the substantial homology found between these α-amylases, they are considered to belong to the same class of α-amylases, namely the class of "Termamyl-like α-amylases".

Accordingly, in the present context, the term "Termamyl-like α-amylase" is intended to indicate an α-amylase which, on the amino acid level, exhibits a substantial homology to Termamyl®, i.e. the *B. licheniformis* α-amylase SEQ ID NO: 2. In other words, a Termamyl-like α-amylase is an α-amylase, which has the amino acid sequence shown in SEQ ID NO: 2, 4 or 6 herein, or the amino acid sequence shown in SEQ ID NO: 1 or 2 of WO 95/26397 or in Tsukamoto et al., 1988, or i) which displays at least 60%, such as at least 70%, e.g. at least 75%, or at least 80%, e.g. at least 85%, at least 90% or at least 95% homology with at least one of said amino acid sequences and/or ii) displays immunological cross-reactivity with an antibody raised against at least one of said α-amylases, and/or iii) is encoded by a DNA sequence which hybridizes to the DNA sequences encoding the above specified α-amylases which are apparent from SEQ ID NO: 1, 3 and 5 of the present application, and SEQ ID NO: 4 and 5 of WO 95/26397, respectively.

In connection with property i) the "homology" may be determined by use of any conventional algorithm, preferably by use of the GAP progamme from the GCG package version 7.3 (June 1993) using default values for GAP penalties (Genetic Computer Group (1991) Programme Manual for the GCG Package, version 7, 575 Science Drive, Madison, Wis., USA 53711).

Property ii) of the α-amylase, i.e. the immunological cross reactivity, may be assayed using an antibody raised against or reactive with at least one epitope of the relevant Termamyl-like α-amylase. The antibody, which may either be monoclonal or polyclonal, may be produced by methods known in the art, e.g. as described by Hudson et al., 1989. The immunological cross-reactivity may be determined using assays known in the art, examples of which are Western Blotting or radial immunodiffusion assay, e.g. as described by Hudson et al., 1989. In this respect, immunological cross-reactivity between the α-amylases having the amino acid sequences SEQ ID NO: 2, 4 and 6, respectively, has been found.

The oligonucleotide probe used in the characterization of the Termamyl-like α-amylase in accordance with property iii) above may suitably be prepared on the basis of the full or partial nucleotide or amino acid sequence of the α-amylase in question. Suitable conditions for testing hybridization involve presoaking in 5×SSC and prehybridizing for 1 h at ~40° C. in a solution of 20% formamide, 5×Denhardt's solution, 50 mM sodium phosphate, pH 6.8, and 50 μg of denatured sonicated calf thymus DNA, followed by hybridization in the same solution supplemented with 100 μM ATP for 18 h at ~40° C., or other methods described by e.g. Sambrook et al., 1989.

In the present context, "derived from" is intended not only to indicate an α-amylase produced or producible by a strain of the organism in question, but also an α-amylase encoded by a DNA sequence isolated from such strain and produced in a host organism transformed with said DNA sequence. Finally, the term is intended to indicate an α-amylase which is encoded by a DNA sequence of synthetic and/or cDNA origin and which has the identifying characteristics of the α-amylase in question. The term is also intended to indicate that the parent α-amylase may be a variant of a naturally occurring α-amylase, i.e. a variant which is the result of a modification (insertion, substitution, deletion) of one or more amino acid residues of the naturally occurring α-amylase.

Parent Hybrid α-Amylases

The parent α-amylase (being a Termamyl-like or non-Termamyl-like α-amylase) may be a hybrid α-amylase, i.e. an α-amylase which comprises a combination of partial amino acid sequences derived from at least two α-amylases.

The parent hybrid α-amylase may be one which on the basis of amino acid homology and/or immunological cross-reactivity and/or DNA hybridization (as defined above) can be determined to belong to the Termamyl-like α-amylase family. In this case, the hybrid α-amylase is typically composed of at least one part of a Termamyl-like α-amylase and part(s) of one or more other α-amylases selected from Termamyl-like α-amylases or non-Termamyl-like α-amylases of microbial (bacterial or fungal) and/or mammalian origin.

Thus, the parent hybrid α-amylase may comprise a combination of at least two Termamyl-like α-amylases, or of at least one Termamyl-like and at least one non-Termamyl-like bacterial α-amylase, or of at least one Termamyl-like and at least one fungal α-amylase. For instance, the parent α-amylase comprises a C-terminal part of an α-amylase derived from a strain of *B. licheniformis* and a N-terminal part of an α-amylase derived from a strain of *B. amyloliquefaciens* or from a strain of *B. stearothermophilus*. For instance, the parent α-amylase comprises at least 430 amino acid residues of the C-terminal part of the *B. licheniformis* α-amylase, and may, e.g. comprise a) an amino acid segment corresponding to the 37 N-terminal amino acid residues of the *B. amyloliquefaciens* α-amylase having the amino acid sequence shown in SEQ ID NO: 4 and an amino acid segment corresponding to the 445 C-terminal amino acid residues of the *B. licheniformis* α-amylase having the amino acid sequence shown in SEQ ID NO: 2, or b) an amino acid segment corresponding to the 68 N-terminal amino acid residues of the *B. stearothermophilus* α-amylase having the amino acid sequence shown in SEQ ID NO: 6 and an amino acid segment corresponding to the 415 C-terminal amino acid residues of the *B. licheniformis* α-amylase having the amino acid sequence shown in SEQ ID NO: 2.

Analogously, the parent hybrid α-amylase may belong to a non-Termamyl-like α-amylase family, e.g. the Fungamyl-like α-amylase family. In that case the hybrid may comprise at least one part of an α-amylase belonging to the non-Termamyl-like α-amylase family in combination with one or more parts derived from other α-amylases.

The Three-Dimensional Termamyl-Like α-Amylase Structure

The Termamyl-like α-amylase which was used to elucidate the three-dimensional structure forming the basis for the present invention (SEQ ID NO: 13) consists of the 300 N-terminal amino acids of the *B. amyloliquefaciens* α-amylase (with the amino acid sequence shown in SEQ ID NO: 4) and amino acids 301-483 of the C-terminal end of the *B. licheniformis* α-amylase with the amino acid sequence SEQ ID NO: 2. The bacterial α-amylase belongs to the "Termamyl-like α-amylase family" and the present structure is believed to be representative for the structure of any Termamyl-like α-amylase.

The structure of the α-amylase was solved in accordance with the principle for X-ray crystallographic methods given in "X-Ray Structure Determination", Stout, G. K. and Jensen, L. H., John Wiley & Sons, inc. NY, 1989. The structural coordinates for the solved crystal structure of the α-amylase at 2.2 Å resolution using the isomorphous replacement method are given in a standard PDB format (Brookhaven Protein Data Base) in Appendix 1. It is to be understood that Appendix 1 forms part of the present application.

Amino acid residues of the enzyme are identified by three-letter amino acid code (capitalized letters).

The α-amylase structure is made up of three globular domains ordered A, B, and C with respect to sequence, which lie approximately along a line in the order B, A, C. The domains can be defined as being residues 1-103 and 206-395 for domain A, residues 104-205 for domain B, and residues 396-483 for domain C, the numbers referring to the *B. licheniformis* α-amylase. This gives rise to an elongated molecule, the longest axis being about 85 Å. The widest point perpendicular to this axis is approximately 50 Å and spans the central A domain. The active site residues of the *B. licheniformis* α-amylase (SEQ ID NO: 2) are D323, D231 and E261.

Domain A

Domain A is the largest domain and contains the active site (comprised of a cluster of three amino acid residues placed at the bottom of a deep cleft in the enzyme's surface). Domain A of all known α-amylase structures have the same overall fold, viz. the (beta/alpha)$_8$ barrel with 8 central beta strands (number 1-8) and 8 flanking α-helices. The β-barrel is defined by McGregor op. cit. The C-terminal end of Beta strand 1 is connected to helix 1 by a loop denoted loop 1 and an identical pattern is found for the other loops. These loops show some variation in size and some can be quite extensive.

The 8 central Beta-strands in the (beta/alpha)8 barrel superimpose well between the various known α-amylase structures, and this part of the structure, including the close surroundings of the active site located at the c-terminal end of the beta-strands, show high similarity between the different amylases.

The loops connecting beta-strands and alpha helices display high variations between alpha amylases. These loops constitute the structural context of the active site and the majority of the contacts to the substrate is found among residues located in these loops. Such important characteristics as substrate specificity, substrate binding, pH/activity profile, starch cleavage pattern are determined by the amino acids and the positions of same in these loops.

The substantial differences between the Fungamyl-like α-amylase structure and the structure of the Termamyl-like α-amylase disclosed herein which are found in loops 1, 2, 3, and 8 are visualized in the Figures.

Domain B

The Termamyl-like α-amylase structure has been found to comprise a special domain structure in the A domain's loop3, also called domain B. The structure of the Termamyl-like α-amylase B domain has never been seen before in any of the known α-amylase or (β/alpha)8-barrel proteins.

Figure 7:
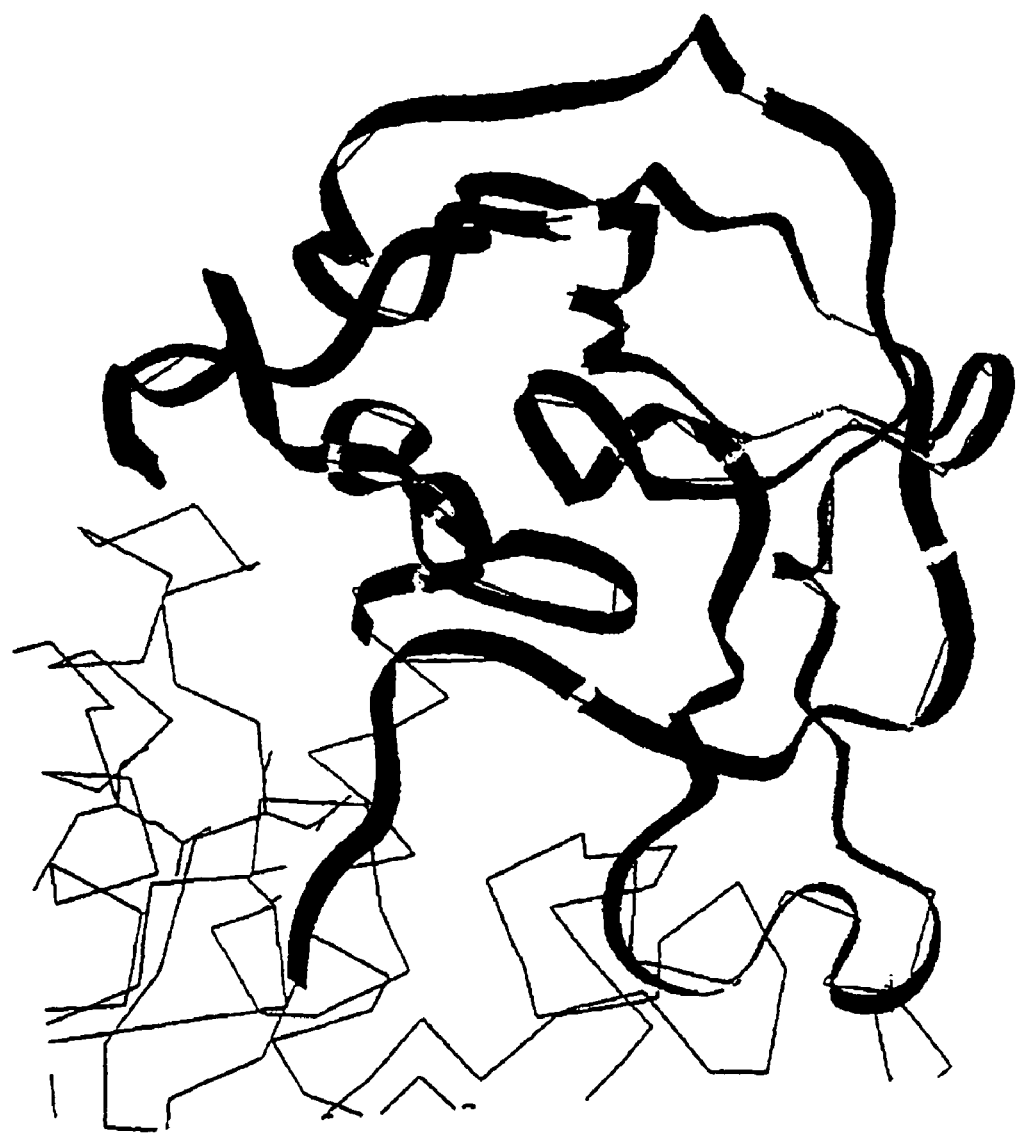
FIG. 7 shows a schematic representation of the three-dimensional structure of the B domain of the polypeptide depicted in SEQ ID NO:13.

The domain B structure is a very compact domain having a very high number of charged residues. The B domain arises as an extension of the loop between strand 3 and helix 3 of domain A (shown in FIG. 7) and contains a 5 stranded antiparallel β-sheet structure containing at least one long loop structure and having the connectivity −1, +3, −1×, +2 (Richardson, 1981, Adv. Protein Chem. 34, 167-339).

The first four strands of the B domain form two hairpin loops which twist around each other like a pair of crossed fingers (right-hand twist). The mainchain folds into a β-strand which connects two small β-sheet structures. After making one turn in one sheet it folds back and makes up a two stranded sheet in contact with domain A and an internal hole in the α-amylase structure. Then the mainchain folds up to a small sheet structure nearly perpendicular to the first two sheets. Before entering the helix 3 on top of the β-strand 3, the approximately 24 last amino acids in domain B form two calcium binding sites in the contact region to domain A.

Domain B is connected with domain A by two peptide stretches, which divide the domain-domain contact areas into two. Domain B is in contact with Domain A by a calcium binding region and an internally buried hole containing waters. Many types of molecular contacts are present. Ionic interacting between acid and basic amino acids are possible, these interactions are very important for the general stability at high pH and for keeping the Calcium binding sites intact.

Domain C

Domain C is the C-terminal part of the protein consisting of amino acids 394-483. Domain C is composed entirely of β-strands which forms a single 8-stranded sheet structure, which folds back on itself, and thus may be described as a β-sandwich structure. The connectivity is +1, +1, +5, −3, +1, +1, −3 although strands 6 and 7 are only loosely connected. One part of the β-sheet forms the interface to domain A.

Ca-Binding and Na-Binding Sites

The structure of the Termamyl-like α-amylase is remarkable in that it exhibits four calcium-binding sites and one sodium-binding site. In other words four calcium ions and one sodium ion are found to be present in the structure, although one of the calcium ions displays very weak coordination. Two of the calcium ions form part of a linear cluster of three ions, the central ion being attributed to sodium, which lie at the junction of the A and B domains.

The coordinating residues for the calcium ions between the A and B domain are as follows (using the Pdb file nomenclature for amino acid residues and atoms in the Pdb file found in Appendix 1 herein): For the calcium ion nearest to the active site (IUM 502 in the pdb file), the backbone carbonyls from His235 and Asp194, the sidechain atom OD1 from residues Asp194, Asn102 and Asp200, and one water molecule WAT X3 (atom OW7). For the sodium ion (IUM 505), the binding site includes atom OD2 from Asp194, Asp200, Asp183 and Asp159, and a backbone carbonyl from Val201. The coordinates for the other calcium ion between domain A and B are (IUM 501): atom OD2 from Asp204 and Asp159, backbone carbonyl from Asp183 and Ala181, atom OD1 from Asp202, and one water molecule WAT X7 (atom OW7).

One calcium ion is located between the A and C domain, another is located in the C domain. The first mentioned calcium ion, which is also the one best coordinated (IUM 503) includes a carbonyl backbone from Gly300, Tyr302 and His406, atom OD2/OD1 from Asp430, atom OD1 from Asp407, and one water molecule WAT X6 (atom OW7). The other and very weakly coordinated calcium site (IUM 504) comprises 4 water molecules WAT X21 (atom OW8), X6 (atom OW6), X9 (atom OW0) and X28 (atom OW8), OE1/OE2 from Glu447 and OD1 from Asn444.

Substrate-Binding Site

Without being limited to any theory it is presently believed that favourable interactions between a substrate molecule and the enzyme (such as hydrogen bonds and/or strong electrostatic interaction) are found within a sphere of 4 Å of the substrate, when bound to the enzyme. The following residues of the *B. licheniformis* α-amylase having the amino acid sequence shown in SEQ ID NO: 2 are contemplated to be within a distance of 4 Å of the substrate and thus believed to be involved in interactions with the substrate:

Trp13, Tyr14, Asn17, Asp18, Ser50, Gln51, Ala52, Asp53, Val54, Gly55, Tyr56, Lys70, Arg74, Lys76, Val102, His105, Gly107, Gly108, Ala109, Trp138, Thr163, Asp164, Trp165, Asn172, Glu189, Tyr193, Leu196, Met197, Tyr198, Ala199, Arg229, Asp231, Ala232, Lys234, His235, Glu261, Trp263, His327, Asp328, Gln333, Ser334, and Leu335.

The amino acid residues of another Termamyl-like α-amylase, which are contemplated to be within a distance of 4 Å of the substrate, may easily be identified by aligning the amino acid sequence SEQ ID NO: 2 with that of the other Termamyl-like α-amylase and thereby identifying the positions equivalent to those identified above.

Generality of Structure

Because of the high homology between the various Termamyl-like α-amylases, the solved structure defined by the coordinates of Appendix 1 is believed to be representative for the structure of all Termamyl-like α-amylases. A model structure of other Termamyl-like α-amylases may easily be built on the basis of the coordinates given in Appendix 1 adapted to the α-amylase in question by use of an alignment between the respective amino acid sequences. The creation of a model structure is exemplified in Example 1.

The above identified structurally characteristic parts of the Termamyl-like α-amylase structure (Ca-binding site, substrate binding site, loops, etc.) may easily be identified in other Termamyl-like α-amylases on the basis of a model (or solved) structure of the relevant Termamyl-like α-amylase or simply on the basis of an alignment between the amino acid sequence of the Termamyl-like α-amylase in question with that of the *B. lichenformis* α-amylase used herein for identifying the amino acid residues of the respective structural elements.

Furthermore, in connection with Termamyl-like variants of the invention, which are defined by modification of specific amino acid residues of a specific Termamyl-like α-amylase, it will be understood that variants of another Termamyl-like α-amylase modified in an equivalent position (as determined from the best possible amino acid sequence alignment between the respective sequences) are intended to be covered as well. Thus, irrespective of whether an amino acid residue is identified herein for the purpose of defining a structural part of a given α-amylase or used for identifying a variant of the α-amylase, this amino acid residue shall be considered as representing the equivalent amino acid residue of any other Termamyl-like α-amylase.

Methods of the Invention for Design of Novel α-Amylase Variants

In the methods according to the first, second and third aspects of the invention the terms "structure of a Termamyl-like α-amylase" and "Termamyl-like α-amylase structure" are intended to indicate the solved structure defined by the coordinates presented in Appendix 1 or a model structure of a given Termamyl-like α-amylase (such as the *B. licheniformis* α-amylase) built on the basis of the solved structure.

In most cases the parent Termamyl-like α-amylase to be modified in accordance with the present invention is different from the α-amylase which was actually used for solving the structure (Appendix 1). This means that the amino acid residue(s) or structural part(s) identified in the solved structure (Appendix 1) in step i) of the method according to the first, second or third aspect of the invention must be translated into the corresponding amino acid residue(s) or structural part(s) of the parent Termamyl-like α-amylase in question. The "translation" is conveniently performed on the basis of an amino acid sequence alignment between the amino acid sequence of the Termamyl-like α-amylase used for solving the structure and the amino acid sequence of the parent Termamyl-like α-amylase in question.

The analysis or comparison performed in step i) of the method according to the first, second and third aspect, respectively, of the invention may be performed by use of any suitable computer programme capable of analysing and/or comparing protein structures, e.g. the computer programme Insight, available from Biosym Technologies, Inc. For instance, the basic principle of structure comparison is that the three-dimensional structures to be compared are superimposed on the basis of an alignment of secondary structure elements (such as the central 8 β-strands in the barrel) and the parts differing between the structures can subsequently easily be identified from the superimposed structure.

The structural part which is identified in step i) of the methods of the first, second and third aspects of the invention may be composed of one amino acid residue. However, normally the structural part comprises more than one amino acid residue, typically constituting one of the above parts of the Termamyl-like α-amylase structure such as one of the A, B, or C domains, an interface between any of these domains, a calcium binding site, a loop structure, the substrate binding site, or the like.

In the present context the term "structural or functional considerations" is intended to indicate that modifications are made on the basis of an analysis of the relevant structure or structural part and its contemplated impact on the function of the enzyme. Thus, an analysis of the structures of the various α-amylases, which until now has been elucidated, optionally in combination with an analysis of the functional differences between these α-amylases, may be used for assigning certain properties of the α-amylases to certain parts of the α-amylase structure or to contemplate such relationship. For instance, differences in the pattern or structure of loops surrounding the active site may result in differences in access to the active site of the substrate and thus differences in substrate specificity and/or cleavage pattern. Furthermore, parts of a Termamyl-like α-amylase involved in or contemplated to be involved in substrate binding (and thus e.g. specificity/cleavage pattern), calcium or sodium ion binding (e.g. of importance for the Calcium-dependency of the enzyme), and the like has been identified (vide infra).

The modification of an amino acid residue or structural part is typically accomplished by suitable modifications of a DNA sequence encoding the parent enzyme in question. The term "modified" as used in step ii) in the method according to the first aspect of the invention is intended to have the following meaning: When used in relation to an amino acid residue the term is intended to mean replacement of the amino acid residue in question with another amino acid residue. When used in relation to a structural part, the term is intended to mean replacement of one or more amino acid residues of said structural part, addition of one or more amino acid residues to said part, or deletion of one or more amino acid residues of said structural part.

The construction of the variant of interest is accomplished by cultivating a microorganism comprising a DNA sequence encoding the variant under conditions which are conducive for producing the variant, and optionally subsequently recovering the variant from the resulting culture broth. This is described in detail further below.

First Aspect of the Invention

In a preferred embodiment of the method according to the first aspect of the invention the property of the parent enzyme to be modified is selected from calcium dependency, substrate binding, cleavage pattern, pH dependent activity and the like. Specific examples of how to change these properties of a parent Termamyl-like α-amylase are given further below.

In another preferred embodiment the parent Termamyl-like α-amylase to be modified is a *B. licheniformis* α-amylase.

Second and Third Aspects of the Invention

One important advantage of the methods according to the second and third aspects of the present invention is that it is possible to adapt the structure (or a structural part) of a Termamyl-like α-amylase to the structure (or structural part) of a non-Termamyl-like α-amylase and vice versa. For instance, having identified a loop structure of the non-Termamyl-like α-amylase which is believed to be responsible for or contributing to a particular property of the non-Termamyl-like α-amylase it is possible to replace the corresponding structure of the Termamyl-like α-amylase with said non-Termamyl-like α-amylase structure—or if no corresponding structure exists in the Termamyl-like α-amylase—to insert the structure into the Termamyl-like α-amylase in such a manner that the resulting variant Termamyl-like α-amylase, as far as the relevant part is concerned, resembles the corresponding part of the non-Termamyl-like α-amylase. When two or more parts of the structure of the parent Termamyl-like α-amylase are modified so as to resemble the corresponding parts of the non-Termamyl-like α-amylase it is possible to increase the resemblance to the non-Termamyl-like α-amylase of the Termamyl-like α-amylase variant and thus to alter the properties of said variant in the direction of those of said non-Termamyl-like α-amylase. Loop modifications are discussed in much further detail further below.

Typically, the modification to be performed in step iii) of the method according to the second aspect of the invention is accomplished by deleting one or more amino acid residues of the part of the Termamyl-like α-amylase to be modified so as to adapt the structure of said part of the parent α-amylase to the corresponding part of the non-Termamyl-like α-amylase; by replacing one or more amino acid residues of the part of the Termamyl-like α-amylase to be modified with the amino acid residues occupying corresponding positions in the non-Termamyl-like α-amylase; or by insertion of one or more amino acid residues present in the non-Termamyl-like α-amylase into a corresponding position in the Termamyl-like α-amylase. For the method according to the third aspect the modification is to be understood analogously, performed on the non-Termamyl-like parent α-amylase rather than the Termamyl-like α-amylase.

In step ii) of the method according to the second or third aspect of the invention the part of the structure to be identified is preferably one which in the folded enzyme is believed to be in contact with the substrate (cf the disclosure above in the section entitled "Substrate-binding site) or involved in substrate specificity and/or cleavage pattern, and/or one which is in contact with one of the calcium or sodium ions and/or one, which is contributing to the pH or temperature profile of the enzyme, or one which otherwise, from structural or functional considerations, is contemplated to be responsible for differences in one or more properties of the Termamyl-like and non-Termamyl-like α-amylase.

Non-Termamyl-Like α-Amylase

The non-Termamyl-like α-amylase with which the comparison is made in step i) of the method of the second aspect of the invention and which is the parent α-amylase in the method of the third aspect of the invention, may be any α-amylase, which does not belong to the family of Termamyl-like α-amylases (as defined above) and, which as a consequence thereof, has a different three-dimensional structure. Furthermore, the non-Termamyl-like α-amylase should be one which has, at the time that the method is performed, an elucidated or contemplated three-dimensional structure.

The non-Termamyl-like α-amylase may, e.g., be a fungal α-amylase, a mammalian or a plant α-amylase or a bacterial α-amylase (different from a Termamyl-like α-amylase). Specific examples of such α-amylases include the *Aspergillus oryzae* TAKA α-amylase, the *A. niger* acid α-amylase, the *Bacillus subtilis* α-amylase, the porcine pancreatic α-amylase and a barley α-amylase. All of these α-amylases have elucidated structures which are clearly different from the structure of the Termamyl-like α-amylase shown herein.

The fungal α-amylases mentioned above, i.e. derived from *A. niger* and *A. oryzae*, are highly homologous on the amino acid level and generally considered to belong to the same family of α-amylases. In the present disclosure, this family is termed "Fungamyl-like α-amylase" and intends to indicate an α-amylase which exhibits a high homology, i.e. more than 70%, such as 80% homologous (as defined herein) to the fungal α-amylase derived from *Aspergillus oryzae*, commercially available as Fungamyl®, and the *A. niger* α-amylase.

From the enclosed illustrations of the α-amylase structure of a Termamyl-like α-amylase and a comparison of said structure with the structure of a Fungamyl-like α-amylase it is evident that major differences exist between the two structures. In the method of the invention it is of particular interest to modify parts of the parent Termamyl-like α-amylase, which belong to a region with large differences to the Fungamyl-like α-amylase. In particular, it is of interest to modify the parent Termamyl-like α-amylase in one or more of the following loops: loop 1, loop 2, loop 3 and/or loop 8 of the parent α-amylase.

In the method of the third aspect of the invention it is of particular interest to modify loop 1, loop 2, loop 3 and/or loop 8 of the parent non-Termamyl-like α-amylase to a closer ressemblance to the similar loops of a Termamyl-like α-amylase, such as Termamyl.

In the following specific types of variants are described which have been designed by use of the method of the invention.

Loop Modifications

In order to change the substrate specificity of the parent α-amylase to be modified it is relevant to consider loop modifications. For instance changing one or more of the loop structures of the Termamyl-like α-amylase into a closer ressemblance with the corresponding loop structure(s) of a non-Termamyl-like α-amylase (such as a Fungamyl-like α-amylase) it is contemplated that it is possible to change the substrate specificity in the direction of that of the non-Termamyl α-amylase. In the following different types of loop modifications of interest are listed. It will be understood that the variants may have other changed properties in addition to the modified substrate specificity. It will be understood that the following modifications identified for a specific Termamyl-like α-amylase are intended to include corresponding modifications in other equivalent positions of other Termamyl-like α-amylases. Furthermore, it will be understood that, normally, the loop modification will comprise replacement of an entire loop structure or a substantial part thereof in, e.g., the Termamyl-like α-amylase, with the corresponding loop structure (or substantial part thereof) in a non-Termamyl-like α-amylase.

Loop2 Modifications

In one embodiment the invention relates to a variant of a parent Termamyl-like α-amylase, in which variant at least one amino acid residue of the parent α-amylase, which is/are present in a fragment corresponding to the amino acid fragment 44-57 of the amino acid sequence of SEQ ID NO: 4, i.e. loop 2, has been deleted or replaced with one or more amino acid residues which is/are present in a fragment corresponding to the amino acid fragment 66-84 of the amino acid sequence shown in SEQ ID NO: 10, or in which one or more additional amino acid residues has been added using the relevant part of SEQ ID NO: 10 or a corresponding part of another Fungamyl-like α-amylase as a template.

The amino acid sequence shown in SEQ ID NO: 10 is the amino acid sequence of the *A. oryzae* α-amylase, i.e. a Fungamyl-like α-amylase. It will be understood that amino acid residues or fragments found in corresponding positions in other α-amylases, in particular Fungamyl-like α-amylases, may be used as a template for the construction of the variant according to the invention. The corresponding part in other homologous α-amylases may easily be identified on the basis of a comparison of the amino acid sequences and/or three-dimensional structures of the respective α-amylases.

For instance, the variant may be one, which, when the amino acid sequence of the variant is aligned most closely with the amino acid sequence of the said parent α-amylase, occupies the same position as the portion from residue X to residue Y of SEQ ID NO: 4, the said region having at least 80% such as at least 90% sequence homology with the part of SEQ ID NO: 10 extending from residue Z to residue V of SEQ ID NO: 10, wherein X is the amino acid residue occupying position 44, 45, 46, 47 or 48 of SEQ ID NO: 4, Y is the amino acid residue occupying position 51, 52, 53, 54, 55, 56 or 57 of SEQ ID NO: 4, Z is the amino acid residue occupying position 66, 67, 68, 69 or 70 of SEQ ID NO: 10, and V is the amino acid residue occupying position 78, 79, 80, 81, 82, 83 or 84 of SEQ ID NO: 10.

In other words, the variant may be one in which an amino acid fragment X—Y of the parent α-amylase, which corresponds to or is within the amino acid fragment 44-57 of SEQ ID NO: 4, has been replaced with an amino acid fragment Z—V, which corresponds to or is within the amino acid fragment 66-84 of the amino acid sequence shown in SEQ ID NO: 10, in X, Y, Z and V have the meaning indicated above.

A specific example of a variant according to this embodiment is a variant of a parent Termamyl-like α-amylase, in which the amino acid fragment of the parent α-amylase, which corresponds to amino acid residues 48-51 of SEQ ID NO: 4, has been replaced with an amino acid fragment corresponding to amino acid residues 70-78 of the amino acid sequence shown in SEQ ID NO: 10.

Loop 3 Modifications—Limited Alteration

In another embodiment the invention relates to a variant of a parent Termamyl-like α-amylase, in which variant at least one of the amino acid residues of the parent α-amylase, which is/are present in an amino acid fragment corresponding to the amino acid fragment 195-202 of the amino acid sequence of SEQ ID NO: 4, has been deleted or replaced with one or more of the amino acid residues which is/are present in an amino acid fragment corresponding to the amino acid fragment 165-177 of the amino acid sequence shown in SEQ ID NO: 10, or in which one or more additional amino acid residues has been added using the relevant part of SEQ ID NO: 10 or a corresponding part of another Fungamyl-like α-amylase as a template.

For instance, the variant may be one in which an amino acid fragment X—Y of the parent α-amylase which corresponds to or is within the amino acid fragment 195-202 of SEQ ID NO: 4, has been replaced by an amino acid fragment Z—V, which corresponds to or is within the amino acid fragment 165-177 of the amino acid sequence shown in SEQ ID NO: 10, in which X is an amino acid residue corresponding to the amino acid occupying position 195 or 196 of SEQ ID NO: 4, Y is an amino acid residue corresponding to the amino acid occupying position 198, 199, 200, 201, or 202 of SEQ ID NO: 4, Z is an amino acid residue corresponding to the amino acid occupying position 165 or 166 of SEQ ID NO: 10, and V is an amino acid residue corresponding to the amino acid occupying position 173, 174, 175, 176 or 177 of SEQ ID NO: 10.

Expressed in another manner, the variant according to this aspect may be one, which, when the amino acid sequence of variant is aligned most closely with the amino acid sequence of the said parent Termamyl-like α-amylase, occupies the same position as the portion from residue X to residue Y of SEQ ID NO: 4, the said region having at least 80%, such as 90% sequence homology with the part of SEQ ID NO: 10 extending from residue Z to residue V of SEQ ID NO: 10, the meaning of X, Y, Z and V being as identified above.

A specific example of a variant according to this embodiment is a variant of a parent Termamyl-like α-amylase, in which the amino acid fragment of the parent α-amylase, which corresponds to amino acid residues 196-198 of SEQ ID NO: 4, has been replaced with the amino acid fragment corresponding to amino acid residues 166-173 of the amino acid sequence shown in SEQ ID NO: 10.

Loop 3 Modifications—Complete Domain B

In a further embodiment the invention relates to a variant of a parent Termamyl-like α-amylase, in which variant at least one of the amino acid residues of the parent α-amylase, which is/are present in a fragment corresponding to the amino acid fragment 117-185 of the amino acid sequence of SEQ ID NO: 4, has/have been deleted or replaced with one or more of the amino acid residues, which is/are present in an amino acid fragment corresponding to the amino acid fragment 98-210 of the amino acid sequence shown in SEQ ID NO: 10, or in which one or more additional amino acid residues has been added using the relevant part of SEQ ID NO: 10 or a corresponding part of another Fungamyl-like α-amylase as a template.

For instance, the variant may be one, in which an amino acid fragment X—Y of the parent α-amylase, which corresponds to or is within the amino acid fragment 117-185 of SEQ ID NO: 4, has been replaced with an amino acid fragment Z—V, which corresponds to or is within the amino acid fragment 98-210 of the amino acid sequence shown in SEQ ID NO: 10, in which variant X is an amino acid residue corresponding to the amino acid occupying position 117, 118, 119, 120 or 121 of SEQ ID NO: 4, Y is an amino acid residue corresponding to the amino acid occupying position 181, 182, 183, 184 or 185 of SEQ ID NO: 4, Z is an amino acid residue corresponding to the amino acid occupying position 98, 99, 100, 101, 102 of SEQ ID NO: 10, and V is an amino acid residue corresponding to the amino acid occupying position 206, 207, 208, 209 or 210 of SEQ ID NO: 10.

A specific example of a variant according to this embodiment is a variant of a parent α-amylase, in which an amino acid fragment of the parent α-amylase, which corresponds to amino acid residues 121-181 of SEQ ID NO: 4, has been replaced with the amino acid fragment corresponding to amino acid residues 102-206 of the amino acid sequence shown in SEQ ID NO: 10.

In another embodiment the invention relates to a variant of a parent Termamyl-like α-amylase, in which variant at least one of the amino acid residues of the parent α-amylase, which is/are present in a fragment corresponding to the amino acid fragment 117-181 of the amino acid sequence of SEQ ID NO: 4, has/have been deleted or replaced with one or more of the amino acid residues, which is/are present in an amino acid fragment corresponding to the amino acid fragment to 98-206 of the amino acid sequence shown in SEQ ID NO: 10, or in which one or more additional amino acid residues has been added using the relevant part of SEQ ID NO: 10 or a corresponding part of another Fungamyl-like α-amylase as a template.

For instance, the variant may be one, in which the amino acid fragment X—Y of the parent α-amylase, which corresponds to or is within the amino acid fragment 117-177 if SEQ ID NO: 4, has/have been replaced with an amino acid fragment Z—V, which corresponds to or is within the amino acid fragment 98-202 of the amino acid sequence shown in SEQ ID NO: 10, in which variant X is an amino acid residue corresponding to the amino acid occupying position 117, 118, 119, 120 or 121 of SEQ ID NO: 4, Y is an amino acid residue corresponding to the amino acid occupying position 174, 175, 176 or 177 of SEQ ID NO: 4, Z is an amino acid residue corresponding to the amino acid occupying position 98, 99, 100, 101, 102 of SEQ ID NO: 10, and V is an amino acid residue corresponding to the amino acid occupying position 199, 200, 201 or 202 of SEQ ID NO: 10.

A specific example of a variant according to this embodiment of the invention is a variant, in which the amino acid fragment of the parent α-amylase, which corresponds to amino acid residues 121-174 of SEQ ID NO: 4, has been replaced with the amino acid fragment corresponding to amino acid residues 102-199 of the amino acid sequence shown in SEQ ID NO: 10.

Loop 1 Modifications—Minimal Addition

In a further embodiment the present invention relates to a variant of a parent Termamyl-like α-amylase, in which variant at least one of the amino acid residues of the parent α-amylase, which is/are present in an amino acid fragment corresponding to the amino acid fragment 12-19 of the amino acid sequence of SEQ ID NO: 4, has/have been deleted or replaced with one or more of the amino acid residues, which is/are present in an amino acid fragment which corresponds to the amino acid fragment 28-42 of SEQ ID NO: 10, or in which one or more additional amino acid residues has/have been inserted using the relevant part of SEQ ID NO: 10 or a corresponding part of another Fungamyl-like α-amylase as a template.

For instance, the variant may be one, in which the amino acid fragment X—Y of the parent α-amylase, which corresponds to or is within the amino acid fragment 12-19 of SEQ ID NO: 4, has/have been replaced with an amino acid fragment Z—V, which corresponds to or is within the amino acid fragment 28-42 of the amino acid sequence shown in SEQ ID NO: 10, in which variant X is an amino acid residue corresponding to the amino acid occupying position 12, 13 or 14 of SEQ ID NO: 4, Y is an amino acid residue corresponding to the amino acid occupying position 15, 16, 17, 18 or 19 of SEQ ID NO: 4, Z is an amino acid residue corresponding to the amino acid occupying position 28, 29, 30, 31 or 32 of SEQ ID NO: 10, and V is an amino acid residue corresponding to the amino acid occupying position 38, 39, 40, 41 or 42 of SEQ ID NO: 10.

A specific example of a variant according to this aspect of the invention is a variant, in which the amino acid fragment of the parent α-amylase, which corresponds to amino acid residues 14-15 of SEQ ID NO: 4, has been replaced with the amino acid fragment corresponding to amino acid residues 32-38 of the amino acid sequence shown in SEQ ID NO: 10.

Loop 1 Modifications—Complete Loop

In a further embodiment the invention relates to a variant of a parent Termamyl-like α-amylase, in which variant at least one of the amino acid residues of the parent α-amylase, which is present in a fragment corresponding to amino acid residues 7-23 of the amino acid sequence of SEQ ID NO: 4, has/have been deleted or replaced with one or more amino acid residues, which is/are present in an amino acid fragment corresponding to amino acid residues 13-45 of the amino acid sequence shown in SEQ ID NO: 10, or in which one or more additional amino acid residues has/have been inserted using the relevant part of SEQ ID NO: 10 or a corresponding part of another Fungamyl-like α-amylase as a template.

For instance, the variant may be one, in which the amino acid fragment X—Y of the parent α-amylase, which corresponds to or is within the amino acid fragment 7-23 of SEQ ID NO: 4, has/have been replaced with an amino acid fragment Z—V, which corresponds to or is within the amino acid fragment 13-45 of the amino acid sequence shown in SEQ ID NO: 10, in which variant X is an amino acid residue corresponding to the amino acid occupying position 7 or 8 of SEQ ID NO: 4, Y is an amino acid residue corresponding to the amino acid occupying position 18, 19, 20, 21, 22 or 23 of SEQ ID NO: 4, Z is an amino acid residue corresponding to the amino acid occupying position 13 or 14 of SEQ ID NO: 10, and V is an amino acid residue corresponding to the amino acid occupying position 40, 41, 42, 43, 44 or 45 of SEQ ID NO: 10.

A specific variant according to this embodiment is one, in which the amino acid fragment of the parent α-amylase, which corresponds to amino acid residues 8-18 of SEQ ID NO: 4, has been replaced with the amino acid fragment corresponding to amino acid residues 14-40 of the amino acid sequence shown in SEQ ID NO: 10.

Loop 8 Modifications

In a further embodiment the invention relates to a variant of a parent Termamyl-like α-amylase, in which variant at least one of the amino acid residues of the parent α-amylase, which is present in a fragment corresponding to amino acid residues 322-346 of the amino acid sequence of SEQ ID NO: 2, has/have been deleted or replaced with one or more amino acid residues, which is/are present in an amino acid fragment corresponding to amino acid residues 291-313 of the amino acid sequence shown in SEQ ID NO: 10, or in which one or more additional amino acid residues has/have been inserted using the relevant part of SEQ ID NO: 10 or a corresponding part of another Fungamyl-like α-amylase as a template.

For instance, the variant may be one, in which the amino acid fragment X—Y of the parent α-amylase, which corresponds to or is within the amino acid fragment 322-346 of SEQ ID NO: 2, has/have been replaced with an amino acid fragment Z—V, which corresponds to or is within the amino acid fragment 291-313 of the amino acid sequence shown in SEQ ID NO: 10, in which variant X is an amino acid residue corresponding to the amino acid occupying position 322, 323, 324 or 325 of SEQ ID NO: 2, Y is an amino acid residue corresponding to the amino acid occupying position 343, 344, 345 or 346 of SEQ ID NO: 2, Z is an amino acid residue corresponding to the amino acid occupying position 291, 292, 293 or 294 of SEQ ID NO: 10, and V is an amino acid residue corresponding to the amino acid occupying position 310, 311, 312 or 313 of SEQ ID NO: 10.

A specific variant according to this aspect of the invention is one, in which the amino acid fragment of the parent α-amylase, which corresponds to amino acid residues 325-345 of SEQ D No. 2, has been replaced with the amino acid fragment corresponding to amino acid residues 294-313 of the amino acid sequence shown in SEQ ID NO: 10.

$Ca^{2+}$ Dependency

It is highly desirable to be able to decrease the $Ca^{2+}$ dependency of a Termamyl-like α-amylase. Accordingly, in a further aspect the invention relates to a variant of a parent Termamyl-like α-amylase, which exhibits α-amylase activity and which has a decreased $Ca^{2+}$ dependency as compared to the parent α-amylase. The decreased $Ca^{2+}$ dependency has the functional result that the variant exhibits a satisfactory amylolytic activity in the presence of a lower concentration of calcium ion in the extraneous medium than is necessary for the parent enzyme and, for example, therefore is less sensitive than the parent to calcium ion-depleting conditions such as those obtained in media containing calcium-complexing agents (such as certain detergent builders).

The decreased $Ca^{2+}$ dependency of the variant of the invention may advantageously be achieved by increasing the $Ca^{2+}$ binding affinity of the parent Termamyl-like α-amylase, in other words the stronger the $Ca^{2+}$ binding of the enzyme, the lower is the $Ca^{2+}$ dependency.

It is presently believed that amino acid residues located within 10 Å from a sodium or calcium ion are involved in or are of importance for the $Ca^{2+}$ binding capability of the enzyme.

Accordingly, the variant according to this aspect of the invention is preferably one, which has been modified in one or more amino acid residues present within 10 Å from a calcium and/or sodium ion identified in the three-dimensional Termamyl-like α-amylase structure in such a manner that the affinity of the α-amylase for calcium is increased.

The amino acid residues found within a distance of 10 Å from the $Ca^{2+}$ binding sites of the *B. licheniformis* α-amylase with the amino acid sequence SEQ ID NO: 2 were determined as described in Example 2 and are as follows:

V102, I103, N104, H105, K106, R125, W155, W157, Y158, H159, F160, D161, G162, T163, Y175, K176, F177, G178, K180, A181, W182, D183, W184, E185, V186, S187, N192, Y193, D194, Y195, L196, M197, Y198, A199, D200, I201, D202, Y203, D204, H205, P206, V208, A209, D231, A232, V233, K234, H235, I236, K237, F238, F240, L241, A294, A295, S296, T297, Q298, G299, G300, G301, Y302, D303, M304, R305, K306, L307, W342, F343, L346, Q393, Y394, Y396, H405, H406, D407, I408, V409, R413, E414, G415, D416, S417, V419, A420, N421, S422, G423, L424, I428,

T429, D430, G431, P432, V440, G441, R442, Q443, N444, A445, G446, E447, T448, W449, I462, G475, Y480, V481, Q482, R483.

In order to construct a variant according to this aspect of the invention it is desirable to replace at least one of the above mentioned amino acid residues (or an amino acid residue occupying an equivalent position in another Termamyl-like α-amylase than that defined by SEQ ID NO: 2), which is contemplated to be involved in providing a non-optimal calcium binding, with any other amino acid residue which improves the $Ca^{2+}$ binding affinity of the variant enzyme. In practice, the identification and subsequent modification of the amino acid residue is performed by the following method:

i) identifying an amino acid residue within 10 Å from a $Ca^{2+}$ binding site of a Termamyl-like α-amylase structure, which from structural or functional considerations is believed to be responsible for a non-optimal calcium ion interaction, ii) constructing a variant in which said amino acid residue is replaced with another amino acid residue which from structural or functional considerations is believed to be important for establishing a higher $Ca^{2+}$ binding affinity, and testing the $Ca^{2+}$ dependency of the resulting Termamyl-like α-amylase variant.

In the present context, the term "non-optimal calcium ion interaction" is intended to indicate that the amino acid residue in question is selected on the basis of a presumption that substituting said amino acid residue for another may improve a calcium ion binding interaction of the enzyme. For instance, the amino acid residue in question may be selected on the basis of one or more of the following considerations:

- to obtain an improved interaction between a calcium ion and an amino acid residue located near to the surface of the enzyme (as identified from the structure of the Termamyl-like α-amylase). For instance, if the amino acid residue in question is exposed to a surrounding solvent, it may be advantageous to increase the shielding of said amino acid residue from the solvent so as to provide for a stronger interaction between said amino acid residue and a calcium ion. This can be achieved by replacing said residue (or an amino acid residue in the vicinity of said residue contributing to the shielding) by an amino acid residue which is more bulky or otherwise results in an improved shielding effect.
- to stabilize a calcium binding site, for instance by stabilizing the structure of the Termamyl-like α-amylase (e.g. by stabilizing the contacts between the A, B and C domains or stabilizing one or more of the domains as such). This may, e.g., be achieved by providing for a better coordination to amino acid side chains, which may, e.g., be obtained by replacing an N residue with a D residue and/or a Q residue with an E residue (e.g. N104D), e.g. within 10 Å, and preferably within 3 or 4 Å, of a calcium binding site.
- to protect the calcium binding site or to improve the coordination between the calcium ion and the calcium binding site, e.g. by providing a stronger interaction between the ion and the binding site.

Before actually constructing a Termamyl-like α-amylase variant according to the above principles it may be convenient to evaluate the contemplated amino acid modification by its accommodation into the Termamyl-like α-amylase structure, e.g. into a model structure of the parent Termamyl-like α-amylase.

Preferably, the amino acid residue to be modified is located within 8 Å of a $Ca^{2+}$ binding site residue, such as within 5 Å of such residue. The amino acid residues within 8 Å and 5 Å, respectively, may easily be identified by an analogous method used for identifying amino acid residues within 10 Å (cf. Example 2).

The following mutation is contemplated to be of particular interest with respect to decreasing the $Ca^{2+}$ dependency of a Termamyl-like α-amylase:
N104D (of the B. licheniformis α-amylase SEQ ID NO: 2, or an equivalent (N to D) mutation of an equivalent position in another Termamyl-like α-amylase.)

In connection with substitutions of relevance for $Ca^{2+}$ dependency, some other substitutions appear to be of importance in stabilizing the enzyme conformation (for instance the Domains A-B and/or Domains A-C interactions contributing to the overall stability of the enzyme) in that they may, e.g., enhance the strength of binding or retention of calcium ion or sodium ion at or within a calcium or sodium binding site, respectively, within the parent Termamyl-like α-amylase.

It is desirable to stabilize the C-domain in order to increase the calcium stability and/or thermostability of the enzyme. In this connection the stabilization may result in a stabilization of the binding of calcium by the enzyme, and an improved contact between the C-domain and the A-domain (of importance for thermostability). The latter may be achieved by introduction of cystein bridges, salt bridges or increase hydrogen, hydrophobic and/or electrostatic interactions.

For instance, the C-domain of the B. licheniformis α-amylase having the amino acid sequence shown in SEQ ID NO: 2 may be stabilized by introduction of a cystein bridge between domain A and domain C, e.g. by introducing of the following mutations:
A349C+I479C and/or L346C+I430C.

A salt bridge may be obtained by introduction of the following mutations:
N457D,E
N457D,E+K385R
F350D,E+I430R,K
F350D,E+I411R,K The calcium site of Domain C may be stabilized by replacing the amino acid residues H408 and/or G303 with any other amino acid residue. Of particular interest is the following mutations:
H408Q,E,N,D and/or G303N,D,Q,E
which are contemplated to provide a better calcium binding or protection from calcium depletion.

Similar mutations may be introduced in equivalent positions of other Termamyl-like α-amylases.

Other substitution mutations (relative to B. licheniformis α-amylase, SEQ ID NO: 2) which appear to be of importance, inter alia, in the context of reducing calcium dependency include the following:
In Domain A:
R23K;
A209V; and
G310D;
In Domain B:
H156Y;
A181E,D,Q,N,V,T (which appear to result in shielding of the outermost $Ca^{2+}$ binding site in the junction region between Domain A and Domain B to some extent);
I201 (bulkier amino acid), e.g. I201W,F,L (which appear to result in slight alterations in the geometry of the region in the immediate vicinity of the $Ca^{2+}$—$Na^+$—$Ca^{2+}$ binding site(s) in the junction region between Domain A and Domain B, and in the geometry and/or size of a nearby hole/cavity); and
Y203E,Q (which are believed to result in stronger binding of the outermost $Ca^{2+}$ ion in its binding site in the junction region between Domain A and Domain B);

(or equivalent mutations in equivalent positions in another Termamyl-like α-amylase).

Substitutions of R214 and P345 of *B. licheniformis* α-amylase, SEQ ID NO: 2 (or equivalent mutations in equivalent positions in another Termamyl-like α-amylase) with other amino acids may also be of importance in this connection.

Variants with Altered Activity at Higher/Lower pH

It is contemplated that it is possible to change the pH optima of a Termamyl-like α-amylase or the enzymatic activity at a given pH by changing the pKa of the active site residues. This may be achieved, e.g. by changing the electrostatic interaction or hydrophobic interaction between functional groups of amino acid side chains of the amino acid residue to be modified and of its close surroundings. This may, e.g., be accomplished by the following method:

i) in a structure of the Termamyl-like α-amylase in question to identifying an amino acid residue within 15 Å from an active site residue, in particular 10 Å from an active site residue, which amino acid residue is contemplated to be involved in electrostatic or hydrophobic interactions with an active site residue, ii) replacing, in the structure, said amino acid residue with an amino acid residue which changes the electrostatic and/or hydrophobic surroundings of an active site residue and evaluating the accommodation of the amino acid residue in the structure, iii) optionally repeating step i) and/or ii) until an amino acid replacement has been identified which is accommodated into the structure, iv) constructing a Termamyl-like α-amylase variant resulting from steps i), ii) and optionally iii) and testing the pH dependent enzymatic activity of interest of said variant.

In the above method it may be of particular relevance to add a positively charged residue within 5 Å of a glutamate (thereby lowering the pKa of the glutamate from about 4.5 to 4), or to add a negatively charged residue within 5 Å of a glutamate (thereby increasing the pKa to about 5), or to make similar modifications within a distance of about 5 Å of a Histidine.

On the basis of electrostatic considerations [see, e.g., M. K. Gilson, *Current Opinion in Structural Biology* 5 (1995) pp. 216-223; and B. Honig and A. Nicholls, *Science* 268 (1995) pp. 1144-1149; and references given therein] and hygroscopicity considerations in relation to the three dimensional structure of a Termamyl-like α-amylase disclosed herein, mutations of relevance, inter alia, for changing (increasing or decreasing) the pH optimum of a Termamyl-like α-amylase are believed to include the following mutations or equivalents thereof [referring here to the sequence of *B. licheniformis* α-amylase (SEQ ID NO: 2)]:

Q9K,L,E; F11R,K,E; E12Q; D100N,L; V101H,R,K,D,E,F; V102A,T; I103H,K; N104R,K,D; H105R,K,D,E,W,F; L196R,K,D,E,F,Y; I212R,K,D,E; L230H,K,I; A232G,H,F,S,V; V233D; K234L,E; I236R,K,N,H,D,E; L241R,K,D,E,F; A260S; W263H; Q264R,D,K,E; N265K,R,D; A269R,K,D,E; L270R,K,H,D,E; V283H,D; F284H; D285N,L; V286R,K,H,D,E; Y290R,E; V312R,K,D,E; F323H; D325N; N326K,H,D,L; H327Q,N,E,D,F; Q330L,E; G332D; Q333R,K,H,E,L; S334A,V,T,L,I,D; L335G,A,S,T,N; E336R+R375E; T337D,K; T338D,E; T339D; Q360K,R,E; D365N; G371D,R.

In a further aspect the invention relates to a variant of a Termamyl-like α-amylase which exhibits a higher activity at a lower pH (e.g. compared to the pH optimum) than the parent α-amylase. In particular, the variant comprises a mutation of an amino acid residue corresponding to at least one of the following positions of the *B. licheniformis* α-amylase (SEQ ID NO: 2):

E336, Q333, P331, I236, V102, A232, I103, L196

The following mutations are of particular interest:
E336R,K
Q333R,K
P331R,K
V102R,K,A,T,S,G;
I236K,R,N;
I103K,R;
L196K,R;
A232T,S,G;

or any combination of two or more of these variants or any combination of one or more of these variants with any of the other variants disclosed herein.

In a still further aspect the invention relates to a variant of a Termamyl-like α-amylase which has a higher activity at a higher pH than the parent α-amylase. In particular, the variant comprises a mutation of an amino acid residue corresponding to at least one of the following positions of the *B. licheniformis* α-amylase (SEQ ID NO: 2):

N236, H281, Y273

In particular, the variant comprises a mutation corresponding to at least one of the following mutations of the *B. licheniformis* α-amylase (SEQ ID NO: 2):
N326I,Y,F,L,V
H281F,I,L
Y273F,W or any combination of two or more of these variants or any combination of one or more of these variants with any of the other variants disclosed herein.

A mutation which appears to be importance in relation to the specific activity of variants of the invention is a mutation corresponding to the substitution S187D in *B. licheniformis* α-amylase (SEQ ID NO: 2).

Variants with Increased Thermostability and/or Altered Temperature Optimum

In a further desired aspect the invention relates to a variant of a parent Termamyl-like α-amylase, which variant is the result of one or more amino acid residues having been deleted from, replaced or added to the parent α-amylase so as to obtain an increased thermostability of the variant.

The Termamyl-like α-amylase structure contains a number of unique internal holes, which may contain water, and a number of crevices. In order to increase the thermostability of the α-amylase it may be desirable to reduce the number of holes and crevices (or reduce the size of the holes or crevices), e.g. by introducing one or more hydrophobic contacts, preferably achieved by introducing bulkier residues, in the vicinity or surroundings of the hole. For instance, the amino acid residues to be modified are those which are involved in the formation of the hole.

Accordingly, in a further aspect the present invention relates to a method of increasing the thermostability and/or altering the temperature optimum of a parent Termamyl-like α-amylase, which method comprises i) identifying an internal hole or a crevice of the parent Termamyl-like α-amylase in the three-dimensional structure of said α-amylase, ii) replacing, in the structure, one or more amino acid residues in the neighbourhood of the hole or crevice identified in i) with another amino acid residue which from structural or functional considerations is believed to increase the hydrophobic interaction and to fill out or reduce the size of the hole or crevice, iii) constructing a Termamyl-like α-amylase variant resulting from step ii) and testing the thermostability and/or temperature optimum of the variant.

The structure used for identifying the hole or crevice of the parent Termamyl-like α-amylase may be the structure identified in Appendix 1 or a model structure of the parent Termamyl-like α-amylase built thereon.

It will be understood that the hole or crevice is identified by the amino acid residues surrounding the hole/crevice, and that modification of said amino acid residues are of importance for filling or reducing the size of the hole/crevice. The particular amino acid residues referred to below are those which in crystal structure have been found to flank the hole/crevice in question.

In order to fill (completely or partly) a major hole located between domain A and B, mutation to any other amino acid residue of an amino acid residue corresponding to one or more of the following residues of the *B. licheniformis* α-amylase (SEQ ID NO: 2) is contemplated:
L61, Y62, F67, K106, G145, I212, S151, R214, Y150, F143, R146

Of particular interest is a mutation to a more bulky amino acid residue than the amino acid residue of the parent enzyme.

Of particular interest is a variant of a Termamyl-like α-amylase which comprises a mutation corresponding to the following mutations (using the numbering of *B. licheniformis* α-amylase (SEQ ID NO: 2):
L61W,V,F;
Y62W;
F67W;
K106R,F,W;
G145F,W
I212F,L,W,Y,R,K;
S151 replaced with any other amino acid residue and in particular with F, W, I or L;
R214W;
Y150R,K;
F143W; and/or
R146W.

In order to fill a hole in the vicinity of the active site mutation to any other amino acid residue of an amino acid residue corresponding to one or more of the following residues of the *B. licheniformis* α-amylase (SEQ ID NO: 2) is contemplated:
L241, I236.

Of interest is a mutation to a more bulky amino acid residue.

Of particular interest is a variant of a Termamyl-like α-amylase which comprises a mutation corresponding to one or more of the following mutations in the *B. licheniformis* α-amylase:
L241I,F,Y,W; and/or
I236L,F,W,Y In order to fill a hole in the vicinity of the active site mutation to any other amino acid residue of an amino acid residue corresponding to one or more of the following residues of the *B. licheniformis* α-amylase (SEQ ID NO: 2) is contemplated:
L7, V259, F284

Of interest is a mutation to a more bulky amino acid residue.

Of particular interest is a variant of a Termamyl-like α-amylase which comprises a mutation corresponding to one or more of the following mutations in the *B. licheniformis* α-amylase:
L7F,I,W
V259F,I,L
F284W In order to fill a hole in the vicinity of the active site mutation to any other amino acid residue of an amino acid residue corresponding to one or more of the following residues of the *B. licheniformis* α-amylase (SEQ ID NO: 2) is contemplated:
F350, F343

Of interest is a mutation to a more bulky amino acid residue.

Of particular interest is a variant of a Termamyl-like α-amylase which comprises a mutation corresponding to one or more of the following mutations in the *B. licheniformis* α-amylase:
F350W
F343W In order to fill a hole in the vicinity of the active site mutation to any other amino acid residue of an amino acid residue corresponding to one or more of the following residues of the *B. licheniformis* α-amylase (SEQ ID NO: 2) is contemplated:
L427, V481

Of interest is a mutation to a more bulky amino acid residue.

Of particular interest is a variant of a Termamyl-like α-amylase which comprises a mutation corresponding to one or more of the following mutations in the *B. licheniformis* α-amylase:
L427F,L,W
V481,F,I,L,W It can be seen from an alignment of the amino acid sequences of α-amylases from various *Bacillus* species that *B. licheniformis* α-amylase and *B. amyloliquefaciens* α-amylase both contain an "insertion" of three amino acids relative to, e.g., *B. stearothermophilus* α-amylase.

From a model of the structure of *B. licheniformis* α-amylase built on the basis of the three-dimensional structure of the Termamyl-like α-amylase disclosed herein (vide supra), taking into account the homology of *B. licheniformis* α-amylase to the Termamyl-like α-amylase in question, it can be seen that the above-mentioned "insertion" lies within loop 8 (vide supra), making this loop bulkier in *B. licheniformis* α-amylase than in the Termamyl-like α-amylase and resulting in a loop that protrudes from the structure, thereby possibly destabilizing the structure. It is therefore contemplated that deletion of one or more amino acids in the region in question in *B. licheniformis* or *B. amyloliquefaciens* α-amylase will improve the thermostability of these α-amylases.

Especially interesting in this connection is deletion of three amino acids within the partial sequence from T369 to I377 (referring to the sequence of *B. licheniformis* α-amylase), i.e. the partial sequence: T369-K370-G371-D372-S373-Q374-R375-E376-I377 (or the corresponding partial sequence in *B. amyloliquefaciens* α-amylase). In addition to such deletions, substitution of one or more of the undeleted amino acids within the latter partial sequence may also be advantageous.

Preferable deletions of three amino acids in the partial sequence from T369 to I377 (in *B. licheniformis* α-amylase) are deletion of K370+G371+D372 (i.e. K370*+G371*+D372*) or deletion of D372+S373+Q374 (i.e. D372*+S373*+Q374*) (or equivalent deletions in the corresponding partial sequence in *B. amyloliquefaciens* α-amylase).

Another type of mutation which would appear to be of value in improving the thermostability of these α-amylases is substitution (replacement) of the entire partial amino acid sequence from T369 to I377 (referring to the sequence of *B. licheniformis* α-amylase) with one of the following partial sequences of six amino acids (sequence numbering increasing from left to right): I—P-T-H—S—V; I—P-T-H-G-V; and I—P-Q-Y—N—I (or one of the same substitutions of the corresponding partial sequence in *B. amyloliquefaciens* α-amylase).

Variants with an Altered Cleavage Pattern

In the starch liquefaction process it is desirable to use an α-amylase which is capable of degrading the starch molecules into long branched oligo saccharides (like, e.g. the Fungamyl-like α-amylases) rather than shorter branched oligo saccharides (like conventional Termamyl-like α-amylases). The resulting very small branched oligosaccharides (panose precursors) cannot be hydrolyzed properly by pullulanases, which in the liquefaction process are used after the α-amylases and before the amyloglucosidases. Thus, in the presence of panose precursors the action of amylo-glucoamylase ends up with a high degree of the small branched limiting-dextrin, the trisaccharide panose. The presence of panose lowers the saccharification yield significantly and is thus undesirable.

Thus, one aim of the present invention is to change the degradation characteristics of a Termamyl-like α-amylase to that of a Fungamyl-like α-amylases without at the same time reducing the thermostability of the Termamyl-like α-amylase.

Accordingly, in a further aspect the invention relates to a variant of a Termamyl-like α-amylase which has a reduced ability to cleave a substrate close to the branching point.

The variant may suitably be constructed by a method which comprises i) identifying the substrate binding area of the parent Termamyl-like α-amylase in a model of the three-dimensional structure of said α-amylase, (e.g. within a sphere of 4 Å from the substrate binding site (as defined in the section above entitled "Substrate Binding Site"), ii) replacing, in the model, one or more amino acid residues of the substrate binding area of the cleft identified in i), which is/are believed to be responsible for the cleavage pattern of the parent α-amylase, with another amino acid residue which from structural considerations is believed to result in an altered substrate cleavage pattern, or deleting one or more amino acid residues of the substrate binding area contemplated to introduce favourable interactions to the substrate or adding one or more amino acid residues to the substrate binding area contemplated to introduce favourable interactions to the substrate, and iii) constructing a Termamyl-like α-amylase variant resulting from step ii) and testing the substrate cleavage pattern of the variant.

Of particular interest is a variant which cleaves an amylopectin substrate, from the reducing end, more than one glucose unit from the branching point, preferably more than two or three glucose units from the branching point, i.e. at a further distance from the branching point than that obtained by use of a wild type *B. licheniformis* α-amylase.

Residues of particular interest in connection with this aspect of the invention correspond to the following residues of the *B. licheniformis* α-amylase (SEQ ID NO: 2): V54, D53, Y56, Q333, G57, and the variants according to this aspect preferably comprises a mutation in one or more of these residues.

In particular, the variant comprises at least one of the following mutations, which are expected to prevent cleavage close to the branching point:

V54L,I,F,Y,W,R,K,H,E,Q
D53L,I,F,Y,W
Y56W
Q333W
G57 all possible amino acid residues
A52 amino acid residues larger than A, e.g. A52W,Y,L,F,I.

Variants of a Fungal α-Amylase

In a still further embodiment the invention relates to a variant of a parent Fungamyl-like α-amylase, in which variant at least one of the amino acid residues of the parent α-amylase, which is/are present in an amino acid fragment corresponding to amino acid residues 291-313 of the amino acid sequence of SEQ ID NO: 10, has/have been deleted or replaced with one or more of the amino acid residues, which is/are present in an amino acid fragment corresponding to amino acid residues 98-210 of the amino acid sequence shown in SEQ ID NO: 4, or in which one or more additional amino acid residues has/have been inserted using the relevant part of SEQ ID NO: 4 or a corresponding part of another Termamyl-like α-amylase as a template.

For instance, the variant may be one, in which the amino acid fragment X—Y of the parent α-amylase, which corresponds to or is within the amino acid fragment 117-185 of SEQ ID NO: 10, has/have been replaced with an amino acid fragment Z—V, which corresponds to or is within the amino acid fragment 98-210 of the amino acid sequence shown in SEQ ID NO: 4, in which variant X is an amino acid residue corresponding to the amino acid occupying position 117, 118, 119, 120 or 121 of SEQ ID NO: 10, Y is an amino acid residue corresponding to the amino acid occupying position 181, 182, 183, 184 or 185 of SEQ ID NO: 10, Z is an amino acid residue corresponding to the amino acid occupying position 98, 99, 100, 101 or 102 of SEQ ID NO: 4, and V is an amino acid residue corresponding to the amino acid occupying position 206, 207, 208, 209 or 210 of SEQ ID NO: 4.

A specific example of a variant according to this aspect of the invention is one, in which the amino acid fragment of the parent α-amylase, which corresponds to amino acid residues 121-181 of SEQ ID NO: 10, has been replaced with the amino acid fragment corresponding to amino acid residues 102-206 of the amino acid sequence shown in SEQ ID NO: 4.

Another example of a variant according to this aspect of the invention is one, in which the amino acid fragment of the parent α-amylase, which corresponds to amino acid residues 121-174 of SEQ ID NO: 10, has been replaced with the amino acid fragment corresponding to amino acid residues 102-199 of the amino acid sequence shown in SEQ ID NO: 4.

In a further embodiment the invention relates to a variant of a parent Fungamyl-like α-amylase, in which an amino acid fragment corresponding to amino acid residues 181-184 of the amino acid sequence shown in SEQ ID NO: 10 has been deleted.

General Mutations in Variants of the Invention

It may be preferred that the variant of the invention or prepared in accordance with the method of the invention comprises one or more modifications in addition to those outlined above. Thus, it may be advantageous that one or more proline residues present in the part of the α-amylase variant having been modified is/are replaced with a non-proline residue which may be any of the possible, naturally occurring non-proline residues, and which preferably is an alanine, glycine, serine, threonine, valine or leucine.

Analogously, it may be preferred that one or more cysteine residues present in the amino acid residues with which the parent α-amylase is modified are replaced with a non-cysteine residues such as serine, alanine, threonine, glycine, valine or leucine.

Furthermore, the variant of the invention may, as the only modification or in combination with any of the above outlined modifications, be modified so that one or more Asp and/or Glu present in an amino acid fragment corresponding to the amino acid sequence fragment 185-209 of SEQ ID NO: 2 is/are replaced by an Asn and/or Gln, respectively. Also of interest is the replacement of one or more of the Lys residues present in the Termamyl-like α-amylase by an Arg residue.

It will be understood that in accordance with the present invention variants may be prepared which carry two or more of the above outlined modifications. For instance, variants may be prepared which comprises a modification in the loop 1 and loop 2 region, a modification in loop 2 and limited loop 3, a modification in loop 1, loop 2, loop 3 and loop 8, etc.

Furthermore, it may be advantageous to introduce point-mutations in any of the variants described herein.

Methods of Preparing α-Amylase Variants

Several methods for introducing mutations into genes are known in the art. After a brief discussion of the cloning of α-amylase-encoding DNA sequences, methods for generating mutations at specific sites within the α-amylase-encoding sequence will be discussed.

Cloning a DNA Sequence Encoding an α-Amylase

The DNA sequence encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labelled oligonucleotide probes may be synthesized and used to identify α-amylase-encoding clones from a genomic library prepared from the organism in question. Alternatively, a labelled oligonucleotide probe containing sequences homologous to a known α-amylase gene could be used as a probe to identify α-amylase-encoding clones, using hybridization and washing conditions of lower stringency.

Yet another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoroamidite method described by S. L. Beaucage and M. H. Caruthers (1981) or the method described by Matthes et al. (1984). In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Site-Directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into α-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localized or region-specific random mutagenesis in at least three parts of the gene translating to the amino acid sequence shown in question, or within the whole gene.

For region-specific random mutagenesis with a view to improving the thermal stability of a parent Termamyl-like α-amylase, codon positions corresponding to the following amino acid residues of the *B. licheniformis* α-amylase (SEQ ID NO: 2) may appropriately be targeted:

To Improve the Stability of the Calcium Site Between Domain A and C
I428-A435
T297-L308
F403-V409
To Improve the Stability Between Domain A and B:
D180-D204
H156-T163
A232-F238

With a view to achieving improved binding of a substrate (i.e. improved binding of a carbohydrate species, such as amylose or amylopectin) by a Termamyl-like α-amylase variant, modified (e.g. higher) substrate specificity and/or modified (e.g. higher) specificity with respect to cleavage (hydrolysis) of substrate, it appears that the following codon positions for the amino acid sequence shown in SEQ ID NO: 2 (or equivalent codon positions for another parent Termamyl-like α-amylase in the context of the invention) may particularly appropriately be targeted:
13-18
50-56
70-76
102-109
163-172
189-199
229-235
360-364
327-335

The random mutagenesis of a DNA sequence encoding a parent α-amylase to be performed in accordance with step a) of the above-described method of the invention may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the amylolytic enzyme by any published technique, using e.g. PCR, LCR or any DNA polymerase and ligase.

When PCR-generated mutagenesis is used, either a chemically treated or non-treated gene encoding a parent α-amylase enzyme is subjected to PCR under conditions that increase the misincorporation of nucleotides (Deshler 1992; Leung et al., Technique, Vol. 1, 1989, pp. 11-15).

A mutator strain of *E. coli* (Fowler et al., Molec. Gen. Genet., 133, 1974, pp. 179-191), *S. cereviseae* or any other microbial organism may be used for the random mutagenesis of the DNA encoding the amylolytic enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent amylolytic enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step (b) or the screening step (c) being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: grampositive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gramnegative bacteria such as *E. coli*.

The mutated DNA sequence may further comprise a DNA sequence encoding functions permitting expression of the mutated DNA sequence.

Localized random mutagenesis: the random mutagenesis may advantageously be localized to a part of the parent α-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized random mutagenesis is conveniently performed by use of PCR-generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

With respect to the screening step in the above-mentioned method of the invention, this may conveniently performed by use of a filter assay based on the following principle:

A microorganism capable of expressing the mutated amylolytic enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g. nylon or nitrocellulose. The topfilter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent e.g. agarose, agar, gelatine, polyacrylamide, starch, filter paper, cloth; or any combination of immobilizing agents.

α-Amylase activity is detected by Cibacron Red labelled amylopectin, which is immobilized on agarose. For screening for variants with increased thermal and high-pH stability, the filter with bound α-amylase variants is incubated in a buffer at pH 10.5 and 60° or 65° C. for a specified time, rinsed briefly in deionized water and placed on the amylopectin-agarose matrix for activity detection. Residual activity is seen as lysis of Cibacron Red by amylopectin degradation. The conditions are chosen to be such that activity due to the α-amylase having the amino acid sequence shown in SEQ ID NO: 1 can barely be detected. Stabilized variants show, under the same conditions, increased colour intensity due to increased liberation of Cibacron Red.

For screening for variants with an activity optimum at a lower temperature and/or over a broader temperature range, the filter with bound variants is placed directly on the amylopectin-Cibacron Red substrate plate and incubated at the desired temperature (e.g. 4° C., 10° C. or 30° C.) for a specified time. After this time activity due to the α-amylase having the amino acid sequence shown in SEQ ID NO: 1 can barely be detected, whereas variants with optimum activity at a lower temperature will show increase amylopectin lysis. Prior to incubation onto the amylopectin matrix, incubation in all kinds of desired media—e.g. solutions containing $Ca^{2+}$, detergents, EDTA or other relevant additives—can be carried out in order to screen for changed dependency or for reaction of the variants in question with such additives.

Testing of Variants of the Invention

The testing of variants of the invention may suitably be performed by determining the starch-degrading activity of the variant, for instance by growing host cells transformed with a DNA sequence encoding a variant on a starch-containing agarose plate and identifying starch-degrading host cells. Further testing as to altered properties (including specific activity, substrate specificity, cleavage pattern, thermoactivation, pH optimum, pH dependency, temperature optimum, and any other parameter) may be performed in accordance with methods known in the art.

Expression of α-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an α-amylase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an α-amylase variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the α-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g. as described in WO 91/17243.

While intracellular expression may be advantageous in some respects, e.g. when using certain bacteria as host cells, it is generally preferred that the expression is extracellular. In general, the *Bacillus* α-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an α-amylase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of an α-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are grampositive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gramnegative bacteria such as *E.*

*coli*. The transformation of the bacteria may, for instance, be effected by protoplast transformation or by using competent cells in a manner known per se.

The yeast organism may favourably be selected from a species of *Saccharomyces* or *Schizosaccharomyces*, e.g. *Saccharomyces cerevisiae*. The filamentous fungus may advantageously belong to a species of *Aspergillus*, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, the present invention relates to a method of producing an α-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the α-amylase variant of the invention. Suitable media are available from commercial suppliers or may be prepared according to published recipes (e.g. as described in catalogues of the American Type Culture Collection).

The α-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

INDUSTRIAL APPLICATIONS

The α-amylase variants of this invention possesses valuable properties allowing for various industrial applications. In particular the enzyme variants finds potential applications as a component in washing, dishwashing and hard surface cleaning detergent compositions, but it may also be useful in the production of sweeteners and ethanol from starch and for textile desizing. Conditions for conventional starch converting processes and liquefaction and/or saccharification processes are described in for instance U.S. Pat. No. 3,912,590 and EP patent publications Nos. 252,730 and 63,909.

Production of sweeteners from starch: A "traditional" process for conversion of starch to fructose syrups normally consists of three consecutive enzymatic processes, viz. a liquefaction process followed by a saccharification process and an isomerization process. During the liquefaction process, starch is degraded to dextrins by an α-amylase (e.g. Termamyl™) at pH values between 5.5 and 6.2 and at temperatures of 95-160° C. for a period of approx. 2 h. In order to ensure an optimal enzyme stability under these conditions, 1 mM of calcium is added (40 ppm free calcium ions).

After the liquefaction process the dextrins are converted into dextrose by addition of a glucoamylase (e.g. AMG™) and a debranching enzyme, such as an isoamylase or a pullulanase (e.g. Promozyme™). Before this step the pH is reduced to a value below 4.5, maintaining the high temperature (above 95° C.), and the liquefying α-amylase activity is denatured. The temperature is lowered to 60° C., and glucoamylase and debranching enzyme are added. The saccharification process proceeds for 24-72 hours.

After the saccharification process the pH is increased to a value in the range of 6-8, preferably pH 7.5, and the calcium is removed by ion exchange. The dextrose syrup is then converted into high fructose syrup using, e.g., an immobilized glucoseisomerase (such as Sweetzyme™)

At least 3 enzymatic improvements of this process could be obtained. All three improvements could be seen as individual benefits, but any combination (e.g. 1+2, 1+3, 2+3 or 1+2+3) could be employed:

Improvement 1. Reduction of the Calcium Dependency of the Liquefying Alpha-Amylase.

Addition of free calcium is required to ensure adequately high stability of the α-amylase, but free calcium strongly inhibits the activity of the glucoseisomerase and needs to be removed, by means of an expensive unit operation, to an extent which reduces the level of free calcium to below 3-5 ppm. Cost savings could be obtained if such an operation could be avoided and the liquefaction process could be performed without addition of free calcium ions.

To achieve that, a less calcium-dependent Termamyl-like α-amylase which is stable and highly active at low concentrations of free calcium (<40 ppm) is required. Such a Termamyl-like α-amylase should have a pH optimum at a pH in the range of 4.5-6.5, preferably in the range of 4.5-5.5.

Improvement 2. Reduction of Formation of Unwanted Maillard Products

The extent of formation of unwanted Maillard products during the liquefaction process is dependent on the pH. Low pH favours reduced formation of Maillard products. It would thus be desirable to be able to lower the process pH from around pH 6.0 to a value around pH 4.5; unfortunately, all commonly known, thermostable Termamyl-like α-amylases are not very stable at low pH (i.e. pH<6.0) and their specific activity is generally low.

Achievement of the above-mentioned goal requires a Termamyl-like α-amylase which is stable at low pH in the range of 4.5-5.5 and at free calcium concentrations in the range of 0-40 ppm, and which maintains a high specific activity.

Improvement 3.

It has been reported previously (U.S. Pat. No. 5,234,823) that when saccharifying with *A. niger* glucoamylase and *B. acidopullulyticus* pullulanase, the presence of residual α-amylase activity from the liquefaction process can lead to lower yields of dextrose if the α-amylase is not inactivated before the saccharification stage. This inactivation can typically be carried out by adjusting the pH to below 4.3 at 95° C., before lowering the temperature to 60° C. for saccharification.

The reason for this negative effect on dextrose yield is not fully understood, but it is assumed that the liquefying α-amylase (for example Termamyl™ 120 L from *B. licheniformis*) generates "limit dextrins" (which are poor substrates for *B. acidopullulyticus* pullulanase) by hydrolysing 1,4-alpha-glucosidic linkages close to and on both sides of the branching points in amylopectin. Hydrolysis of these limit dextrins by glucoamylase leads to a build-up of the trisaccharide panose, which is only slowly hydrolysed by glucoamylase.

The development of a thermostable α-amylase which does not suffer from this disadvantage would be a significant process improvement, as no separate inactivation step would be required.

If a Termamyl-like, low-pH-stable α-amylase is developed, an alteration of the specificity could be an advantage needed in combination with increased stability at low pH.

The methodology and principles of the present invention make it possible to design and produce variants according to the invention having required properties as outlined above. In this connection, mutations in a Termamyl-like α-amylase [for example Termamyl itself (*B. licheniformis* α-amylase; SEQ ID NO: 2); or a Termamyl-like α-amylase having an N-terminal amino acid sequence (i.e. the partial sequence up to the amino acid position corresponding to position 35 in Termamyl) which is identical to that in *B. amyloliquefaciens* α-amylase (SEQ ID NO: 4), i.e. a Termamyl-like α-amylase having the following N-terminal sequence relative to amino acid sequence of Termamyl:
A1*+N2*+L3V+M15T+R23K+S29A+A30E+Y31H+ A33S+E34D+H35I, where an asterisk (*) indicates deletion of the amino acid residue in question] at positions corresponding to any of the following positions in Termamyl are particularly interesting:
H133
H156
A181
A209
G310
H450
V128
N104
V54
S187
H293
A294
(where each of the latter amino acid residues may be replaced by any other amino acid residue, i.e. any other residue chosen among A, R, N, D, C, Q, E, G, H, I, L, K, M, F, P, S, T, W, Y and V), as well as the following triple deletions:
K370*+G371*+D372*
D372*+S373*+Q374*

Particularly preferred substitutions at the above-indicated positions are the following:
H133I
H156Y
A181T
A209V
G310D
H450Y
V128E
N104D
V54W,Y,F,I,L
S187D
H293Y
A294V.

Any combination of one or more (i.e. one, two, three, four ... etc.) of the above indicated mutations may appropriately be effected in a Termamyl-like α-amylase in the context in question, and particularly interesting variants of the invention in the context of achieving one or more of the above-mentioned improvements in relation to the starch liquefaction behaviour of α-amylases include variants comprising combinations of multiple mutations corresponding to the following combinations of mutations in Termamyl itself:
H133I+H156Y+A181T+A209V+G310D+H450Y+V128E+ N104D+V54W+S187D+H293Y+A294V+K370*+G371*+ D372*;
H133I+H156Y+A181T+A209V+G310D+H450Y+V128E+ N104D+V54W+S187D+H293Y+A294V+D372*+S373*+ Q374*;
H133I+H156Y+A181T+A209V+G310D+H450Y+V128E+ N104D+V54Y+S187D+H293Y+A294V+K370*+G371*+ D372*;
H133I+H156Y+A181T+A209V+G310D+H450Y+V128E+ N104D+V54Y+S187D+H293Y+A294V+D372*+S373*+ Q374*;
H133I+H156Y+A181T+A209V+G310D+H450Y+V128E+ N104D+V54F+S187D+H293Y+A294V+K370*+G371*+ D372*;
H133I+H156Y+A181T+A209V+G310D+H450Y+V128E+ N104D+V54F+S187D+H293Y+A294V+D372*+S373*+ Q374*;
H133I+H156Y+A181T+A209V+G310D+H450Y+V128E+ N104D+V54L+S187D+H293Y+A294V+K370*+G371*+ D372*;
H133I+H156Y+A181T+A209V+G310D+H450Y+V128E+ N104D+V54L+S187D+H293Y+A294V+D372*+S373*+ Q374*;
H133I+H156Y+A181T+A209V+G310D+H450Y+V128E+ N104D+V54L+S187D+H293Y+A294V+K370*+G371*+ D372*;
H133I+H156Y+A181T+A209V+G310D+H450Y+V128E+ N104D+V54L+S187D+H293Y+A294V+D372*+S373*+ Q374*;

Detergent Compositions

According to the invention, the α-amylase may typically be a component of a detergent composition. As such, it may be included in the detergent composition in the form of a non-dusting granulate, a stabilized liquid, or a protected enzyme. Non-dusting granulates may be produced, e.g. as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% of water and 0-30% of organic solvent, or nonaqueous.

The detergent composition comprises one or more surfactants, each of which may be anionic, nonionic, cationic, or zwitterionic. The detergent will usually contain 0-50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0-40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as lipase, cutinase, protease, cellulase, peroxidase, e.g., laccase.

The detergent may contain 1-65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxy acids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7-11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7-12% |
| Alcohol ethoxysulfate (e.g., $C_{12-18}$ alcohol, 1-2 EO) or alkyl sulfate (e.g., $C_{16-18}$) | 1-4% |
| Alcohol ethoxylate (e.g., $C_{14-15}$ alcohol, 7 EO) | 5-9% |
| Sodium carbonate (as $Na_2CO_3$) | 14-20% |
| Soluble silicate (as $Na_2O, 02SiO_2$) | 2-6% |
| Zeolite (as $NaAlSiO_4$) | 15-22% |
| Sodium sulfate (as $Na_2SO_4$) | 0-6% |
| Sodium citrate/citric acid (as $C_6H_5Na_3O_7/C_6H_8O_7$) | 0-15% |
| Sodium perborate (as $NaBO_3 \cdot H_2O$) | 11-18% |
| TAED | 2-6% |
| Carboxymethylcellulose | 0-2% |
| Polymers (e.g., maleic/acrylic acid copolymer, PVP, PEG) | 0-3% |
| Enzymes (calculated as pure enzyme protein) | 0.0001-0.1% |
| Minor ingredients (e.g., suds suppressors, perfume, optical brightener, photobleach) | 0-5% |

2) A detergent composition formulated as a granulate having a bulk density of at least 600 WI comprising

| | |
|---|---|
| Linear alkylbenzenesulfonate (calculated as acid) | 6-11% |
| Alcohol ethoxysulfate (e.g., $C_{12-18}$ alcohol, 1-2 EO) or alkyl sulfate (e.g., $C_{16-18}$) | 1-3% |
| Alcohol ethoxylate (e.g., $C_{14-15}$ alcohol, 7 EO) | 5-9% |
| Sodium carbonate (as $Na_2CO_3$) | 15-21% |
| Soluble silicate (as $Na_2O, 2SiO_2$) | 1-4% |
| Zeolite (as $NaAlSiO_4$) | 24-34% |
| Sodium sulfate (as $Na_2SO_4$) | 4-10% |
| Sodium citrate/citric acid (as $C_6H_5Na_3O_7/C_6H_8O_7$) | 0-15% |
| Carboxymethylcellulose | 0-2% |

-continued

| | |
|---|---|
| Polymers (e.g., maleic/acrylic acid copolymer, PVP, PEG) | 1-6% |
| Enzymes (calculated as pure enzyme protein) | 0.0001-0.1% |
| Minor ingredients (e.g., suds suppressors, perfume) | 0-5% |

3) A detergent composition formulated as a granulate having a bulk density of at least 600 g/l comprising

| | |
|---|---|
| Linear alkylbenzenesulfonate (calculated as acid) | 5-9% |
| Alcohol ethoxylate (e.g., $C_{12-15}$ alcohol, 7 EO) | 7-14% |
| Soap as fatty acid (e.g., $C_{16-22}$ fatty acid) | 1-3% |
| Sodium carbonate (as $Na_2CO_3$) | 10-17% |
| Soluble silicate (as $Na_2O, 2SiO_2$) | 3-9% |
| Zeolite (as $NaAlSiO_4$) | 23-33% |
| Sodium sulfate (as $Na_2SO4$) | 0-4% |
| Sodium perborate (as $NaBO_3 \cdot H_2O$) | 8-16% |
| TAED | 2-8% |
| Phosphonate (e.g., EDTMPA) | 0-1% |
| Carboxymethylcellulose | 0-2% |
| Polymers (e.g., maleic/acrylic acid copolymer, PVP, PEG) | 0-3% |
| Enzymes (calculated as pure enzyme protein) | 0.0001-0.1% |
| Minor ingredients (e.g., suds suppressors, perfume, optical brightener) | 0-5% |

4) A detergent composition formulated as a granulate having a bulk density of at least 600 g/l comprising

| | |
|---|---|
| Linear alkylbenzenesulfonate (calculated as acid) | 8-12% |
| Alcohol ethoxylate (e.g., $C_{12-15}$ alcohol, 7 EO) | 10-25% |
| Sodium carbonate (as $Na_2CO_3$) | 14-22% |
| Soluble silicate (as $Na_2O, 2SiO_2$) | 1-5% |
| Zeolite (as $NaAlSiO_4$) | 25-35% |
| Sodium sulfate (as $Na_2SO_4$) | 0-10% |
| Carboxymethylcellulose | 0-2% |
| Polymers (e.g., maleic/acrylic acid copolymer, PVP, PEG) | 1-3% |
| Enzymes (calculated as pure enzyme protein) | 0.0001-0.1% |
| Minor ingredients (e.g., suds suppressors, perfume) | 0-5% |

5) An aqueous liquid detergent composition comprising

| | |
|---|---|
| Linear alkylbenzenesulfonate (calculated as acid) | 15-21% |
| Alcohol ethoxylate (e.g., $C_{12-15}$ alcohol, 7 EO or $C_{12-15}$ alcohol, 5 EO) | 12-18% |
| Soap as fatty acid (e.g., oleic acid) | 3-13% |
| Alkenylsuccinic acid ($C_{12-14}$) | 0-13% |
| Aminoethanol | 8-18% |
| Citric acid | 2-8% |
| Phosphonate | 0-3% |
| Polymers (e.g., PVP, PEG) | 0-3% |
| Borate (as $B_4O_7$) | 0-2% |
| Ethanol | 0-3% |
| Propylene glycol | 8-14% |
| Enzymes (calculated as pure enzyme protein) | 0.0001-0.1% |
| Minor ingredients (e.g., dispersants, suds suppressors, perfume, optical brightener) | 0-5% |

6) An aqueous structured liquid detergent composition comprising

| | |
|---|---|
| Linear alkylbenzenesulfonate (calculated as acid) | 15-21% |
| Alcohol ethoxylate (e.g., $C_{12-15}$ alcohol, 7 EO, or $C_{12-15}$ alcohol, 5 EO) | 3-9% |
| Soap as fatty acid (e.g., oleic acid) | 3-10% |

-continued

| | |
|---|---|
| Zeolite (as NaAlSiO$_4$) | 14-22% |
| Potassium citrate | 9-18% |
| Borate (as B$_4$O$_7$) | 0-2% |
| Carboxymethylcellulose | 0-2% |
| Polymers (e.g., PEG, PVP) | 0-3% |
| Anchoring polymers such as, e.g., lauryl methacrylate/acrylic acid copolymer; molar ratio 25:1; MW 3800 | 0-3% |
| Glycerol | 0-5% |
| Enzymes (calculated as pure enzyme protein) | 0.0001-0.1% |
| Minor ingredients (e.g., dispersants, suds suppressors, perfume, optical brighteners) | 0-5% |

7) A detergent composition formulated as a granulate having a bulk density of at least 600 g/l comprising

| | |
|---|---|
| Fatty alcohol sulfate | 5-10% |
| Ethoxylated fatty acid monoethanolamide | 3-9% |
| Soap as fatty acid | 0-3% |
| Sodium carbonate (as Na$_2$CO$_3$) | 5-10% |
| Soluble silicate (as Na$_2$O, 2SiO$_2$) | 1-4% |
| Zeolite (as NaAlSiO$_4$) | 20-40% |
| Sodium sulfate (as Na$_2$SO$_4$) | 2-8% |
| Sodium perborate (as NaBO$_3$•H$_2$O) | 12-18% |
| TAED | 2-7% |
| Polymers (e.g., maleic/acrylic acid copolymer, PEG) | 1-5% |
| Enzymes (calculated as pure enzyme protein) | 0.0001-0.1% |
| Minor ingredients (e.g., optical brightener, suds suppressors, perfume) | 0-5% |

8) A detergent composition formulated as a granulate comprising

| | |
|---|---|
| Linear alkylbenzenesulfonate (calculated as acid) | 8-14% |
| Ethoxylated fatty acid monoethanolamide | 5-11% |
| Soap as fatty acid | 0-3% |
| Sodium carbonate (as Na$_2$CO$_3$) | 4-10% |
| Soluble silicate (as Na$_2$O, 2SiO$_2$) | 1-4% |
| Zeolite (as NaAlSiO$_4$) | 30-50% |
| Sodium sulfate (as Na$_2$SO$_4$) | 3-11% |
| Sodium citrate (as C$_6$H$_5$Na$_3$O$_7$) | 5-12% |
| Polymers (e.g., PVP, maleic/acrylic acid copolymer, PEG) | 1-5% |
| Enzymes (calculated as pure enzyme protein) | 0.0001-0.1% |
| Minor ingredients (e.g., suds suppressors, perfume) | 0-5% |

9) A detergent composition formulated as a granulate comprising

| | |
|---|---|
| Linear alkylbenzenesulfonate (calculated as acid) | 6-12% |
| Nonionic surfactant | 1-4% |
| Soap as fatty acid | 2-6% |
| Sodium carbonate (as Na$_2$CO$_3$) | 14-22% |
| Zeolite (as NaAlSiO$_4$) | 18-32% |
| Sodium sulfate (as Na$_2$SO$_4$) | 5-20% |
| Sodium citrate (as C$_6$H$_5$Na$_3$O$_7$) | 3-8% |
| Sodium perborate (as NaBO$_3$•H$_2$O) | 4-9% |
| Bleach activator (e.g., NOBS or TAED) | 1-5% |
| Carboxymethylcellulose | 0-2% |
| Polymers (e.g., polycarboxylate or PEG) | 1-5% |
| Enzymes (calculated as pure enzyme protein) | 0.0001-0.1% |
| Minor ingredients (e.g., optical brightener, perfume) | 0-5% |

10) An aqueous liquid detergent composition comprising

| | |
|---|---|
| Linear alkylbenzenesulfonate (calculated as acid) | 15-23% |
| Alcohol ethoxysulfate (e.g., C$_{12-15}$ alcohol, 2-3 EO) | 8-15% |
| Alcohol ethoxylate (e.g., C$_{12-15}$ alcohol, 7 EO, or C$_{12-15}$ alcohol, 5 EO) | 3-9% |
| Soap as fatty acid (e.g., lauric acid) | 0-3% |
| Aminoethanol | 1-5% |
| Sodium citrate | 5-10% |
| Hydrotrope (e.g., sodium toluensulfonate) | 2-6% |
| Borate (as B$_4$O$_7$) | 0-2% |
| Carboxymethylcellulose | 0-1% |
| Ethanol | 1-3% |
| Propylene glycol | 2-5% |
| Enzymes (calculated as pure enzyme protein) | 0.0001-0.1% |
| Minor ingredients (e.g., polymers, dispersants, perfume, optical brighteners) | 0-5% |

11) An aqueous liquid detergent composition comprising

| | |
|---|---|
| Linear alkylbenzenesulfonate (calculated as acid) | 20-32% |
| Alcohol ethoxylate (e.g., C$_{12-15}$ alcohol, 7 EO, or C$_{12-15}$ alcohol, 5 EO) | 6-12% |
| Aminoethanol | 2-6% |
| Citric acid | 8-14% |
| Borate (as B$_4$O$_7$) | 1-3% |
| Polymer (e.g., maleic/acrylic acid copolymer, anchoring polymer such as, e.g., lauryl methacrylate/acrylic acid copolymer) | 0-3% |
| Glycerol | 3-8% |
| Enzymes (calculated as pure enzyme protein) | 0.0001-0.1% |
| Minor ingredients (e.g., hydrotropes, dispersants, perfume, optical brighteners) | 0-5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25-40% |
| Nonionic surfactant (e.g., alcohol ethoxylate) | 1-10% |
| Sodium carbonate (as Na$_2$CO$_3$) | 8-25% |
| Soluble silicates (as Na$_2$O, 2SiO$_2$) | 5-15% |
| Sodium sulfate (as Na$_2$SO$_4$) | 0-5% |
| Zeolite (as NaAlSiO$_4$) | 15-28% |
| Sodium perborate (as NaBO$_3$•4H$_2$O) | 0-20% |
| Bleach activator (TAED or NOBS) | 0-5% |
| Enzymes (calculated as pure enzyme protein) | 0.0001-0.1% |
| Minor ingredients (e.g., perfume, optical brighteners) | 0-3% |

13) Detergent compositions as described in compositions 1-12 wherein all or part of the linear alkylbenzenesulfonate is replaced by (C$_{12}$-C$_{18}$) alkyl sulfate.

14) A detergent composition formulated as a granulate having a bulk density of at least 600 g/l comprising

| | |
|---|---|
| (C$_{12}$-C$_{18}$) alkyl sulfate | 9-15% |
| Alcohol ethoxylate | 3-6% |
| Polyhydroxy alkyl fatty acid amide | 1-5% |
| Zeolite (as NaAlSiO$_4$) | 10-20% |
| Layered disilicate (e.g., SK56 from Hoechst) | 10-20% |
| Sodium carbonate (as Na$_2$CO$_3$) | 3-12% |
| Soluble silicate (as Na$_2$O, 2SiO$_2$) | 0-6% |
| Sodium citrate | 4-8% |
| Sodium percarbonate | 13-22% |
| TAED | 3-8% |
| Polymers (e.g., polycarboxylates and PVP) | 0-5% |

-continued

| | |
|---|---|
| Enzymes (calculated as pure enzyme protein) | 0.0001-0.1% |
| Minor ingredients (e.g., optical brightener, photo bleach, perfume, suds suppressors) | 0-5% |

15) A detergent composition formulated as a granulate having a bulk density of at least 600 g/l comprising

| | |
|---|---|
| ($C_{12}$-$C_{18}$) alkyl sulfate | 4-8% |
| Alcohol ethoxylate | 11-15% |
| Soap | 1-4% |
| Zeolite MAP or zeolite A | 35-45% |
| Sodium carbonate (as $Na_2CO_3$) | 2-8% |
| Soluble silicate (as $Na_2O, 2SiO_2$) | 0-4% |
| Sodium percarbonate | 13-22% |
| TAED | 1-8% |
| Carboxymethyl cellulose | 0-3% |
| Polymers (e.g., polycarboxylates and PVP) | 0-3% |
| Enzymes (calculated as pure enzyme protein) | 0.0001-0.1% |
| Minor ingredients (e.g., optical brightener, phosphonate, perfume) | 0-3% |

16) Detergent formulations as described in 1)-15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", *Nature* 369, 1994, pp. 637-639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The α-amylase variant of the invention may be incorporated in concentrations conventionally employed in detergents. It is at present contemplated that, in the detergent composition of the invention, the α-amylase may be added in an amount corresponding to 0.00001-1 mg (calculated as pure enzyme protein) of α-amylase per liter of wash liquor.

Dishwashing Composition

The dishwashing detergent composition comprises a surfactant which may be anionic, non-ionic, cationic, amphoteric or a mixture of these types. The detergent will contain 0-90% of non-ionic surfactant such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1-90% of detergent builders.

Examples of phosphorus-containing inorganic alkaline detergent builders, when present, include the water-soluble salts especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates and silicates as well as the various types of water-insoluble crystalline or amorphous alumino silicates of which zeolites are the best-known representatives.

Examples of suitable organic builders include the alkali metal, ammonium and substituted ammonium, citrates, succinates, malonates, fatty acid sulphonates, carboxymethoxy succinates, ammonium polyacetates, carboxylates, polycarboxylates, aminopolycarboxylates, polyacetyl carboxylates and polyhydroxysulphonates.

Other suitable organic builders include the higher molecular weight polymers and co-polymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g. a polyol such as e.g. propylene glycol, a sugar or a sugar alcohol, lactic acid, boric acid, or a boric acid derivative, e.g. an aromatic borate ester.

The dishwashing detergent composition of the invention may also contain other conventional detergent ingredients, e.g. deflocculant material, filler material, foam depressors, anti-corrosion agents, soil-suspending agents, sequestering agents, anti-soil redeposition agents, dehydrating agents, dyes, bactericides, fluorescers, thickeners and perfumes.

Finally, the α-amylase variant of the invention may be used in conventional dishwashing detergents, e.g. in any of the detergents described in any of the following patent publications:

EP 518719, EP 518720, EP 518721, EP 516553, EP 516554, EP 516555, GB 2200132, DE 3741617, DE 3727911, DE 4212166, DE 4137470, DE 3833047, WO 93/17089, DE 4205071, WO 52/09680, WO 93/18129, WO 93/04153, WO 92/06157, WO 92/08777, EP 429124, WO 93/21299, U.S. Pat. No. 5,141,664, EP 561452, EP 561446, GB 2234980, WO 93/03129, EP 481547, EP 530870, EP 533239, EP 554943, EP 346137, U.S. Pat. No. 5,112,518, EP 318204, EP 318279, EP 271155, EP 271156, EP 346136, GB 2228945, CA 2006687, WO 93/25651, EP 530635, EP 414197, U.S. Pat. No. 5,240,632.

EXAMPLES

Example 1

Example on Homology Building of TERM

The overall homology of the *B. licheniformis* α-amylase (in the following referred to as TERM) to other Termamyl-like α-amylases is high and the percent similarity is extremely high. The similarity calculated for TERM to BSG (the *B. stearothermophilus* α-amylase with SEQ ID NO: 6), and BAN (the *B. amyloliquefaciens* α-amylase with SEQ ID NO: 4) using the University of Wisconsin Genetics Computer Group's program GCG gave 89% and 78%, respectively. TERM has a deletion of 2 residues between residue G180 and K181 compared to BAN and BSG. BSG has a deletion of 3 residues between G371 and I372 in comparison with BAN and TERM. Further BSG has a C-terminal extension of more than 20 residues compared to BAN and TERM. BAN has 2 residues less and TERM has one residue less in the N-terminal compared to BSG.

The structure of the *B. licheniformis* (TERM) and of the *B. amyloliquefaciens* α-amylase (BAN), respectively, was model built on the structure disclosed in Appendix 1 herein. The structure of other Termamyl-like α-amylases (e.g. those disclosed herein) may be built analogously.

In comparison with the α-amylase used for elucidating the present structure, TERM differs in that it lacks two residues around 178-182. In order to compensate for this in the model structure, the HOMOLOGY program from BIOSYM was used to substitute the residues in equivalent positions in the structure (not only structurally conserved regions) except for the deletion point. A peptide bond was established between G179(G177) and K180(K180) in TERM(BAN). The close structural relationship between the solved structure and the model structure (and thus the validity of the latter) is indicated by the presence of only very few atoms found to be too close together in the model.

To this very rough structure of TERM was then added all waters (605) and ions (4 Calcium and 1 Sodium) from the solved structure (Appendix 1) at the same coordinates as for said solved structure using the INSIGHT program. This could be done with only few overlaps—in other words with a very nice fit. This model structure were then minimized using 200 steps of Steepest descent and 600 steps of Conjugated gradient (see Brooks et al 1983, J. Computational Chemistry 4, p. 187-217). The minimized structure was then subjected to molecular dynamics, 5 ps heating followed by up to 200 ps equilibration but more than 35 ps. The dynamics as run with the Verlet algorithm and the equilibration temperature 300K were kept using the Behrendsen coupling to a waterbath (Berendsen et. al., 1984, J. Chemical Physics 81, p. 3684-3690). Rotations and translations were removed every picosecond. The potential energy became stable after appr. 35 ps equilibration. A mean dynamics structure was extracted and can be used for further analysis.

Example 2

Determination of Residues within 10 Å from the Ions Present in the Solved Structure The coordinates of Appendix 1 are read into the INSIGHT program provided by BIOSYM technologies. The spatial coordinates are presented showing the bonds between the atoms. The ions are presented as well as the water atoms. The program package part of creating subset are used to create a 10 Å subset around the Calcium and the Sodium ions in the structure using the command ZONE. All residues having an atom within the 10 Å are compiled and written out by the LIST MOLECULE command. By giving the ions the name ium in the coordinate file a 10 Å sphere around all atoms called ium is compiled. The specific residues identified in this manner are given further above in the section entitled "$Ca^{2+}$ dependency".

Example 3

Determination of Cavities in the Solved Structure

Appendix 1

The solved structure exhibits many internal holes and cavities. When analysing for such cavities the Connolly program is normally used (Lee, B. and Richards, F. M. (1971) J. Mol. Biol. 55, p. 379-400). The program uses a probe with radius to search the external and internal surface of the protein. The smallest hole observable in this way has the probe radius.

To analyse the solved structure a modified version of the Connolly program included in the program of INSIGHT were used. First the water molecules and the ions were removed by unmerging these atoms from the solved structure. By using the command MOLECULE SURFACE SOLVENT the solvent accessible surface area were calculated for all atoms and residues using a probe radius of 1.4 Å, and displayed on the graphics screen together with the model of the solved structure. The internal cavities where then seen as dot surfaces with no connections to external surface.

Mutant suggestions for filling out the holes are given in the specification (in the section entitled "Variants with increased thermostability and/or altered temperature optimum"). By using the homology build structures or/and the sequence alignment mutations for the homologous structures of TERM and BSG and BAN can be made.

Example 4

Construction of Termamyl Variants in Accordance with the Invention

Figure 9:
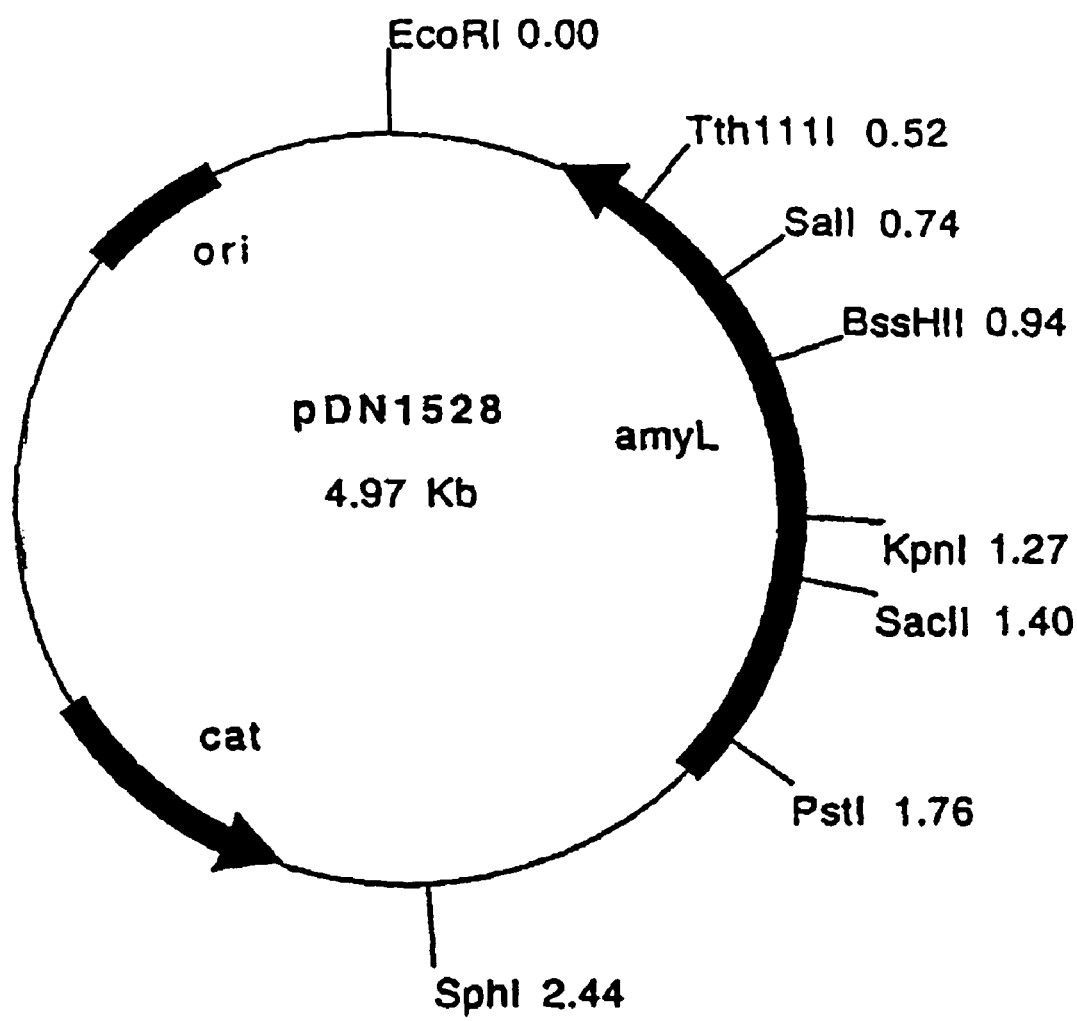
FIG. 9 is a schematic representation of the plasmid designated pDN1528.

Termamyl (SEQ ID NO: 2) is expressed in *B. subtilis* from a plasmid denoted pDN1528. This plasmid contains the complete gene encoding Termamyl, amyL, the expression of which is directed by its own promoter. Further, the plasmid contains the origin of replication, ori, from plasmid pUB110 and the cat gene from plasmid pC194 conferring resistance towards chloramphenicol. pDN1528 is shown in FIG. 9.

Figure 10:
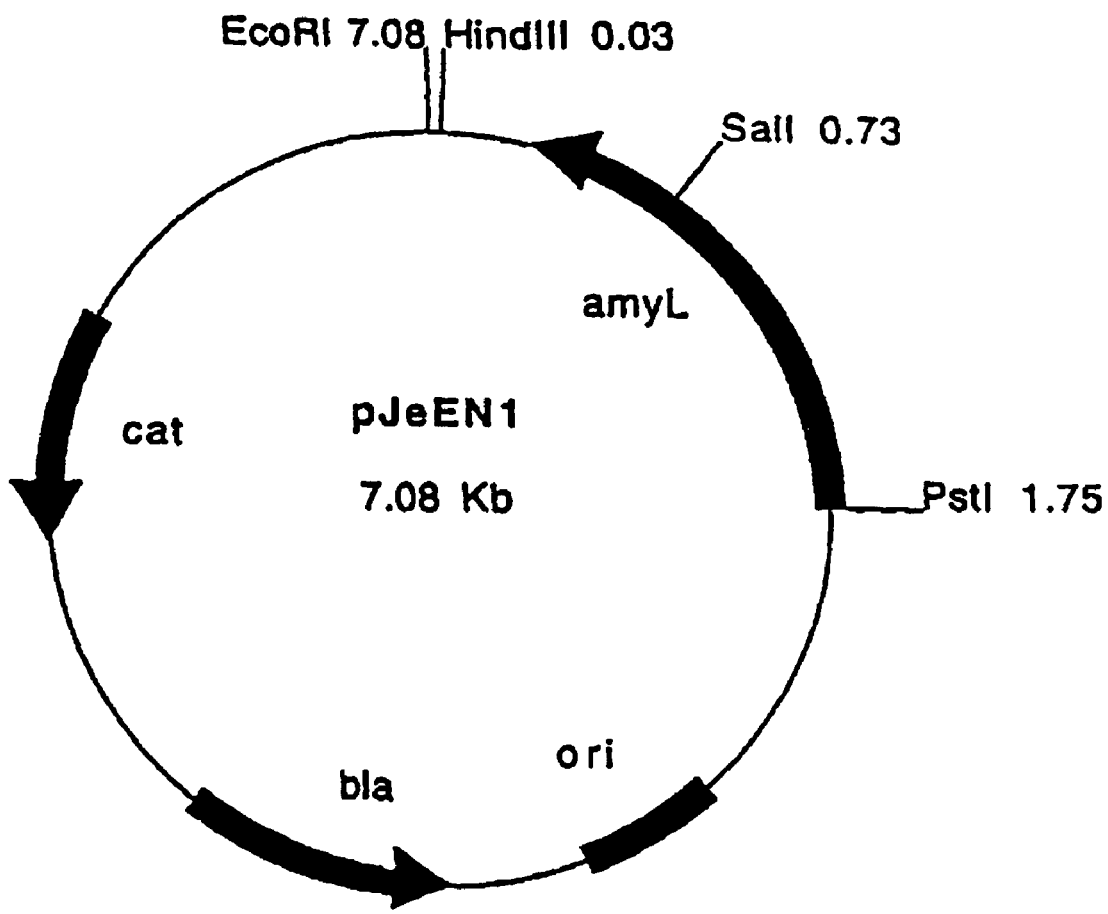
FIG. 10 is a schematic representation of the plasmid designated pJEN1.

A specific mutagenesis vector containing a major part of the coding region of SEQ ID NO: 1 was prepared. The important features of this vector, denoted pJeEN1, include an origin of replication derived from the pUC plasmids, the cat gene conferring resistance towards chloramphenicol, and a frameshift-containing version of the bla gene, the wild type of which normally confers resistance towards ampicillin ($amp^R$ phenotype). This mutated version results in an $amp^S$ phenotype. The plasmid pJeEN1 is shown in FIG. 10, and the *E. coli* origin of replication, ori, bla, cat, the 5'-truncated version of the Termamyl amylase gene, and selected restriction sites are indicated on the plasmid.

Mutations are introduced in amyL by the method described by Deng and Nickoloff (1992, *Anal. Biochem.* 200, pp. 81-88) except that plasmids with the "selection primer" (primer #6616; see below) incorporated are selected based on the $amp^R$ phenotype of transformed *E. coli* cells harboring a plasmid with a repaired bla gene, instead of employing the selection by restriction enzyme digestion outlined by Deng and Nickoloff. Chemicals and enzymes used for the mutagenesis were obtained from the Chameleon™ mutagenesis kit from Stratagene (catalogue number 200509).

After verification of the DNA sequence in variant plasmids, the truncated gene, containing the desired alteration, is subcloned into pDN1528 as a PstI-EcoRI fragment and transformed into a protease- and amylase-depleted *Bacillus subtilis* strain in order to express the variant enzyme.

The Termamyl variant V54W was constructed by the use of the following mutagenesis primer (written 5' to 3', left to right):

```
P GTC GTA GGC ACC GTA GCC CCA ATC CGC TTG
```

The Termamyl variant A52W+V54W was constructed by the use of the following mutagenesis primer (written 5' to 3', left to right):

```
P GTC GTA GGC ACC GTA GCC CCA ATC CCA TTG GCT CG
```

Primer #6616 (written 5' to 3', left to right; P denotes a 5' phosphate):

```
P CTG TGA CTG GTG AGT ACT CAA CCA AGT C
```

Example 5

Saccharification in the Presence of "Residual" α-Amylase Activity

Two appropriate Termamyl variants with altered specificity were evaluated by saccharifying a DE 10 (DE=dextrose equivalent) maltodextrin substrate with *A. niger* glucoamylase and *B. acidopullulyticus* pullulanase under conditions where the variant amylase was active.

Saccharification: Substrates for saccharification were prepared by dissolving 230 g DE 10 spray-dried maltodextrin, prepared from common corn starch, in 460 ml boiling deionized water and adjusting the dry substance (DS) content to approximately 30% w/w. The pH was adjusted to 4.7 (measured at 60° C.) and aliquots of substrate corresponding to 15 g dry weight were transferred to 50 ml blue cap glass flasks.

The flasks were then placed in a shaking water bath equilibrated at 60° C., and the enzymes added. The pH was readjusted to 4.7 where necessary.

The following enzymes were used:
Glucoamylase: AMGT™ (Novo Nordisk A/S); dosage 0.18 AG/g DS
Pullulanase: Promozyme™ (Novo Nordisk NS); dosage 0.06 PUN/g DS
α-Amylases:
  Termamyl™ (Novo Nordisk NS); dosage 60 NU/g DS
  Termamyl variant V54W; dosage 60 NU/g DS
  Termamyl variant V54W+A52W; dosage 60 NU/g DS 2 ml samples were taken periodically. The pH of each sample was adjusted to about 3.0, and the sample was then heated in a boiling water bath for 15 minutes to inactivate the enzymes. After cooling, the samples were treated with approximately 0.1 g mixed-bed ion exchange resin (BIO-Rad 501-X (D)) for 30 minutes on a rotary mixer and then filtered. The carbohydrate composition of each sample was determined by HPLC. The following results were obtained after 72 hours [$DP_n$ denotes a dextrose (D-glucose) oligomer with n glucose units]:

| α-amylase | % $DP_1$ | % $DP_2$ | % $DP_3$ | % $DP_4$ |
|---|---|---|---|---|
| None (control) | 95.9 | 2.8 | 0.4 | 1.0 |
| V54W | 96.0 | 2.9 | 0.4 | 0.8 |
| V54W + A52W | 95.9 | 2.8 | 0.4 | 0.8 |
| Termamyl ™ | 95.6 | 2.8 | 0.8 | 0.8 |

It can be seen from the above results that compared with the control (no α-amylase activity present during liquefaction), the presence of α-amylase activity from variants V54W and V54W+A52W did not lead to elevated panose ($DP_3$) levels. In contrast, Termamyl α-amylase activity resulted in higher levels of panose and a subsequent loss of D-glucose ($DP_1$) yield.

Thus, if α-amylase variants V54W or V54W+A52W are used for starch liquefaction, it will not be necessary to inactivate the residual α-amylase activity before the commencement of saccharification.

Example 6

Calcium-Binding Affinity of α-Amylase Variants of the Invention

Unfolding of amylases by exposure to heat or to denaturants such as guanidine hydrochloride is accompanied by a decrease in fluorescence. Loss of calcium ions leads to unfolding, and the affinity of α-amylases for calcium can be measured by fluorescence measurements before and after incubation of each α-amylase (e.g. at a concentration of 10 μg/ml) in a buffer (e.g. 50 mM HEPES, pH 7) with different concentrations of calcium (e.g. in the range of 1 μM-100 mM) or of EGTA (e.g. in the range of 1-1000 μM) [EGTA=1,2-di (2-aminoethoxy)ethane-N,N,N',N'-tetraacetic acid] for a sufficiently long period of time (such as 22 hours at 55° C.).

The measured fluorescence F is composed of contributions form the folded and unfolded forms of the enzyme. The following equation can be derived to describe the dependence of F on calcium concentration ([Ca]):

$$F=[Ca]/(K_{diss}[Ca])(\alpha_N-\beta_N \log([Ca])+K_{diss}/(K_{diss}[Ca])(\alpha_U-\beta_U \log([Ca])$$

where $\alpha_N$ is the fluorescence of the native (folded) form of the enzyme, $\beta_N$ is the linear dependence of $\alpha_N$ on the logarithm of the calcium concentration (as observed experimentally), $\alpha_U$ is the fluorescence of the unfolded form and $\beta_U$ is the linear dependence of $\alpha_U$ on the logarithm of the calcium concentration. $K_{diss}$ is the apparent calcium-binding constant for an equilibrium process as follows:

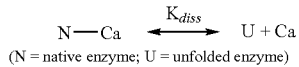

(N = native enzyme; U = unfolded enzyme)

In fact, unfolding proceeds extremely slowly and is irreversible. The rate of unfolding is a dependent on calcium concentration, and the dependency for a given α-amylase provides a measure of the Ca-binding affinity of the enzyme. By defining a standard set of reaction conditions (e.g. 22 hours at 55° C.), a meaningful comparison of $K_{diss}$ for different α-amylases can be made. The calcium dissociation curves for α-amylases in general can be fitted to the equation above, allowing determination of the corresponding values of $K_{diss}$.

The following values for $K_{diss}$ were obtained for a parent Termamyl-like α-amylase having the amino acid sequence shown in SEQ ID NO: 1 of WO 95/26397 and for the indicated variant thereof according to the invention:

| α-Amylase | $K_{diss}$ (mol/l) |
|---|---|
| L351C + M430C + T183* + G184* | 1.7 (±0.5) × $10^{-3}$ |
| Parent | 3.5 (±1.1) × $10^{-1}$ |

It is apparent from the above that the calcium-binding affinity of the variant in question binds calcium significantly more strongly than the parent, and thereby has a correspondingly lower calcium dependency than the parent.

REFERENCES CITED

Klein, C., et al., *Biochemistry* 1992, 31, 8740-8746,
Mizuno, H., et al., *J. Mol. Biol.* (1993) 234, 1282-1283,
Chang, C., et al, *J. Mol. Biol.* (1993) 229, 235-238,
Larson, S. B., *J. Mol. Biol.* (1994) 235, 1560-1584,
Lawson, C. L., *J. Mol. Biol.* (1994) 236, 590-600,
Qian, M., et al., *J. Mol. Biol.* (1993) 231, 785-799,
Brady, R. L., et al., *Acta Crystallogr.* sect. 8, 47, 527-535,
Swift, H. J., et al., *Acta Crystallogr.* sect. 8, 47, 535-544
A. Kadziola, Ph.D. Thesis: "An alpha-amylase from Barley and its Complex with a Substrate Analogue Inhibitor Studied by X-ray Crystallography", Department of Chemistry University of Copenhagen 1993
MacGregor, E. A., Food Hydrocolloids, 1987, Vat No. 5-6, p.
B. Diderichsen and L. Christiansen, Cloning of a maltogenic α-amylase from *Bacillus stearothermophilus*, FEMS Microbiol. letters: 56: pp. 53-60 (1988)
Hudson et al., Practical Immunology, Third edition (1989), Blackwell Scientific Publications,
Sambrook et al., *Molecular Cloning: A Laboratory Manual*, 2nd Ed., Cold Spring Harbor, 1989
S. L. Beaucage and M. H. Caruthers, *Tetrahedron Letters* 22, 1981, pp. 1859-1869
Matthes et al., *The EMBO J.* 3, 1984, pp. 801-805.
R. K. Saiki et al., *Science* 239, 1988, pp. 487-491.
Morinaga et al., (1984, Biotechnology 2:646-639)
Nelson and Long, *Analytical Biochemistry* 180, 1989, pp. 147-151
Hunkapiller et al., 1984, Nature 310:105-111
R. Higuchi, B. Krummel, and R. K. Saiki (1988). A general method of in vitro preparation and specific mutagenesis of DNA fragments: study of protein and DNA interactions. *Nucl. Acids Res.* 16:7351-7367.
Dubnau et al., 1971, *J. Mol. Biol.* 56, pp. 209-221.
Gryczan et al., 1978, *J. Bacteriol.* 134, pp. 318-329.
S. D. Erlich, 1977, *Proc. Natl. Acad. Sci.* 74, pp. 1680-1682.
Boel et al., 1990, *Biochemistry* 29 pp. 6244-6249.

The invention claimed is:

1. An isolated variant alpha-amylase, which comprises a substitution at a position corresponding to position 281 of SEQ ID NO: 2, wherein the variant is at least 90% homologous and less than 100% homologous to the amino acid sequence of SEQ ID NO: 2, 4, 6, or 13 when homology is determined by the GAP program (Genetic Computer Group, Version 7.0) using default values for GAP penalties and wherein the variant has alpha-amylase activity.

2. The variant alpha-amylase of claim 1, which is at least 90% homologous to the amino acid sequence of SEQ ID NO: 2.

3. The variant alpha-amylase of claim 1, which is at least 95% homologous to the amino acid sequence of SEQ ID NO: 2.

4. The variant alpha-amylase of claim 1, which is at least 90% homologous to the amino acid sequence of SEQ ID NO: 4.

5. The variant alpha-amylase of claim 1, which is at least 95% homologous to the amino acid sequence of SEQ ID NO: 4.

6. The variant alpha-amylase of claim 1, which is at least 90% homologous to the amino acid sequence of SEQ ID NO: 6.

7. The variant alpha-amylase of claim 1, which is at least 95% homologous to the amino acid sequence of SEQ ID NO: 6.

8. The variant alpha-amylase of claim 1, which is at least 90% homologous to the amino acid sequence of SEQ ID NO: 13.

9. The variant alpha-amylase of claim 1, which is at least 95% homologous to the amino acid sequence of SEQ ID NO: 13.

10. The variant alpha-amylase of claim 1, wherein the substitution is a substitution of His with a different amino acid.

11. The variant alpha-amylase of claim 10, wherein the different amino acid is Ile, Leu, or Phe.

12. The variant alpha-amylase of claim 3, wherein the substitution is a substitution of His with a different amino acid.

13. The variant alpha-amylase of claim 12, wherein the different amino acid is Ile, Leu, or Phe.

14. The variant alpha-amylase of claim 5, wherein the substitution is a substitution of His with a different amino acid.

15. The variant alpha-amylase of claim 14, wherein the different amino acid is Ile, Leu, or Phe.

16. The variant alpha-amylase of claim 7, wherein the substitution is a substitution of His with a different amino acid.

17. The variant alpha-amylase of claim 16, wherein the different amino acid is Ile, Leu, or Phe.

18. The variant alpha-amylase of claim 9, wherein the substitution is a substitution of His with a different amino acid.

19. The variant alpha-amylase of claim 18, wherein the different amino acid is Ile, Leu, or Phe.

20. A detergent composition, comprising a surfactant and a variant alpha-amylase of claim 1.

21. The detergent composition of claim 20, further comprising an enzyme selected from the group consisting of cellulose, lipase, peroxidase, and protease.

* * * * *